US006479731B1

(12) United States Patent
Valent et al.

(10) Patent No.: US 6,479,731 B1
(45) Date of Patent: Nov. 12, 2002

(54) PI-TA GENE CONFERRING FUNGAL DISEASE RESISTANCE TO PLANTS

(75) Inventors: Barbara Sue Valent; Gregory T. Bryan, both of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/336,946

(22) Filed: Jun. 21, 1999

Related U.S. Application Data
(60) Provisional application No. 60/095,229, filed on Aug. 4, 1998, now abandoned.

(51) Int. Cl.$^7$ .......................... C12N 15/29; C12N 15/82; C12N 15/90; A01H 5/00; A01H 5/10
(52) U.S. Cl. ..................... 800/279; 435/320.1; 435/468; 536/23.6; 536/23.74; 800/298; 800/320.2
(58) Field of Search .............................. 435/69.1, 320.1, 435/410, 412, 419, 468; 536/23.6, 23.74; 800/278, 295, 298, 320, 320.1, 320.2, 320.3, 301, 279

(56) References Cited

U.S. PATENT DOCUMENTS

| | | | |
|---|---|---|---|
| 5,571,706 A | 11/1996 | Baker et al. ................. | 435/468 |
| 5,648,599 A | 7/1997 | Tanksley et al. ............ | 800/279 |
| 5,674,993 A | 10/1997 | Kawaski et al. ............ | 536/23.6 |
| 5,859,339 A | 1/1999 | Ronald et al. ............... | 800/279 |
| 5,859,351 A | 1/1999 | Staskawicz et al. ........ | 800/301 |
| 5,866,776 A | 2/1999 | Marie de Wit .............. | 800/279 |
| 5,981,730 A | 11/1999 | Ausubel et al. ........... | 536/24.33 |
| 6,127,607 A | 10/2000 | Ausubel et al. ............. | 800/301 |

FOREIGN PATENT DOCUMENTS

| | | | |
|---|---|---|---|
| FR | 2 708 614 | 2/1995 | ............ C07H/21/00 |
| WO | WO 91/15585 | 10/1991 | ............ C12N/15/31 |
| WO | WO 95/18230 | 7/1995 | ............ C12N/15/29 |
| WO | WO 95/28423 | 10/1995 | ......... C07K/14/415 |

OTHER PUBLICATIONS

Jones, D.A. et al., The Role of Leucine–Rich Repeat Proteins in Plant Defences, *Adv. Bot. Res. Incorp. Adv. Plant Pathol.*, 24, 89–167, 1997.
Inukai, T. et al., Allelism of Blast Resistance Genes in Near–Isogenic Lines of Rice, *Phytopathology*, 84(11), 1278–1283, 1994.
Causse, Mathilde A. et al., Saturated Molecular Map of the Rice Genome Based on an Interspecific Backcross Population, *Genetics*, 138, 1251–1274, 1994.
Sweigard, James A. et al., Identification, Cloning, and Characterization of PWL2, a Gene for Host Species Specificity in the Rice Blast Fungus, *The Plant Cell*, 7, 1221–1233, Aug. 1995.

Salmeron John M. et al., Tomato Prf Is a Member of the Leucine–Rich Repeat Class of Plant Disease Resistance Genes and Lies Embedded within the Pto Kinase Gene Cluster, *Cell*, 86, 123–133, Jul. 12, 1996.
Mindrinos, Michael et al., The A thaliana Disease Resistance Gene RPS2 Encodes a Protein Containing a Nucleotide–Binding Site and Leucine–Rich Repeats, *Cell*, 78, 1089–1099, Sep. 23, 1994.
Whitham, Steve et al., The Product of the Tabacco Mosaic Virus Resistance Gene N: Similarity to Toll and the Interleukin–1 Receptor, *Cell*, 78, 1101–1115, Sep. 23, 1994.
Bent, Andrew F. et al., RPS2 of Arabidopsis thaliana: A Leucine–Rich Repeat Class of Plant Disease Resistance Genes, *Science*, 265, 1856–1860, Sep. 23, 1994.
Grant, Murray R. et al., Structure of the Arabidopsis RPM1 Gene Enabling Dual Specificity Disease Resistance, *Science*, 269, 843–846, Aug. 11, 1995.
Baker, Barbara et al., Signaling in Plant–Microbe Interactions, *Science*, 276, 726–733, May 2, 1997.
Valent, Barbara et al., Magnaporthe grisea Genes for Pathogenicity and Virulence Identified Through a Series of Backcrosses, *Genetics*, 127, 87–101, Jan. 1991.
Rybka, Krystyna et al., High Resolution Mapping of the Indica–Derived Rice Blast Resistance Genes II. Pi–ta$^2$ and Pi–ta and a Consideration of Their Origin, *MPMI*, 10(4), 517–524. 1997.
Nakamura, S. et al., Construction of an 800–kb contig in the near–centromeric region of the rice blast resistance gene Pi–ta$^2$ using a highly representative rice BAC library, *Mol. Gen. Genet.*, 254, 611–620, 1997.
Yu, Y. et al., nbxb0002bG06f CUGI Rice BAC Library Oryza sativa genomic clone nbxb0002M12f, genomic survey sequence, *EMBL Accession No. AQ051536*, Jul. 17, 1998.
Wing, R. A. et al., nbxb0064M07r CUGI Rice BAC Library Oryza sativa genomic clone nbx0064M07r, genomic survey sequence, *EMBL Accession No. AQ365625*, Feb. 4, 1999.
Wing, R.A. et al., nbxb0066B06f CUGI Rice BAC Library Oryza sativa genomic clone nbxb0066B06f, genomic survey sequence, *EMBL Accession NO. AQ395844*, Mar. 15, 1999.
Sasaki, T., et al., Oryza sativa cDNA, partial sequence (C53024_1A), *EMBL Sequence Accession No. AU063103*, May 19, 1999.
Yu, Y. et al., nbxb0091A12r CUGI Rice BAC Library Oryza sativa genomic clone nbxb0091A12r, genomic survey sequence, *EMBL Sequence Accession No. AQ577556*, Jun. 3, 1999.

(List continued on next page.)

*Primary Examiner*—Amy J. Nelson
*Assistant Examiner*—Ashwin D. Mehta

(57) ABSTRACT

The preparation and use of an isolated nucleic acid fragment which confers a Pi-ta resistance gene-mediated defense response in plants against disease caused by fungal pathogens is described. Genes incorporating such nucleic acid fragments either alone or in combination with an AVR-Pita isolated nucleic acid fragment or functionally equivalent subfragments thereof and suitable regulatory sequences can be used to create transgenic plants which can produce a Pi-ta resistance gene-mediated defense response against a variety of fungal pathogens, in particular, the rice blast fungus.

37 Claims, 12 Drawing Sheets

OTHER PUBLICATIONS

Nakamura, S. et al., Construction of an 800–kb contig in the near–centromeric region of the rice blast resistance gene pi–ta$^2$ using a highly representative rice BAC library, *Molecular and General Genetics*, 254, 611–620, 1997 Abstract.

Rybka, Krystyna et al., High resolution mapping of the indica–derived rice blast resistance gene II. Pi–ta–2 and Pi–ta and a consideration of their origin, *Database Biosys Online Biosciences Information Service*, 1997.

Leister, D. et al., Oryza sativa NBS–LRR type resistance protein (rl) gene, partial cds, *EMBL Accession No. AF032688*, Jan. 20, 1998.

Leister, Dario et al., Rapid reorganization of resistance genes homologues in cereal genomes, *Proceedings of the National Academy of Sciences of USA*, 95, 350–375, Jan. 1998.

Ronald, Pamela C., The molecular basis of disease resistance in rice, *Plant Molecular Biology*, 35, 179–186, 1997.

Leister, D. et al., Hordeum vulgare NBS–LRR type resistance protein (b8) mRNA, partial cds, *EMBL Accession No. AF032686*, Jan. 20, 1998.

Sakati, T. et al., Orzya sativa gene for Pib, complete cds, *EMBL Accession No. AB013448*, Mar. 17, 1999.

Database WPI, Derwent Publication, Accession No. 199–296527, Mitsui Gyosai Shokubutsu Bio Kenkyusho, Apr. 13, 1999.

Sweigard, James A. et al. Identification, Cloning, and Characterization of PWL2, a Gene for Host Species Specificity in the Rice Blast Fungus, *The Plant Cell*, 7, 1221–1233, Aug. 1995.

Smith, J. R. et al., Mapping of a Magnaporthe grisea locus affecting rice (Oryza sativa) cultivar specificity, *Theoretical and Applied Genetics*, 88, 901–908, 1994.

Farman, Mark L., Chromosome Walking to the AVR1/C039 Avirulence Gene of Magnaporthe grisea: Discrepancy Between the Physical and Genetic Maps, *Genetics*, 150, 1049–1058, Nov. 1998.

Yu, Y. et al. mgxb0013B21r CUGI Rice Blast BAC Library Magnaporthe grisea genomic clone mgxb0013B211r, genomic survey sequence, *EMBL Accessoin No. AQ162565*, Sep. 9, 1998.

Wang, Zi–Xuan et al., The Pib gene for rice blast resistance belongs to the nucleotide binding and leucine–rich repeat class of plant disease resistance genes, *The Plant Journal*, 19(1), 55–64, 1999.

```
  1    ......S....  MAPAVIASQG  VIMRSLTSKL  DSLLLQPPEP  PPPAQPSSLR  KGERKKILLL
 51    RGDLRHLLDD   YYLLVEPPSD  TAPPPDSTAA  CWAKEVRELS  YDVDDFLDEL
101    TTQLLHHRGG   GDGSSTAGAK  KMISSMIARL  RGELNRRRWI  ADEVTLFRAR
151    VKEAIRRHES   YHLGRRTSSS  RPREEDDDDD  CEESAGNERR  RFLLLTFGMD
                                    V....
201    DAAVHGQLVG   RDISMQKLVR  WLADGEPKLK  VASIVGSGGV  GKTTLATEFY
                                                       P-loop
251    RLHGRRLDAP   FDCRAFVRTP  RKPDMTKILT  DMLSQLRPQH  QHQSSDVWEV
301    DRLLETIRTH   LQDKRYFIII  EDLWASSMWD  IVSRGLPDNN  SCSRILITTE
                                 Kinase                 Kinase 3a
                                   2a
351    IEPVALACCG   YNSEHIIKID  PLGDDVSSQL  FFSGVVGQGN  EFPGHLTEVS
401    HDMIKKCGGL   PLAITITARH  FKSQLLDGMQ  QWNHIQKSLT  TSNLKKNPTL
451    QGMRQVLNLI   YNNLPHCLKA  CLLYLSIYKE  DYIIRKANLV  RQWMAEGFIN
```

FIG. 6

```
501  SIENKVMEEV AGNYFDELVG RGLVQPVDVN CKNEVLSCVV HHMVLNFIRC
551  KSIEENFSIT LDHSQTTVRH ADKVRRLSLH FSNAHDTTPL AGLRLSQVRS
601  MAFFGQVKCM PSIADYRLLR VLILCFWADQ EKTSYDLTSI SELLQLRYLK
651  ITGNITVKLP EKIQGLQHLQ TLEADARATA VLLDIVHTQC LLHLRLVLLD
701  LLPHCHRYIF TSIPKWTGKL NNLRILNIAV MQISQDDLDT LKGLGSLTAL
751  SLLVRTAPAQ RIVAANEGFG SLKYFMFVCT APCMTFVEGA MPSVQRLNLR
801  FNANEFKQYD SKETGLEHLV ALAEISARIG GTDDDESNKT EVESALRTAI
851  RKHPTPSTLM VDIQWVDWIF GAEGRDLDED LAQQDDHGYG FFILFPGYNL
901  QGLLSFFLSL PWLLSLPAMH LQPDLMIV
```

FIG. 6 (Continued)

PI-TA GENE CONFERRING FUNGAL DISEASE RESISTANCE TO PLANTS

This application claims priority benefit of U.S. Provisional Application No. 60/095,229 filed Aug. 4, 1998, now abandoned.

FIELD OF THE INVENTION

The invention relates to the preparation and use of an isolated nucleic acid fragment which confers a Pi-ta resistance gene-mediated defense response in plants against disease caused by fungal pathogens. Genes incorporating such nucleic acid fragments either alone or in combination with an AVR-Pita isolated nucleic acid fragment or functionally equivalent subfragments thereof and suitable regulatory sequences can be used to create transgenic plants which can produce a Pi-ta resistance gene-mediated defense response against a variety of fungal pathogens, in particular, the rice blast fungus.

BACKGROUND OF THE INVENTION

Plants can be damaged by a wide variety of pathogenic organisms including viruses, bacteria, fungi and nematodes. The invasion of a plant by a potential pathogen can result in a range of outcomes: the pathogen can successfully proliferate in the host, causing associated disease symptoms, or its growth can be halted by the host defenses. In some plant-pathogen interactions, the visible hallmark of an active defense response is the so-called hypersensitive response (HR). The HR involves rapid necrosis of cells near the site of the infection and may include the formation of a visible brown fleck or lesion. Pathogens which elicit an HR on a given host are said to be avirulent (AVR) on that host, the host is said to be resistant, and the plant-pathogen interaction is said to be incompatible. Strains which proliferate and cause disease on a particular host are said to be virulent, in this case the host is said to be susceptible, and the plant-pathogen interaction is said to be compatible.

Genetic analysis has been used to help elucidate the genetic basis of plant-pathogen recognition for those cases in which a series of strains (races) of a particular fungal or bacterial pathogen are either virulent or avirulent on a series of cultivars of a particular host species. In many such cases, genetic analysis of both the host and the pathogen revealed that many avirulent fungal and bacterial strains differ from virulent ones by the possession of one or more avirulence ("avr" or "AVR") genes that have corresponding "resistance" (R) genes in the host.

This avirulence gene-resistance gene model is termed the "gene-for-gene" model (Crute et al. (1985) pp 197–309 in: Mechanisms of Resistance of Plant Disease. R. S. S. Fraser, ed.; Ellingboe, (1981) Annu. Rev. Phytopathol. 19:125–143; Flor, (1971) Annu. Rev. Phythopathol. 9:275–296). According to a simple formulation of this model, plant resistance genes encode specific receptors for molecular signals generated by avr genes. Signal transduction pathway(s) then carry the signal to a set of target genes that initiate the host defenses. Despite this simple predictive model, the molecular basis of the avr-resistance gene interaction is still unknown.

The first R-gene cloned was the Hm1 gene from corn (*Zea mays*), which confers resistance to specific races of the fungal pathogen *Cochliobolus carbonum* (Johal et al., 1992, Science 258:985–987). Hm1 encodes a reductase that detoxifies a toxin produced by the pathogen. Next to be cloned was the Pto gene from tomato (*Lycopersicon pimpinellifollium*) (Martinet al., 1993, Science 262:1432–1436; U.S. Pat. No. 5,648,599). Pto encodes a serine-threonine protein kinase that confers resistance in tomato to strains of the bacterial pathogen *Pseudomonas syringae* pv. *tomato* that express the avrPto avirulence gene. Taking center stage now are R-genes that encode proteins containing leucine-rich-repeats (LRRs) (Jones and Jones, 1997, Adv. Bot. Res. Incorp. Adv. Plant Pathol. 24:89–167). Two classes of membrane anchored proteins with extracellular LRRs have been identified. One subclass includes R-gene products that lack a cytoplasmic serine/threonine kinase domain such as the tomato Cf-9 gene for resistance to the fungus *Cladosporium fulvum* (Jones et al., 1994, Science 266:789–793, WO95/18230), and the other subclass includes an R-gene product with a cytoplasmic serine/threonine kinase domain, the rice Xa-21 gene for resistance to the bacterial pathogen *Xanthomonas oryzae* (Song et al., 1995, Science 270:1804–1806; U.S. Pat. No. 5,859,339). The largest class of R-genes includes those encoding proteins with cytoplasmic LRRs such as the Arabidopsis R-genes RPS2 (Bent et al., 1994, Science 265:1856–1860; Mindrinos et al., 1994, Cell 78:1089–1099) and RPM1 (Grant et al., 1995, Science 269:843–846). These R-proteins also possess a putative nucleotide binding site (NBS), and either a leucine zipper (LZ) motif or a sequence homologous to the Toll/Interleukin-1receptor (TIR). Table 1 has been reproduced in part from Baker et al. (1997, Science 276:726–733) as a concise summary of classes of R-genes cloned to date and examples of cloned genes within each class.

TABLE 1

Isolated plant resistance genes[1]

| Class | R gene | Plant | Pathogen | Structure |
|---|---|---|---|---|
| 1 | RPS2 | Arabidopsis | *Pseudomonas syringae* pv. Tomato | LZ-NBS-LRR |
| | RPM1 | Arabidopsis | *P. syringae* pv. Maculicola | LZ-NBS-LRR |
| | Prf | Tomato | *P. syringae* pv. Tomato | LZ-NBS-LRR |
| | N | Tobacco | Tobacco mosaic virus | TIR-NBS-LRR |
| | $L^6$ | Flax | *Melampsora lini* | TIR-NBS-LRR |
| | M | Flax | *M. lini* | TIR-NBS-LRR |
| | RPP5 | Arabidopsis | *Peronospora parasitica* | TIR-NBS-LRR |
| | $I_2$ | Tomato | *Fusarium oxysporum* | NBS-LRR |
| 2 | Pto | Tomato | *P. syringae* pv. Tomato | Protein kinase |
| 3 | Cf-9 | Tomato | *Cladosporium fulvum* | LRR-TM |
| | Cf-2 | Tomato | *C. fulvum* | LRR-TM |
| | $HS1^{pro-1}$ | Sugar beet | *Heterodera schachtii* | LRR-TM |
| 4 | Xa21 | Rice | *Xanthomonas oryzae* pv. Oryzae | LRR, protein kinase |
| 5 | Hm1 | Maize | *Cochliobolus carbonum*, race 1 | Toxin reductase |

[1]This Table has been reproduced in part from Baker et al. (1997, Science 276:726–733). References for each of the listed R-genes can be found in this review article.

Nucleotide binding sites (NBS) are found in many families of proteins that are critical for fundamental eukaryotic cellular functions such as cell growth, differentiation, cytoskeletal organization, vesicle transport, and defense. Key examples include the RAS group, adenosine triphosphatases, elongation factors, and heterotrimeric GTP binding proteins called G-proteins (Saraste et al., 1990, Trends in Biochem. Science 15:430). These proteins have in common the ability to bind ATP or GTP (Traut, 1994, Eur. J. Biochem. 229:9–19).

It has long been hypothesized that the rice blast system represented a classical gene-for-gene system as defined by H. H. Flor (Flor, 1971, Annu. Rev. Phytopathol. 19:125–143). Genetic analyses needed to identify AVR-genes in the rice blast pathogen, *Magnaporthe grisea*, has been hampered by the low fertility that typifies *M. grisea* field isolates that infect rice. Genetic crosses between poorly fertile *M. grisea* rice pathogens and highly fertile *M. grisea* pathogens of other grasses (such as weeping lovegrass, *Eragrostis curvula*, and finger millet, *Eleusine coracana*) have provided laboratory strains of the fungus with the level of sexual fertility required for identifying AVR-genes (Valent et al., 1991, Genetics 127:87–101). Rare fertile rice pathogens have since allowed demonstration of a one-to-one genetic or functional correspondence between blast fungus AVR-genes and particular rice R-genes (Silue et al., 1992, Phytopathology 82:577–580).

Interest in the rice blast pathosystem is keen because rice blast disease, caused world-wide by the fungal pathogen *Magnaporthe grisea* (Hebert) Barr (anamorph *Pyricularia grisea Sacc.*), continues as the most explosive and potentially damaging disease of the rice crop despite decades of research towards its control. Manipulation of blast resistance genes remains one of the primary targets in all rice breeding programs, as fungal populations evolve to defeat deployed resistance strategies (See The Rice Blast Disease, 1994, ed. Zeigler, Leong and Teng, CAB International, Wallingford).

Commercial fungicide usage to supplement genetic control strategies began around 1915 when rice farmers used inorganic copper-based fungicides (Chapter 29 in The Rice Blast Disease, 1994, ed. Zeigler, Leong and Teng, CAB International, Wallingford). The fungicides used to control blast disease have changed through time, with some compounds, such as the organomercurials used in the 1950s, causing major environmental damage. The control of rice blast with fungicides currently represents a cost of more than $500 million per year to farmers. This expense for blast control is the largest segment of the world rice fungicide market, which totaled $752 million in 1998 (Wood Mackenzie). Expectations are that the disease problems will intensify as the world rice requirements increase by an estimated 1.7% annually between 1990 and 2025 (See The Rice Blast Disease, 1994, ed. Zeigler, Leong and Teng, CAB International, Wallingford). This estimated need for an additional 13 million tons of rough rice per year to feed the growing population must come from intensification of production on decreasing available land. Rice blast disease is favored by agronomic production practices aimed at high yields, and thus the disease will continue, and most likely increase, as a constraint to rice crop yields unless durable genetic resistance against rice blast disease can be engineered into rice. This invention is among one of the first rice blast resistance genes to be cloned, represents a critical first step to the long term goal of engineering durable genetic resistance to rice blast disease.

The fungus *M. grisea* has a large host range including species of different tribes within the grass family, Triticeae (e.g., wheat), Oryzeae (e.g., rice), Clorideae (e.g., finger millet), Paniceae (e.g., pearl millet), Andropogoneae (e.g., Sorghum) and Maydeae (e.g., maize). Molecular analyses have now defined 8 host species-specific subpopulations of *M. grisea*, each with a restricted set of host species specificities (Reviewed by Valent, 1997, The Mycota V, Plant Relationships, Carroll/Tudzynski, eds., Springer-Verlag Berlin Heidelberg pp 37–54). Table 2 gives a current view of pathogen subpopulations according to mitochondrial DNA (mtDNA) type. This view is strongly supported by separate analyses of ribosomal DNA (rDNA) polymorphisms (including both Restriction Fragment Length Polymorphism (RFLP) and Internal Transcribed Spacer (ITS) sequences) and of polymorphisms in both repetitive DNAs and single copy sequences.

The pathogens of rice, wheat, finger millet, barley and corn (mtDNA types Ia–e) appear closely related, while pathogens of Digitaria spp. and Pennisetum spp. (mtDNA types II–IV) are highly divergent from the previous groups and from each other. However, *M. grisea* strains throughout this broad host range can cause significant crop damage. This pathogen has been shown to be the main cause of yield loss of finger millet (*Eleusine coracana*) in Africa, while infections in wheat (*Triticum aestivum*; Urashima et al., 1993, Plant Disease 77:1211–1216) and pearl millet (*Pennisetum glaucum*; Hanna et al., 1989, J. Heredity 80:145–147), although less widespread, can be severe under humid weather conditions. The disease has been documented on barley and corn (See refs. In Urashima et al., 1993, Plant Disease 77:1211–1216).

TABLE 2

Host Specificities Within *Magnaporthe grisea*

| Subpopulation[1] | Defining Host Species[2] | Crops at Risk |
|---|---|---|
| Ia | *Oryza sativa* | Rice, Barley, Corn |
| Ib | *Triticum aestivum* | Wheat, Barley |
| Ie | Eleusine spp. | Finger Millet |
| Ic | Eleusine spp. | Finger Millet |
| IIa | Digitaria spp. | |
| IIb | Digitaria spp. | |
| III | Pennisetum spp. | Pearl Millet |
| IV | Pennisetum spp. | |

[1]Designated by mitochondrial-DNA haplotype.
[2]Pathogenicity to the "Defining Host Species" appears conserved within the subpopulation. Some hosts, such as barley, are infected by members of two or more subpopulations.

Knowledge of pathogenicity and host specificity for plant pathogenic fungi is not as advanced as for bacterial and viral pathogens, and likewise, less is known about the molecular basis of resistance in cereal crop plants than in dicot crops or in dicot model systems such as Arabidopsis (Baker et al., 1997, Science 276:726–733). Sasaki reported the first results on the inheritance of resistance to rice blast disease from studies begun in Japan in 1917 (Sasaki, 1922, Japanese Genetics, Japan 1, 81–85).

Since this time, over 30 R-genes have been defined through extensive genetic analysis worldwide, and many of these blast resistance genes have been mapped to rice chromosomes (See Refs. In Takahashi, 1965, The Rice Blast Disease, Johns Hopkins Press, Baltimore, 303–329; Causse et al., 1994, Genetics 138:1251–1274). These R-genes include 20 major resistance genes and 10 putative quantitative trait loci (QTLs). Kiyosawa has described 13 major resistance genes with 9 of these genes found as multiple alleles at 3 loci; at the Pi-k locus on chromosome 11, 2 at the Pi-z locus on chromosome 6 and 2 at the Pi-ta locus on chromosome 12 (Kiyosawa, 1984, Rice Genetics Newsletter 1:95–97). Recent studies in Japan (Ise, 1992, International Rice Research Newsletter 17:8–9) and at the International Rice Research Institute (IRRI) (Mackill et al., 1992, Phytopathology 82:746–749) have produced near isogenic rice lines (NILs) for use as "differential" rice varieties for determining which resistance genes are effective in controlling individual strains of the fungus. The IRRI NILs, which provide indica differentials for the blast fungus populations in tropical regions, have been analyzed for genetic relationships between their resistance genes and those present in Kiyosawa Differentials (Inukai et al., 1994, Phytopathology 84:1278–1283).

Molecular markers (or "tags") tightly linked to R-genes have utility for efficient introgression and manipulation of those R-genes in breeding programs. By comparing genotypic patterns of near-isogenic lines, their donors, and their recurrent parents, Yu et al. (1987, Phytopathology 77:323–326) were able to identify five restriction fragment length polymorphic (RFLP) markers linked to three blast resistance genes and to map them to rice chromosomes using segregating populations. RFLP markers linked to the R-genes have been reported (Yu et al., 1991, Theor Appl Genet 81:471–476). Molecular cloning of agronomically important R-genes represents a further advance to the ability of researchers to combine R-genes with other input and output traits in key crop varieties.

In the course of the above mentioned investigations on the inheritance of resistance, Sasaki discovered physiological races of the rice blast pathogen by observing that different field isolates of the blast fungus vary in their ability to cause disease on different varieties of rice (Sasaki, 1922, Journal of Plant Protection 9:631–644; Sasaki, 1923, Journal of Plant Protection 10:1–10). Instability, or "breaking down" under field conditions, of major R-gene resistance to the rice blast fungus has resulted in identification of numerous races, or pathotypes, defined according to virulence spectra on differential rice varieties (Chapters 13 and 16 in The Rice Blast Disease, 1994, ed. Zeigler, Leong and Teng, CAB International, Wallingford). Pathogen populations are dynamic in response to deployment of a new resistance gene, sometimes resulting in new races that overcome the resistance gene within one or two years after deployment in the field.

Researchers have not yet characterized in depth an avirulence gene/R-gene pair in the rice blast pathosystem.

U.S. Pat. No. 5,648,599, issued to Tanksley and Martin on Jul. 15, 1997, describes an isolated gene fragment from tomato which encodes the Pto serine/threonine kinase, conferring disease resistance to plants by responding to an avirulence gene in a bacterial plant pathogen.

WO 95/28423, which published on Oct. 26, 1995, describes resistance due to the *Pseudomonas syringae* RPS2 gene family, primers, probes and detection methods. This published international application includes broad claims to genes encoding proteins with particular $NH_2$-terminal motifs, NBS motifs and leucine rich repeats for protecting plants against pathogens. There are some unique features of the Pi-ta protein. The Pi-ta gene product has a unique amino terminus, lacking either the potential leucine zipper motif of the RPS2 gene-product subfamily (Bent et al., 1994, Science 265:1856–1860; Mindrinos et al., 1994, Cell 78:1089–1099) or the Toll/Interleukin-1 receptor homology encoded by the N gene subfamily (Whitman et al., 1994, Cell 78:1101–1115). Most importantly, the carboxy terminal portion of the Pi-ta gene product is leucine rich, but it does not fit the consensus sequences for leucine-rich repeats reported for R-gene products (Jones and Jones, 1997, Adv. Bot. Res. Incorp. Adv. Plant Pathol. 24:89–167).

U.S. Pat. No. 5,571,706, issued to Baker et al. on Nov. 5, 1996, covers plant virus resistance conferred by the N gene.

U.S. Pat. No. 5,859,351, issued to Staskawicz et al. on Jan. 12, 1999, describes the PRF protein and nucleic acid sequence, which is involved in disease resistance in tomato.

U.S. Pat. No. 5,859,339, issued to Ronald et al. on Jan. 12, 1999, describes the first resistance gene cloned from rice, Xa-21, which encodes an integral membrane protein with both LRR and serine/threonine kinase domains, and confers resistance in rice to bacterial blight.

WO 91/15585 which published on Oct. 17, 1991 and U.S. Pat. No. 5,866,776 issued to de Wit et al. on Feb. 2, 1999 describe a method for the protection of plants against pathogens using a combination of a pathogen avirulence gene and a corresponding plant resistance gene.

U.S. Pat. No. 5,674,993 ('993 patent), issued to Kawasaki et al. on Oct. 7, 1997, describes nucleic acid markers that co-segregate with the rice blast resistance genes Pi-b, Pi-ta and Pi-ta$^2$ and the suggestion that rice blast resistance genes could be isolated and cloned by using these nucleic acid markers. However, no nucleotide sequences are provided for any rice blast resistance genes in the '993 patent. It should be noted that a putative sequence for the Pi-b rice blast resistance gene is now available in Genbank (accession number AB013448).

In addition, Kawasaki et al. have also published two papers. The first paper, Rybka et al., MPMI, 10(4):517–524 (1997), is entitled "High Resolution Mapping of the Indica-Derived Rice Blast Resistance Genes. II. Pi-ta$^2$ and Pi-ta and a Consideration of Their Origin." The sequence for the RAPD primer that is set forth at the top of column 2 on page 519 is not the same as the RAPD primer set forth in SEQ ID NO:2 in the '993 patent. The sequence for the primer in the paper is TCCCCAGCCA (SEQ ID NO:75). The sequence for the primer in the '993 patent is TCGCCAGCCA (SEQ ID NO:76). It is not clear which sequence is correct. Notwithstanding this, it is clear that this paper does not set forth any nucleotide sequences for any rice blast genes. The second paper is Nakamura et al., Mol. Gen. Genet. 254:611–62 (1997). This paper describes the construction of an 800-kb contig in the near-centromeric region of the rice blast resistance gene Pi-ta$^2$ using a rice BAC library. Again, no nucleotide sequence for any rice blast genes is disclosed.

Thus, it is believed that no one hereto has cloned and sequenced a Pi-ta resistance gene from rice with demonstrated utility in controlling *Magnaporthe grisea* that would have significant value as crop protection tools for other graminaceous crops as well. Accordingly, the invention described herein represents the first molecular characterization of a Pi-ta avirulence gene/R-gene pair in the rice blast pathosystem.

SUMMARY OF THE INVENTION

This invention relates to an isolated nucleic acid fragment which confers a Pi-ta resistance gene-mediated defense response against diseases caused by fungal pathogens wherein said nucleic acid fragment corresponds substantially to the nucleotide sequence set forth in SEQ ID NOS:1 or 68 or a functionally equivalent subfragment thereof.

In another aspect this invention concerns genes comprising isolated nucleic acid which confers a Pi-ta resistance gene-mediated defense response against diseases caused by fungal pathogens wherein said nucleic acid fragment corresponds substantially to the nucleotide sequence set forth in SEQ ID NOS:1 or 68 or a functionally equivalent subfragment thereof wherein these fragments are operably linked to suitable regulatory sequences.

In still another aspect, this invention concerns a method of conferring Pi-ta resistance gene-mediated defense response in plants against disease caused by a fungal pathogen which comprises introducing into the plant a gene comprising isolated nucleic acid which confers a Pi-ta resistance gene-mediated defense response against diseases caused by fungal pathogens wherein said nucleic acid fragment corresponds substantially to the nucleotide sequence set forth in SEQ ID NOS:1 or 68 or a functionally equivalent subfragment thereof wherein these fragments are operably linked to suitable regulatory sequences.

In an even further aspect, this invention concerns a method of conferring a resistance gene-mediated defense response in plants at the site of infection by a fungal pathogen, comprising transforming the plant with a recombinant expression construct which comprises (1) an isolated nucleic acid fragment which confers a Pi-ta resistance gene-mediated defense response against diseases caused by fungal pathogens wherein said nucleic fragment corresponds substantially to the nucleotide sequence set forth in SEQ ID NOS:1 or 68 or a functionally equivalent subfragment thereof and (2) an AVR-Pita isolated nucleic acid fragment corresponding substantially to the nucleotide sequence set forth in SEQ ID NO:5 or 7 or a functionally equivalent subfragment thereof, wherein said nucleic acid fragments are operably linked to regulatory sequences and further wherein said construct confers a resistance gene-mediated defense response in plants against diseases caused by a fungal pathogen at the site of infection.

This invention also concerns a recombinant expression construct which confers a resistance gene-mediated defense response in plants against diseases caused by a fungal pathogen at the site of infection which comprises (1) an isolated nucleic acid fragment which confers a Pi-ta resistance gene-mediated defense response against diseases caused by fungal pathogens wherein said gene fragment corresponds substantially to the nucleotide sequence set forth in SEQ ID NOS:1 or 68 or a functionally equivalent subfragment thereof and (2) an AVR-Pita isolated nucleic acid fragment corresponding substantially to the nucleotide sequence set forth in SEQ ID NO:5 or 7 or a functionally equivalent subfragment thereof, wherein said nucleic acid fragments are operably linked to regulatory sequences.

Also of interest are plants transformed with such a gene or recombinant expression construct and seeds obtained from such plants.

BIOLOGICAL DEPOSIT

The fungal strain O-137 has been deposited with the American Type Culture Collection (ATCC), 10801 University Boulevard, Manassas, Va. 20110-2209, and bears the following designation, accession number and date of deposit. Fungal strain G-213, a pathogen isolated from *Digitaria smutsii* in Japan, was obtained from the collection of Jean Loup Notteghem, Laboratoire de phytopathologie, Institut de Recherches Agronomiques Tropicales et des Cultures Vivrieres, Centre de Cooperation Internationale en Recherche Agronomique pour le Developpement (CIRAD), BP 5035, 34032 Montpellier Cedex 1, France, and is available under the name JP34. This strain has also been deposited with the ATCC.

| Organism | Accession Number | Date of Deposit |
|---|---|---|
| *M. grisea* O-137 | ATCC 74457 | August 3, 1998 |
| *M. grisea* G-213 | PTA-191 | June 8, 1999 |

BRIEF DESCRIPTION OF THE SEQUENCE LISTINGS AND FIGURES

The invention can be more fully understood from the following detailed description and the Sequence Descriptions which form a part of this application. The Sequence Descriptions contain the three letter codes for amino acids as defined in 37 C.F.R. 1.822 which are incorporated herein by reference. The nucleotide sequences read from 5' to 3'.

SEQ ID NO:1 is the 5757 nucleotide sequence of the genomic clone of the Pi-ta gene from *Oryza sativa* variety Yashiro-mochi.

SEQ ID NO:2 is the predicted protein sequence encoded by the Pi-ta gene set forth in SEQ ID NO:1.

SEQ ID NO:3 is the 5113 nucleotide sequence of the genomic clone of the pi-ta gene from susceptible *Oryza sativa* variety Tsuyuake.

SEQ ID NO:4 is the predicted protein sequence encoded by the pi-ta gene set forth in SEQ ID NO:3.

SEQ ID NO:5 is the 672 nucleotide coding sequence of an AVR-Pita (formerly called AVR2-YAMO) cDNA from *M. grisea* rice pathogen O-137.

SEQ ID NO:6 is the predicted protein sequence encoded by the sequence set forth in SEQ ID NO:5.

SEQ ID NO:7 is the 675 nucleotide coding sequence of an AVR-Pita cDNA from *M. grisea* pathogen G-213 that infects Digitaria species.

SEQ ID NO:8 is the predicted protein sequence encoded by the sequence set forth in SEQ ID NO:7.

SEQ ID NOS:9–24 set forth the sequences of oligonucleotide (RAPD) primers used in the genetic mapping and cloning of the Pi-ta region.

SEQ ID NOS:25–31 are oligonucleotide primers used in PCR amplification of BAC insert ends.

SEQ ID NOS:32 and 33 are PCR primers used to verify the location of RAPD marker SP4B9.

SEQ ID NOS:34–36 are partial sequences obtained from BAC clone RB142E8 which contains a single copy of the Pi-ta candidate gene PRG2.

SEQ ID NOS:37–64 are sequencing primers used in the full sequencing of the genomic clone for Pi-ta (PRG2) set forth in SEQ ID NO:1.

SEQ ID NO:65 is an oligonucleotide primer used to obtain a Pi-ta nucleic acid fragment.

SEQ ID NOS:66 and 67 are PCR primers used to amplify AVR-Pita$_{176}$ an AVR-Pita nucleic acid fragment that directly encodes the putative mature protease.

SEQ ID NO:68 is the 5222 nucleotide sequence of an EcoRI-HindIII fragment that contains 2425 bp of the native Pi-ta promoter (nucleotides 1 to 2425) and Pi-ta cDNA (nucleotides 2426-5212).

SEQ ID NOS:69 and 70 are oligonucleotide primers used to generate a linker fragment in constructing pML135.

SEQ ID NOS:71 and 72 are PCR primers used to amplify the Adh1–6 intron from maize genomic DNA.

SEQ ID NOS:73 and 74 are PCR primers used to amplify the AVR-Pita nucleic acid fragment (SEQ ID NO:5) in the process of constructing pAVR3.

A. Each of 1440 RAPD primers was tested for identification of polymorphisms linked to the R-gene derived from the rice variety Yashiro-mochi. This Figure shows the linkage map produced using sixteen primers that identified polymorphic DNA fragments segregating with the R-gene in 119 members of the doubled-haploid (DH) population. The most likely order of markers (as defined by the computer program Mapmaker, version2) is given, with the distance between markers shown in centimorgans (cM) on the left. Note that the map is not drawn to scale. Markers SP7C3, SP7H8 and SP8C6 showed no recombination with the R-gene in this population, while markers SP8B8 and SP3G6 mapped to distal ends of the linkage group.

B. Linkage map resolution was increased by testing the 16 markers on an additional 151 DH lines and on 720 F2 progeny. In the larger total population of 990 individuals, markers SP7C3, SP7H8 and SP8C6 again showed no recombination with the R-gene. However, this analysis resolved flanking markers that were previously clustered. The markers SP4B9 and SP9F3 most immediately flank the R-gene region.

Figure 2:
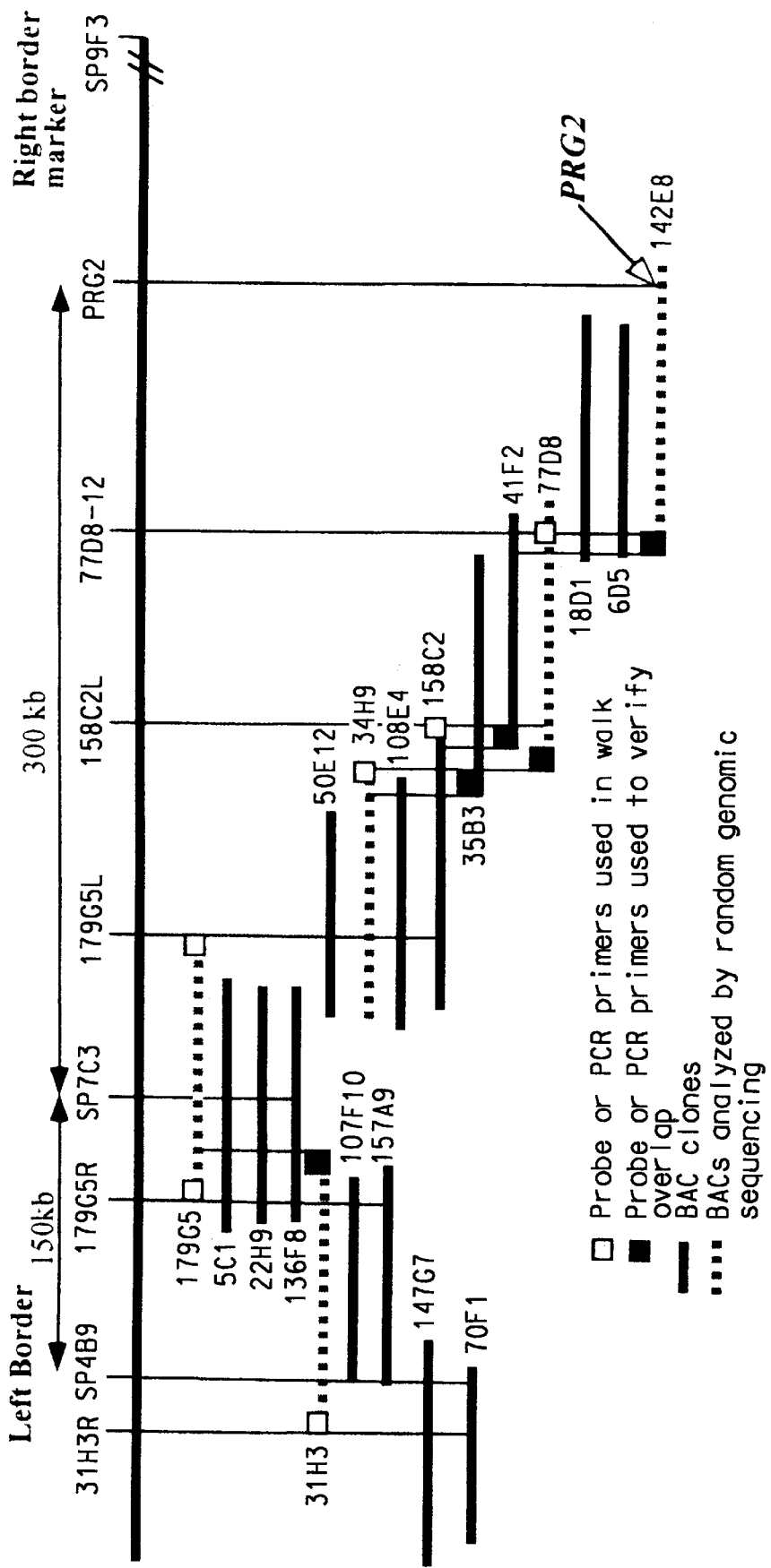

FIG. 2. Positional cloning of Pi-ta. Chromosome walking experiments were begun with the single copy polymorphic sequence originally identified with RAPD marker SP7C3. One step to the left identified one recombination border, that is BAC clones containing the marker SP4B9, which was separated from the R-gene by a recombination event in the F2 progeny line K25. Open boxes indicate locations of the BAC probes used to identify overlapping BAC clones, and black boxes indicate probes used to verify the overlaps. BAC clones that were analyzed by random genomic sequencing are indicated by the broken lines. The Pi-ta gene candidate (PRG2), as well as the DNA markers from 179G5R through 77D8–12 (shown above the line representing the genome region), failed to recombine with the marker SP7C3 and the phenotypically-defined R-gene (determined by infection assays) in members of the rice mapping population. Marker SP9F3 that defines the right border showed recombination with the R-gene in one DH line, YT171.

Figure 3:
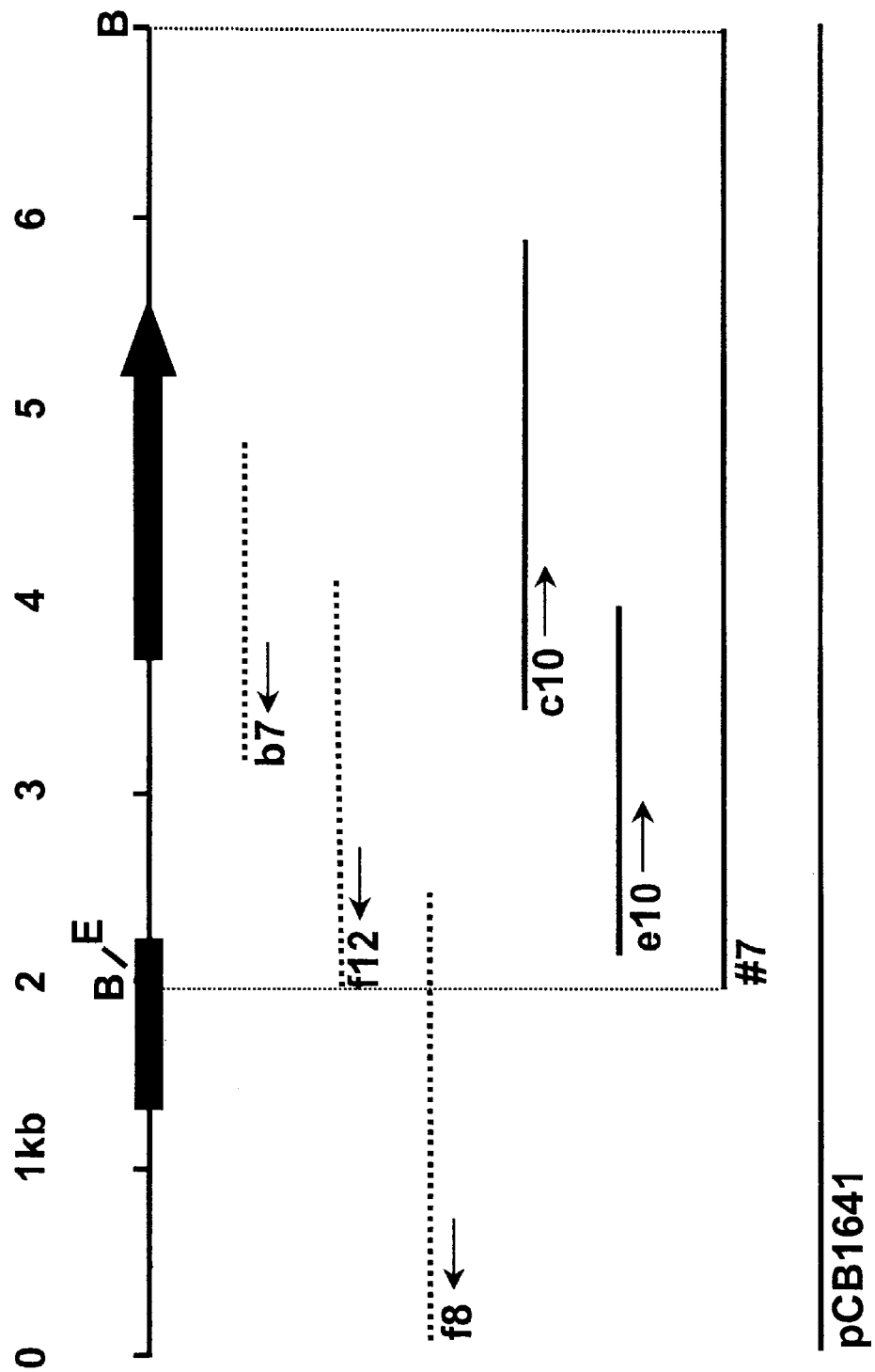
Figure 4A:
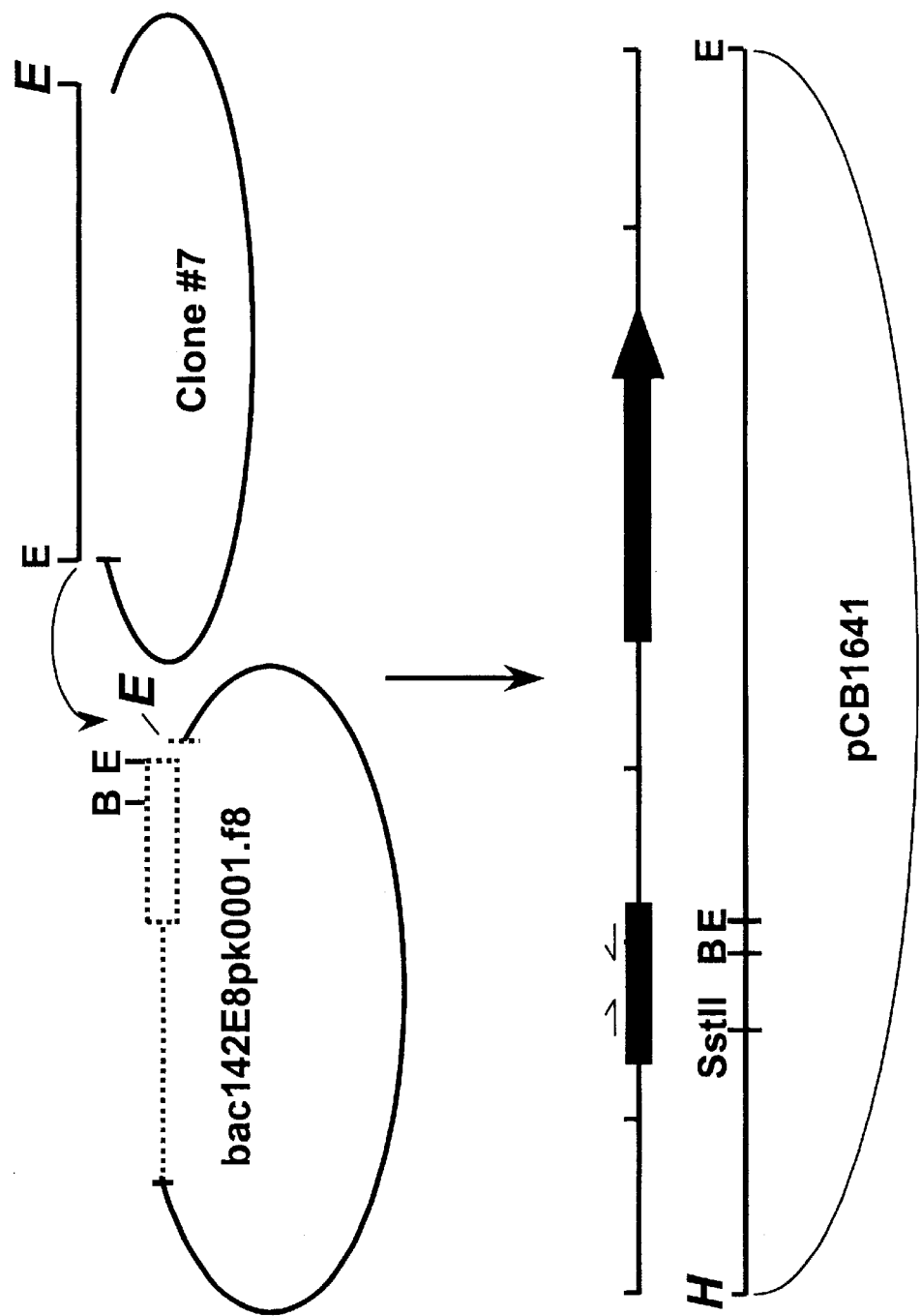

FIG. 3. Restriction map of the R-gene showing the locations of the first three subclones obtained (dotted lines) through random genomic sequencing of BAC RB142E8. These were bac142e8.pk0001.f12 (f12; SEQ ID NO:34), bac 142e8.pk0001.b7 (b7; SEQ ID NO:35), and bac142e8.pk0001.f8 (f8; SEQ ID NO:36). Subsequent sequencing identified overlapping subclones bac142e8.pk0001.e10 (e10), and bac142 e8.pk0005.c10 (c10) from the "no hits class". A 5.3 kb fragment from the BAC RB142E8 (#7) was subcloned into plasmid bac142e8.pk0001.f8 to give pCB1641 containing the entire R-gene as described in FIG. 4A. On the topmost line, the two thick black bars indicate the Pi-ta coding sequence, with the intervening thin black line representing the single intron in the gene, and the arrow representing direction of gene transcription. Restriction sites included are BamHI (B) and EcoRI (E).

FIG. 4. Construction of plasmids pCB 1641 and pCB 1645. Restriction sites included are BamHI (B), EcoRI (E), HindIII (H), SstII and SalI. Italicized restriction sites (E,SalI) are from the vector and not from the rice genomic sequence.

A. Plasmid pCB1641, containing the genomic full length PRG2 coding sequence with 1255 bp of promoter sequence, a 1463 bp intron and 2 kb of 3' untranslated sequence, was constructed by ligating the 5.3 kb EcoRI rice genomic fragment from Clone #7 in place of the (201 bp) EcoRI fragment from the 2.2 kb rice DNA insert in bac142e8.pk0001.f8.

B. Plasmid pCB 1645 containing the 3'1028 bp of the PRG2 coding sequence (positions 4477–5505) was constructed by amplifying this region from plasmid pCB1641 by PCR using primers GB46 (SEQ ID NO: 63) and GB47 (SEQ ID NO: 64). These primers contained restriction sites for SalI and EcoRI respectively. The PCR fragment was digested with SalI and EcoRI and cloned into the corresponding sites of pGAL4-AD (Stratagene).

Figure 5:
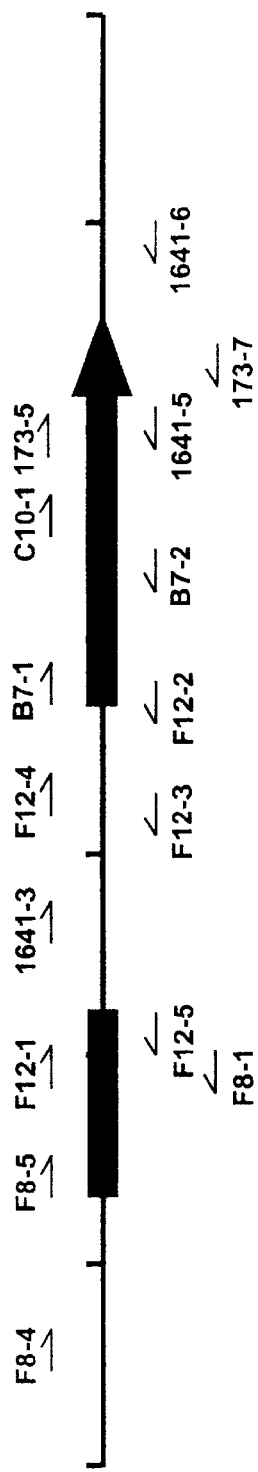

FIG. 5. Relative primer locations in the PRG2 nucleic acid fragment contained in plasmid pCB 1641. These primers were used to amplify genomic DNA fragments from resistant and sensitive rice varieties and for DNA sequencing.

FIG. 6. Deduced Pi-ta protein sequence. Five amino acid differences found in sensitive variants are indicated above the R-protein sequence (SEQ ID NO:2). Features of the R-protein discussed in the text are underlined: the P-loop domain between amino acids 236 and 244, a kinase 2a domain between amino acids 314 and 323, a kinase 3a domain between amino acids 342 to 353, a hydrophobic domain between amino acids 407 to 415. Four potential N-glycosylation sites at positions 339, 556, 654 and 838 are marked with a double underline.

Figure 7:
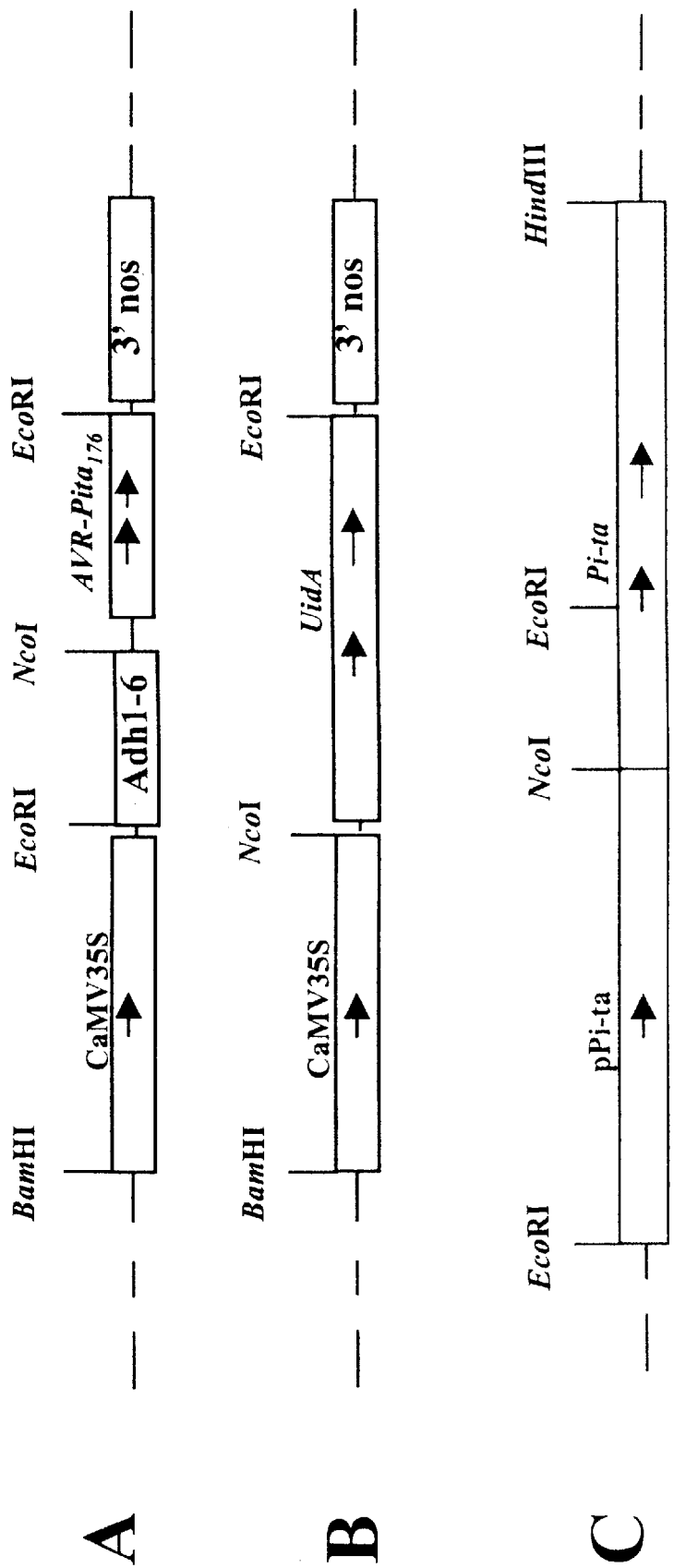

FIG. 7. Diagram of constructs in plasmids pCB1947, pML63 and pCB1926.

A. pCB1947 contains a construct of the AVR-Pita ioslated nucleic acid fragment (formerly called AVR2-YAMO) engineered to encode directly the putative mature protease for the transient expression experiments. This processed form of the isolated nucleic acid fragment, designated AVR-Pita$_{176}$, encodes a polypeptide comprised of amino acids 48 to 223 as set forth in SEQ ID NO:6. An initiation methionine was added to the construct through the NcoI site used in the cloning process. The AVR-Pita coding sequence was first amplified by PCR using primers YL30 (SEQ ID NO:66) containing an in-frame NcoI site and YL37 (SEQ ID NO:67) containing a KpnI site, and cloned into the NcoI-KpnI site of pML 142, resulting in vector pCB 1947. The maize Adh1–6 intron inserted downstream of the 35S promoter results in enhanced expression in monocots. This intron is described in Mascarenhas D. et al. (1990) Plant Mol Biol. 15:913–920.

B. pML63 contains the uidA gene (which encodes the GUS enzyme) operably linked to the CaMV35S promoter and 3' NOS sequence. pML63 is modified from pMH40 to produce a minimal 3' NOS terminator fragment. pMH 40 is described in WO 98/16650 which published on Apr. 23, 1998, the disclosure of which are hereby incorporated by reference. Using standard techniques familiar to those skilled in the art, the 770 base pair terminator sequence contained in pMH40 was replaced with a new 3' NOS terminator sequence comprising nucleotides 1277 to 1556 of the sequence published by Depicker et al. (1982, J. Appl. Genet. 1:561–574).

C. pCB1926 contains the Pi-ta cDNA construct that was created by first amplifying a 2.1 kb partial Pi-ta cDNA nucleic acid fragment from first strand cDNA using primers F12-1 (SEQ ID NO:44) and GB67 (SEQ ID NO:65). A synthetic full-length cDNA was generated by incorporating a 706 bp NcoI-BamHI fragment containing the 5' end of the genomic Pi-ta gene from pCB1641, resulting in plasmid pCB1906. A 3.1 kb EcoRI fragment from pCB 1649 containing 2425 bp of the native Pi-ta promoter sequences (pPi-ta) and 736 bp of the 5' Pi-ta coding sequence was then inserted into the EcoRI sites of pCB1906 to replace the 736 bp 5' end of the synthetic cDNA nucleic acid fragment, producing pCB1926.

Figure 8:
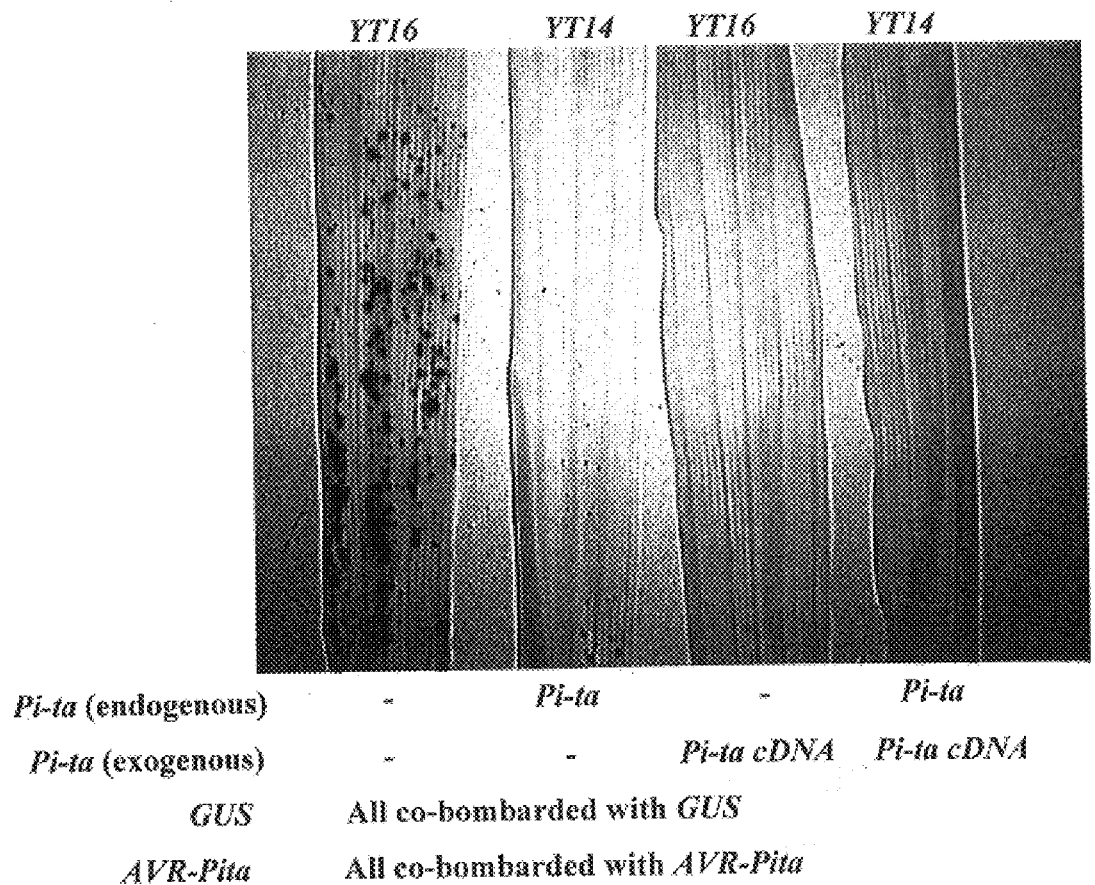

FIG. 8. Particle bombardment transient assay for Pi-ta function in rice plants. These rice leaves show the results of biolistic transient expression of GUS and the Pi-ta and AVR-Pita cDNAs in rice using the constructs in FIG. 7. All seedlings were co-bombarded with 35S::GUS (pML63) and 35S/adh::AVR-Pita (pCB 1947). Leaves 3 and 4 were taken from seedlings that were also bombarded with the Pi-ta cDNA under the control of the native 2.425 kb Pi ta promoter (pCB 1926). Presence (Pi-ta) or absence (−) of the endogenous Pi-ta gene in rice varieties YT14 and YT16 is indicated. GUS expression is indicated by the presence of dark spots in the leaf in the Figure, which are most prominent in the leftmost leaf. The absence of blue GUS staining was used as an indicator of the HR resistance response. The cloned PRG2 candidate nucleic acid fragment substitutes for the endogenous Pi-ta gene in this assay. YT14 and YT16 indicate the source of the rice leaves; both are DH rice lines, but YT14 contains an endogenous Pi-ta nucleic acid fragment while YT16 does not.

Figure 4B:
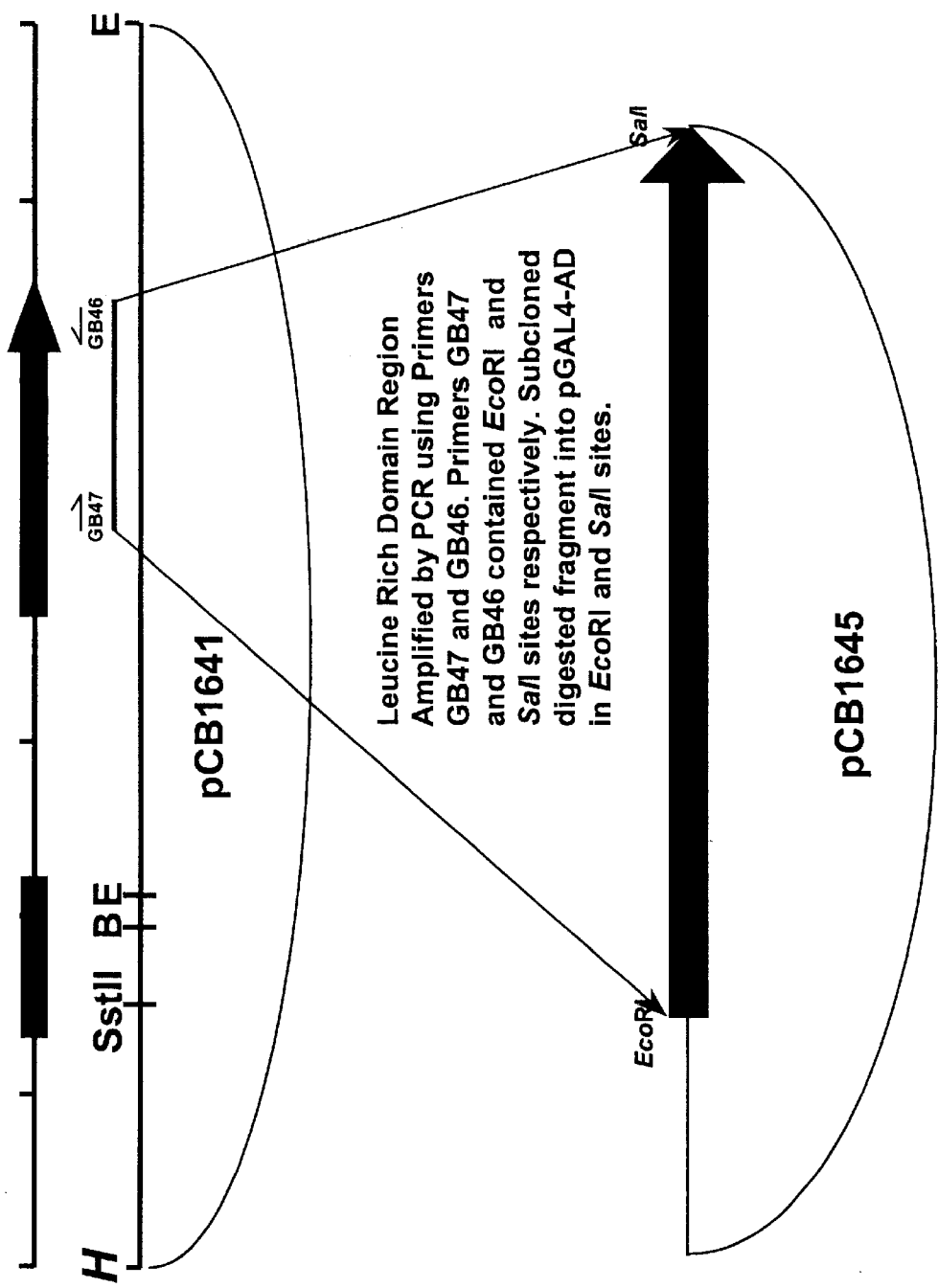
Figure 9:
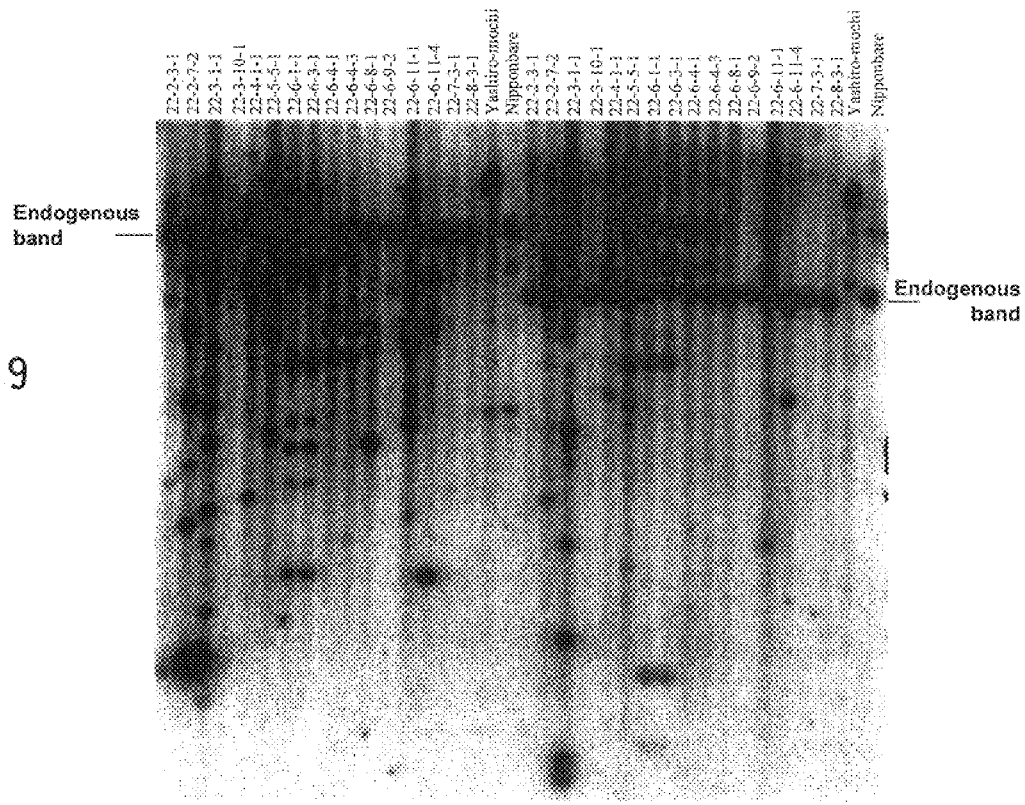

FIG. 9. DNA gel blot analysis on primary transformants to determine presence of the intact Pi-ta nucleic acid fragment. Genomic DNA was digested with EcoRI (left hand side of blot) or EcoRV (right hand side of blot) and probed with 1028 bp EcoRI-SalI 3' end fragment of the Pi-ta nucleic acid fragment cloned in plasmid pCB 1645 (FIG. 4B). The bands corresponding to the endogenous susceptible pi-ta allele in the Nipponbare transformants and non-transformed Nipponbare parent are indicated. All additional bands represent copies of the Pi-ta nucleic acid fragment from plasmid pCB 1641. Primary transformants 22-6-1-1, 22-6-3-1 and 22-6-11-4 are resistant while 22-2-7-2, 22-3-1-1 and 22-4-1-1 are intermediate resistant.

Figure 10:
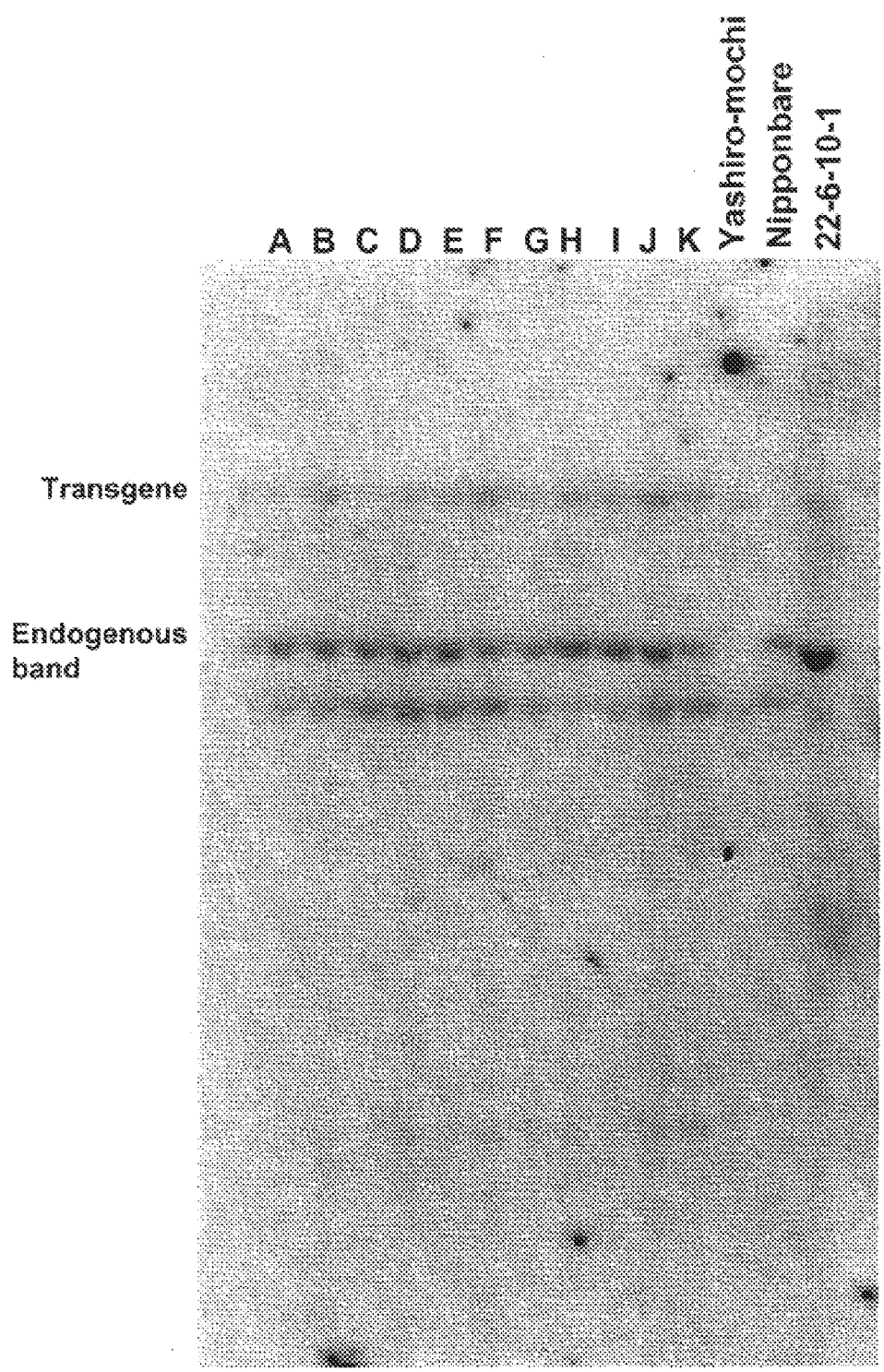

FIG. 10. DNA gel blot analysis of 11 hygromycin resistant R1 individuals from the intermediate resistant primary transformant 22-6-10-1 to determine presence of the intact Pi-ta nucleic acid fragment. Genomic DNA was digested with EcoRV and probed with 860 bp EcoRV-HindIII 3' end fragment of the Pi-ta nucleic acid fragment isolated from plasmid pCB1926. The band corresponding to the endogenous susceptible pi-ta allele in the Nipponbare transformants and non-transformed Nipponbare parent is indicated. The additional upper band represents a copy of the Pi-ta nucleic acid fragment from plasmid pCB 1641. The R0 primary transformant 22-6-10-1 (lane 14) has the same RFLP as the 11 R1 progeny (A-K). The poor DNA quality from this plant resulted in distorted and uneven bands in lane 14 on the Southern blot. All 11 R1 progeny contain the same RFLP, and are intermediate disease resistant indicating stable inheritance of the Pi-ta nucleic acid fragment and the disease resistance phenotype.

DETAILED DESCRIPTION OF THE INVENTION

In the context of this disclosure, a number of terms shall be utilized.

The term "disease resistance gene" means a gene encoding a polypeptide capable of triggering a defense response in a plant cell or plant tissue. The terms "disease resistance gene", "resistance (R) gene" and "R" gene are used interchangeably herein. The resistance that results from a defense response can take several forms. For example, in some genetic backgrounds resistance may take the form of no visible symptoms on inoculated plant tissue, and in others resistance may include small brown spots from which the fungus does not sporulate and does not reinitiate infection. In both cases, the fungal pathogen does not complete its life cycle and disease development is stopped. In some cases disease resistance may take the form of smaller-sized lesions that do not produce the quantity of fungal spores typical of the full disease.

A "defense response" is a specific defensive reaction produced by a host, e.g., a plant, to combat the presence of an infectious agent or pathogen.

A "Pi-ta resistance gene" is a disease resistance gene encoding a polypeptide capable of triggering a defense response in a plant cell or plant tissue against a fungal pathogen such as *Magnaporthe grisea*.

The term "Pi-ta resistance gene mediated defense response" means a defense response due to the production of the polypeptide encoded by the Pi-ta resistance gene and elicited by the presence of a fungal pathogen.

An "AVR-Pita isolated nucleic acid fragment" is a nucleic acid fragment isolated from a pathogen wherein the nucleic acid fragment encodes a polypeptide whose direct or indirect interaction with the Pi-ta resistance protein is responsible for triggering the Pi-ta resistance gene mediated defense response.

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS*. 5:151–153) with the default parameters (GAP PENALTY=10, GAP LENGTH PENALTY=10). Default parameters for pairwise alignments and calculation of percent identiy of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY= 10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' noncoding sequences), within, or downstream (3' non-coding sequences) of a coding sequence, and which influence the transcription, RNA processing or stability, or translation of the associated coding sequence. Such sequences can be native or non-native. Regulatory sequences may include, but are not limited to, promoters, translation leader sequences, introns, and polyadenylation recognition sequences.

"Pathogen" refers to an organism or an infectious agent whose infection around or inside the cells of viable plant tissue elicits a disease response.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the klenow fragment of DNA polymerase I. "Sense" RNA refers to RNA transcript that includes the mRNA and so can be translated into protein within a cell or in vitro. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) Nature (London) 327:70–73; U.S. Pat. No. 4,945,050), or an Agrobacterium-mediated method using an appropriate Ti plasmid containing the transgene (Ishida Y. et al., 1996, Nature Biotech. 14:745–750).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the the target segment are annealed at low temperature and then extended at an intermediate temperature. One set of these three consecutive steps comprises a cycle.

An "expression construct" as used herein comprises any of the isolated nucleic acid fragments of the invention used either alone or in combination with each other as discussed herein and further may be used in conjunction with a vector or a subfragment thereof. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct" and "recombinant expression construct" are used interchangeably herein.

The present invention concerns an isolated nucleic acid fragment which confers a Pi-ta resistance gene-mediated defense response against disease caused by a fungal pathogen wherein said nucleic acid fragment corresponds substantially to the nucleotide sequence set forth in SEQ ID NOS:1 or 68 or a functionally equivalent subfragment thereof.

Also of interest is a gene comprising these isolated nucleic acid fragment(s) operably linked to suitable regulatory sequences, plants comprising such genes in their genome, and seeds of such plants. For example, such a gene could be native or chimeric.

In another aspect, this invention also concerns a method of conferring a Pi-ta resistance gene-mediated defense response against disease caused by a fungal pathogen in plants which comprises introducing into the genome of the plant any of the aforementioned genes.

In still another aspect, this invention concerns a method of conferring a resistance gene-mediated defense response in plants, comprising transforming a plant with a recombinant expression construct which comprises (1) an isolated nucleic acid fragment which confers a Pi-ta resistance gene mediated defense response against diseases caused by fungal pathogens wherein said nucleic acid fragment corresponds substantially to the nucleotide sequence set forth in SEQ ID NOS:1 or 68 or a functionally equivalent subfragment thereof and (2) an AVR-Pita isolated nucleic acid fragment corresponding substantially to the nucleotide sequence set forth in SEQ ID NO:5 or 7 or a functionally equivalent subfragment thereof, wherein said nucleic acid fragments are operably linked to regulatory sequences for expression at the site of infection and further wherein said construct confers a resistance gene-mediated defense response in plants against diseases caused by a fungal pathogen at the site of infection.

In still an even further aspect, this invention concerns a recombinant expression construct which confers a resistance gene-mediated defense response in plants against diseases caused by a fungal pathogen at the site of infection which comprises (1) an isolated nucleic acid fragment which confers a Pi-ta resistance gene mediated defense response against diseases caused by fungal pathogens wherein said nucleic acid fragment corresponds substantially to the nucleotide sequence set forth in SEQ ID NOS:1 or 68 or a functionally equivalent subfragment thereof and (2) an AVR-Pita isolated nucleic acid fragment corresponding substantially to the nucleotide sequence set forth in SEQ ID NO:5 or 7 or a functionally equivalent subfragment thereof, wherein said nucleic acid fragments are operably linked to regulatory sequences. Also of interest are plants transformed with such an expression construct and seeds obtained from such transformed plants.

Cloned R-genes can be used to facilitate the construction of crop plants that are resistant to pathogens. In particular, transformation technology can be used to stack multiple single genes into an agronomic germplasm without linked genomic sequences that accompany genes transferred by classical breeding techniques. Cloned R-genes also can be used to overcome the inability to transfer disease resistance genes between plant species by classical breeding.

The present invention provides an isolated nucleic acid fragment that has utility in controlling rice blast disease, caused by the fungus *Magnaporthe grisea*, in rice. The isolated nucleic acid fragments of the invention are effective when the pathogen comprises an AVR-Pita isolated nucleic acid fragment corresponding substantially to the nucleotide sequence set forth in SEQ ID NOS:5 or 7 or a functionally equivalent subfragment thereof. Alternatively, the isolated nucleic acid fragments of the invention which confer a Pi-ta resistance gene mediated defense response against diseases caused by fungal pathogens are effective when the AVR-Pita avirulence nucleic acid fragment corresponding substantially to the nucleotide sequence set forth in SEQ ID NOS:5 or 7 or a functionally equivalent subfragment thereof, are introduced into the genome of a host plant as a foreign nucleic acid fragment operably linked to a promoter that expresses the AVR-Pita nucleic acid fragment at the site of infection.

As discussed below, other subpopulations of *M. grisea* possess AVR-genes that are homologous to that contained in strains that elicit the Pi-ta specific defense response in rice. Demonstrations that AVR-genes which trigger a Pi-ta-resistance gene-mediated defense response can be present in *M. grisea* rice pathogens in subpopulation 1, in Digitaria pathogens in subpopulation II, and in Pennisetum pathogens in subpopulation III, support broad utility for this gene in controlling *M. grisea* on the range of graminaceous hosts infected by this fungus.

Thus, it is believed that the isolated nucleic acid fragments of the invention will have utility in controlling diseases caused by *M. grisea* on other cereal crops including, but not limited to, wheat, barley, corn, finger millet, and pearl millet.

The rice Pi-ta resistance nucleic acid fragment was cloned by a map-based cloning strategy that is familiar to those skilled in the art as is discussed below. It is shown that introduction of the cloned Pi-ta nucleic acid fragment into susceptible rice confers resistance to pathogen strains in a manner consistent with that expected for the Pi-ta resistance nucleic acid fragment.

The Pi-ta resistance gene product has a novel structure compared to all known classes of resistance gene products. The Pi-ta protein bears no resemblance to the class of membrane anchored proteins with extracellular LRRs. Although the Pi-ta gene product has some features in common with R-gene products with cytoplasmic LRRs such as the Arabidopsis R-genes RPS2 (Bent et al., 1994, Science 265:1856–1860; Mindrinos et al., 1994, Cell 78:1089–1099) and RPM1 (Grant et al., 1995, Science 269:843–846), it lacks the LRR structure characteristic of this class of R-gene products. The Pi-ta protein also lacks either a leucine zipper motif or a Toll/Interleukin-1 receptor motif that further subdivides the cytoplasmic LRR class of R-gene products (Jones and Jones, 1997, Adv. Bot. Res. Incorp. Adv. Plant Pathol. 24:89–167). Thus, the Pi-ta resistance gene product falls into a different class from any other R-gene product currently identified.

Japonica rice varieties Yashiro-mochi (Yamada et al., 1976, Ann. Phytopath. Soc. Japan 42:216) and K1 (Kiyosawa, 1984, Rice Genetics Newsletter 1:95) have been designated as differential rice varieties for the blast resistance gene Pi-ta. While the Pi-ta gene in variety K1 was introgressed into the Japonica background from the indica rice variety Tadukan, the origin of Pi-ta in Yashiro-mochi appears to be an upland rice variety called Okaine (Rybka et al., 1997, Mol. Plant Microbe Interact. 10:517–524 and references therein). One other resistance gene derived from variety Tadukan, the Pi-ta$^2$ gene, appeared to be allelic or closely linked to Pi-ta, although the relationship between Pi-ta and Pi-ta$^2$ appears more complex than would be expected for a pair of independent allelic R-genes (Kiyosawa, 1967, Japan. J. Breeding 17:165–172; Kiyosawa, 1971, JARQ 6:73–80). The R-gene named Pi-4(t) in IRRI NIL differential rice varieties is closely linked to, and may indeed be the Pi-ta gene (Inukai et al., 1994, Phytopathology 84:1278–1283). In addition, the chromosome 12 centromeric region with Pi-ta appears to contain other resistance genes, the major R-gene Pi-6(t) (Abadassi et al., 1990, Rice Genetics II, IRRI, Los Banos, the Philippines, 746–748), a blast QTL (Wang et al., 1994, Genetics 136:1421–1434), and virus and insect R-genes.

The genetic cross (cross 4360) that identified the PWL2 gene, an AVR-gene controlling host species specificity on weeping lovegrass (Sweigard et al., 1995, The Plant Cell 7:1221), also segregated for an additional fungal gene that determined the ability of rice pathogens to infect rice variety Yashiro-mochi. This second AVR-gene, AVR-Pita (formerly called AVR2-YAMO for Yashiro-mochi) was inherited from the parental strain, 4224–7–8, and was derived from the Chinese field isolate O-137 (collected in 1985 at the China National Rice Research Institute in Hangzhou). In each of five complete tetrads derived from cross 4360, four of eight ascospore progeny were able to infect Yashiro-mochi and the others were not. Random spore analysis of cross 4360 and subsequent crosses confirmed segregation of AVR-Pita. Avirulent progeny from cross 4360 frequently produced a few fully pathogenic lesions on Yashiro-mochi. It was speculated that these rare lesions might be due to spontaneous mutations occurring at the AVR-Pita locus. Mutants that had lost function of AVR-Pita were isolated as described in Sweigard et al (1995, The Plant Cell 7:1221). These mutants that were now fully virulent toward Yashiro-mochi retained morphological and fertility characteristics as well as the MGR586 DNA fingerprinting profiles of the presumptive parent. The host specificities of the mutants toward rice varieties with other R-genes were unchanged.

Although dominance is not easy to assess for genes in predominantly haploid fungi like *M. grisea*, the occurrence of virulent mutants suggested that the expressed form of this AVR gene functions to stop infection of Yashiro-mochi, as predicted by the gene-for-gene hypothesis. The genetic instability of the AVR-Pita gene aided in its cloning. The AVR-gene was found to cosegregate with a cluster of physical markers including the telomeric repeat sequence at the end of a linkage group in the *M. grisea* RFLP map produced from cross 4360 (Sweigard et al., 1993, Genetic Maps, edited by S. J. O'Brien, Cold Spring Harbor Laboratory, pp 3.112–3.117). Spontaneous mutants that had become virulent on Yashiro-mochi rice showed structural changes in telomeric restriction fragments that mapped with the avirulence gene, suggesting the gene resided within 1 to 2 kb of the tip of the chromosome (Valent and Chumley, 1994, The Rice Blast Disease, edited by Zeigler, Leong and Teng, CAB International, Wallingford). Southern analysis of genomic DNA from wild type avirulent strains and from spontaneous mutants that had acquired deletions at the chromosome end, identified the sizes of the terminal chromosome fragment produced by digestion of genomic DNA with various restriction enzymes. This analysis suggested that the AVR-gene resided within a telomeric 6.5 kb BglII fragment that corresponded to the chromosome end. Cloning of the corresponding telomeric fragment allowed demonstration that it did indeed contain the AVR-Pita gene, which functioned to transform virulent pathogens of rice cultivar Yashiro-mochi into avirulent strains on Yashiro-mochi.

The AVR-Pita nucleic acid fragment of the invention was isolated from the Chinese rice pathogen O-137 encodes a protein with 223 amino acids (SEQ ID NO:5). Amino acids 173–182 form a characteristic motif of a neutral zinc metalloproteinase and natural or in vitro mutation of the motif residues destroys AVR-gene activity, that is, it no longer transforms virulent strains of the pathogen to avirulence on rice variety Yashiro-mochi. The predicted amino acid sequence has low levels of homology to other metalloproteinases characterized from fungi (Genbank Accession numbers L37524 and S16547). The best characterized secreted fungal metalloprotease, NpII from *Aspergillus oryzae*, contains a 175 amino acid prepro-region that precedes a 177 amino acid mature region (Tatsumi et al., 1991, Mol. Gen. Genet. 228:97–103). The predicted AVR-Pita amino acid sequence exhibits 35% homology and 29% identity with NpII, with the most significant homology confined to the mature 177 amino acid form of NpII. In addition, alignment of the amino acid sequences of AVR-Pita and NpII showed conservation of the cysteines involved in disulphide bonds in the mature NpII protein. It was anticipated that the AVR-Pita isolated nucleic acid fragment encodes a preproprotein that is processed to a mature metalloprotease containing 176 amino acids. Based on this prediction, an AVR-Pita$_{176}$ expression construct was engineered to produce directly the putative mature protease for functional analyses.

*M. grisea* rice pathogens do not appear to require an AVR-Pita gene for fitness in the laboratory or under field conditions. For example, the well-characterized Chinese field isolate O-135 (Valent et al., 1991, Genetics 127:87–101), which was collected at the same time as the source strain O-137, lacks homology to this AVR-nucleic acid fragment. Rice pathogens such as O-135 are not currently affected by the Pi-ta mediated defense response because they fail to elicit the response in Pi-ta containing rice.

Functional AVR-Pita nucleic acid fragments have been cloned from *M. grisea* strains that infect host plants other than rice, and are distantly related to rice pathogens in subpopulation Ia, including a Digitaria pathogen (JP34, isolated in Japan) from subpopulation III, and a Pennisetum pathogen (BF 17, isolated in Burkina Faso) from subpopulation IV. The AVR-Pita nucleic acid fragment cloned from the Digitaria pathogen (SEQ ID NO:7, the G-213 AVR sequence) corresponds to a translated amino acid sequence with 87.9% similarity and 84.7% identity to the O-137 AVR-Pita amino acid sequence when compared by the Bestfit algorithm of the University of Wisconsin Computer group package 9.1 (Devereux et al., 1984, Proc Natl Acad Sci USA 12:387–395). The G-213 AVR-Pita (avirulence) nucleic acid fragment has the most divergent sequence identified which retains the ability to transform virulent rice pathogens into avirulent strains that elicit a Pi-ta resistance gene mediated defense response. Conservation of AVR-gene function between distantly related *M. grisea* strains that infect different grass species suggests that a cloned Pi-ta resistance gene will be effective in controlling the blast fungus on its other host plants, in addition to rice.

The present invention also concerns a gene comprising an isolated nucleic acid fragment which confers a Pi-ta resistance gene-mediated defense response against disease caused by a fungal pathogen wherein said nucleic acid fragment corresponds substantially to the nucleotide coding sequence set forth in SEQ ID NOS:1 or 68 or a functionally equivalent subfragment thereof wherein this fragment is operably linked to suitable regulatory sequences. Such a gene can be an isolated native gene or a chimeric gene. A chimeric gene can be constructed using techniques well known to those skilled in the art. For example, a chimeric gene can be made which comprises the coding sequence of the nucleotide sequence of SEQ ID NO:68 operably linked to a native Pi-ta promoter fragment (nucleotides 1 to 2425) as set forth in SEQ ID NO:68.

Transgenic plants can be made which are capable of mounting a Pi-ta resistance gene-mediated defense response against a fungal pathogen. Examples of plants which can be transformed with an isolated native gene or a chimeric gene as described herein include, but are not limited to, monocots. Preferably the monocot is a cereal. Most preferably, the monocot is rice, wheat, barley, corn, finger millet or pearl millet. Seeds of such transgenic plants are also of interest.

Thus, this invention also concerns a method of conferring a Pi-ta resistance gene-mediated defense response against disease caused by a fungal pathogen in plants which comprises introducing into the plant any of the genes of the present invention as described herein. Pi-ta-mediated defenses are generated in the crop plant in response to AVR-Pita avirulence gene expression, either the native AVR-gene as expressed by the fungal pathogen, or a chimeric AVR-transgene expressed by the plant in response to the pathogen.

In another aspect, this invention also concerns a method of conferring a resistance gene-mediated defense response in plants, comprising transforming the plant with a recombinant expression construct which comprises (1) an isolated nucleic acid fragment which confers a Pi-ta resistance gene mediated defense response against diseases caused by fungal pathogens wherein said nucleic acid fragment corresponds substantially to the nucleotide sequence set forth in SEQ ID NOS:1 or 68 or a functionally equivalent subfragment thereof and (2) an AVR-Pita isolated nucleic acid fragment corresponding substantially to the nucleotide sequence set forth in SEQ ID NOS:5 or 7 or a functionally equivalent subfragment thereof, wherein said nucleic acid fragments are operably linked to regulatory sequences and further wherein said expression construct confers a resistance gene-mediated defense response in plants against diseases caused by a fungal pathogen at the site of infection.

In still another, aspect this invention concerns a recombinant expression construct which confers a resistance gene-mediated defense response in plants against diseases caused by a fungal pathogen at the site of infection which comprises (1) an isolated nucleic acid fragment which confers a Pi-ta resistance gene-mediated defense response against diseases caused by fungal pathogens wherein said gene fragment corresponds substantially to the nucleotide sequence set forth in SEQ ID NOS:1 or 68 or a functionally equivalent subfragment thereof and (2) a nucleic acid fragment corresponding substantially to the nucleotide sequence set forth in SEQ ID NO:5 or 7 or a functionally equivalent subfragment thereof, wherein said nucleic acid fragments are operably linked to regulatory sequences.

Also of interest are plants transformed with such a recombinant expression construct and seeds obtained from such plants. Such an expression construct can be prepared using techniques well known to those skilled in the art as is discussed above. Introduction of transgenes into plants, i.e., transformation is well known to those skilled in the art. A preferred method of plant cell transformation is the use of particle-accelerated or "gene gun" transformation technology (Klein et al. (1978) Nature (London) 327:70–73; U.S. Pat. No. 4,945,050). Examples of plants that can be transformed with such recombinant expression constructs include, but are not limited to, monocots. Preferably, the monocot is a cereal. Most preferably, the monocot is rice, wheat, barley, corn, finger millet or pearl millet.

EXAMPLES

The present invention is further defined in the following Examples. From the above discussion and these Examples, one skilled in the art can ascertain the essential characteristics of this invention, and without departing from the spirit and scope thereof, can make various changes and modifications of the invention to adapt it to various usages and conditions.

Unless otherwise stated, all parts and percentages are by weight and degrees are Celsius. Techniques in molecular biology were typically performed as described in Sambrook, J., Fritsch, E. F. and Maniatis, T. 1989. Molecular cloning—A Laboratory Manual, $2^{nd}$ ed. Cold Spring Harbor Laboratory Press, Cold Spring Harbor, N.Y.

Example 1

Pathogen Strain Development for Identification of the Corresponding R-Gene

An avirulent isolate of the pathogen is necessary to identify a host resistance gene, and the use of new pathogen strains may identify resistance genes that have so far escaped detection. Two fungal strains that show virulence (that is, they fail to elicit an R-gene mediated defense response) toward a rice variety with a particular R-gene are considered to lack the corresponding functional AVR-gene. However, although an avirulent strain of the fungus with a corresponding AVR-gene is necessary for identifying a host resistance gene, when two strains are avirulent toward a particular rice variety, they could have the same AVR-gene, or different AVR-genes triggering different R-gene mediated defense responses. Use of new or uncharacterized fungal strains may identify previously unidentified R-genes. This caution is especially required when working with field isolate rice pathogens such as O-137, the source of the AVR-Pita gene. In addition, rice blast infection assays are notoriously sensitive to environmental conditions, especially if the rice varieties have some level of general resistance to blast, or if the pathogens used are unstable in pathogenicity and morphology characteristics. Therefore, the use of thoroughly characterized pathogen strains is key to success.

Multiple pathogen resources, including genetic populations segregating for the AVR-Pita gene, facilitated cloning the R-gene. Progeny strains such as 4360-R-17, 4360-R-27, 4360-R-30, and subsequent generation strain 4375-R-26 (Sweigard et al., 1995, The Plant Cell 7:1221) had improved characteristics for these studies. Because the rice crosses in these experiments had at least two R-genes segregating, Pi-ta and Pi-km, and because pathogen cross 4360 was segregating for AVR-genes corresponding to both known R-genes, there was a need to obtain genetically characterized pathogen strains bearing single AVR-genes. Such strains were needed to identify the effects of individual R-gene/AVR gene interactions on lesion development. There was also the need to maximize phenotypic differences between the resistant and susceptible interactions in order to assure accuracy of scoring the resistance phenotype among the rice progeny in the mapping population. Twenty-eight progeny strains were obtained from cross 4360 that contained AVR-Pita, but which did not contain AVR1-TSUY. It is believed that AVR1-TSUY is the AVR-gene corresponding to the blast resistance gene Pi-km in the japonica variety Tsuyuake. These 28 progeny were screened for stable ability to produce fully susceptible disease symptoms (Type 4–Type 5 lesions) on one parental rice variety, and typical resistance responses (Type 0–Type 1 lesions) on the other rice variety (Valent et al., 1991, Genetics 127:87). M. grisea isolate 4360-R-62 was chosen as a test strain which contained only AVR-Pita. Out of an additional 9 strains screened, 4360-R-67 was chosen as an excellent pathogen that contains only AVR1-TSUY. Most of the R-gene mapping that is described below was done with these two fungal strains.

In addition, mutants that have lost AVR-gene function are useful for comparison to the parental strain from which they were derived. For example, strain CP987 was derived from strain 4360-R-17 by isolation of a spontaneous virulent mutant. The AVR-Pita gene in CP987 was inactivated by a small deletion. Virulent mutants can easily be obtained from avirulent field isolates or laboratory strains as described in Sweigard et al. (1995) The Plant Cell 7:1221. In the opposite direction of pathogen trait alteration, field isolate Guy11, which is virulent on Yashiro-mochi, became avirulent on this host when it was transformed with a cloned AVR-Pita gene to produce strain CP3285. Fungal transformation in the rice blast system is routine, as described in Sweigard et al. (1995) The Plant Cell 7:1221.

Example 2

Plant Infection and Evaluation

Infection assays were performed as previously described (Valent et al., 1991, Genetics 127:87). Conidia were collected from cultures grown on oatmeal agar plates by washing with a sterile 0.25% gelatin solution. Four to five individuals from each rice variety were sown in Metro-Mix® potting medium within plastic pots in a growth chamber. Plants were grown on a day cycle of 14 hours of light, 28 degrees and 70 to 85% relative humidity. Night conditions were 22 degrees and 85% relative humidity. Pots with two-week-old plants were placed into plastic bags in order to maintain 95–100% relative humidity required for pathogen penetration, and inoculated with pathogen strains such as 4360-R-62 or 4360-R-67 described in Example 1. A four ml aqueous suspension, containing 2.5×105 conidia per ml, was sprayed onto the plants using an artist's air brush (Pasha, size 1). The plastic bags containing the inoculated plants were then closed with a twist-tie, and were incubated in low light conditions at room temperature for 24 hours. After 24 hours, the plants were removed from the bags, and were placed back in the growth chamber. Infection types, i.e., lesion symptoms, were scored 7 days after inoculation. A scale of 0–5 was used to classify infection phenotypes (Valent et al., 1991, Genetics 127:87–101). Lesion types of 0 and 1 were scored as resistant while lesion types 3 to 5 were scored as susceptible.

Example 3

Identification and Mapping of the R-gene Corresponding to the Rice Blast AVR-gene Development of Rice Mapping Populations.

Two plant populations were used to identify physical markers linked to the R-gene. First, a doubled-haploid (DH) population was generated for our use at CIAT (Centro Internacional de Agricultura Tropical; Apdo aereo 6713, Cali, Colombia). In order to minimize problems with segregation distortion that are known to occur in crosses between japonica and indica varieties (Wang et al., 1994, Genetics 136:1421–1434), a decision was made to work with a cross between two japonica varieties, Yashiro-mochi (with the R-gene Pi-ta) and Tsuyuake (with the R-gene Pi-km). Although the levels of polymorphism that exist between two japonica varieties are too low for purposes of mapping an entire rice genome, it was reasoned that because the Pi-ta gene originated from indica rice, there would be sufficient polymorphism in this R-gene region to allow mapping of the disease-resistance trait. Bulked segregant analysis of the results of this cross, described below, focused mapping efforts on particular regions of the genome.

Production of DH rice lines was done according to standard technology to those skilled in the art. First, haploid callus was obtained from the pollen of F1 plants derived from reciprocal crosses between rice varieties Yashiro-mochi and Tsuyuake. Rice plants were then regenerated from this callus. Fertile plants derived from this procedure have undergone spontaneous diploidization of the haploid genome. Individual plants from reciprocal crosses were subjected to 7 selfing generations to produce a total of 429 independent DH lines. Of these, 119 lines were used as the initial mapping population in this study.

For fine structure mapping, an F2 population was developed at DuPont by crossing two DH lines, YT4, which contained the active Pi-ta R-gene from variety Yashiro-mochi and YT10, which did not. Techniques for F2 analysis are well known to those skilled in the art.

Segregation Analysis Identified a R-Gene Corresponding to AVR-Pita.

Reactions of 119 DH lines to the two fungal strains 4360-R-62 and 4360-R-67 were as follows: 35 resistant to both strains, 24 resistant to 4360-R-62, 29 resistant to 4360-R-67 and 31 susceptible to both strains. Progeny in these four phenotypic classes fit an expected 1:1:1:1 ratio ($X^2$=2.20; P>0.50) indicating, as expected, that Pi-ta and Pi-km were independently segregating R-genes. An additional 115 DH lines were also inoculated with strain 4360-R-62 alone, of which 62 lines exhibited resistant types and 53 lines exhibited susceptible types. Thus, the total ratio of resistant to susceptible lines with strain 4360-R-62 was 126 to 108, which did not deviate from the expected 1:1 ratio based on chi-square test ($X^2$=1.38, P>0.20).

Analysis of F1 and F2 progeny from the fine structure mapping cross between rice lines YT10 and YT4 further supported the segregation of a dominant R-gene corresponding to the AVR-Pita avirulence gene in the pathogen. Four $F_1$ hybrids were infected with 4360-R-62 in order to determine if the R-gene phenotype was dominant or semi-dominant, as predicted. All the F hybrids exhibited reaction type 0 or type 1, similar to the resistant parent, indicating that the allele for blast resistance was dominant to the allele for susceptibility in rice. Seven hundred twenty $F_2$ progeny were also infected with 4360-R-62. Infection assays for the $F_2$ population were essentially the same as described in Example 2 with exceptions that plants were sown in plastic trays, 60 plants per tray, and inoculum was reduced to 1×10$^5$ conidia per ml. About 30 ml of conidial suspension was applied to each tray. $F_2$ plants segregated as 541 resistant and 179 susceptible which nearly perfectly fit a 3:1 ratio (0.007; P>0.90) indicating a single dominant gene. For use in fine structure mapping studies, the susceptible plants from this analysis were carefully trimmed to remove diseased tissue, and transplanted into fresh potting medium.

RAPD Screening To Identify DNA Markers Linked to the R-Gene.

In order to identify physical markers linked to the R-gene, Random Amplified Polymorphic DNA (RAPD) markers (Williams et al., 1990, Nucleic Acids Research 18:6531–6535) were employed in an early stage of mapping. Polymorphisms, DNA segments that amplify from one parent and not the other, are detected based on amplification of random DNA segments with single primers of arbitrary nucleotide sequence. In order to focus on markers linked to the R-gene, bulked segregant analysis was employed. This is a method of assaying polymorphisms between two pools of individuals, one in which all individuals have the gene of interest and the other in which no individuals have the gene of interest. (Michelmore et al., 1991, Proc Natl Acad Sci USA 88:9828–9832). DNA segments that are not linked appear equally in both pools, while DNA segments that are linked will appear in one pool and not the other. Rice total genomic DNA was isolated from individual DH lines using a method described previously (Dellaporta et al., 1983, Plant Mol. Biol. Reporter 1:19–21). After estimating DNA concentration by electrophoresis in gels vs. standard quantities, aliquots of DNAs from 10 DH lines that were resistant to 4360-R-62 and aliquots of DNAs from 10 DH lines that were susceptible to 4360-R-62 were combined to form two sets of "bulked" DNAs. Bulked DNAs were used as templates to evaluate the amplification of RAPD markers. RAPD reactions were carried out in volumes of 20 $\mu$l, containing 80 mM Tris-HCl (pH 9.0); 20 mM $(NH_4)_2SO_4$; 3.5 mM $MgCl_2$; 100 $\mu$M each of dGTP, dATP, dCTP and dTTP; 0.2 $\mu$M primer; 10 ng of DNA; and 1 unit of Taq DNA polymerase (Perkin Elmer Cetus). The DNA fragments that were amplified with this procedure were separated on 2% agarose (New England BioLabs) gels in 1×TAE buffer for 5 hours. Polymorphic fragments, either present or absent in resistant and susceptible pools, were further confirmed by using DNA templates from both parents, from the resistant and susceptible pools, and from each of the individuals forming the two pools.

The pooled DNAs, either from the resistant or from the susceptible lines, were used as templates to screen 1440 RAPD primers. More than 95 percent of the primers gave rise to one or more amplified products. The average number of discrete bands per primer was approximately 8. From these amplifications, RAPD primers SP1B8, SP2C12, SP3F4, SP3G6, SP4A5, SP4B9, SP6C2, SP6G10, SP7C3, SP7H8, SP8B8, SP8C6, SP8E2, SP8F1, SP9F3 and SP15B12 (SEQ ID NOS: 9–24) identified polymorphisms linked to the R-gene corresponding to AVR-Pita.

| SP1B8: | 5'-TCAGCGCCT-3' | (SEQ ID NO:9) |
| SP2C12: | 5'-CCAATCGGAC-3' | (SEQ ID NO:10) |
| SP3F4: | 5'-TAATGGGCGG-3' | (SEQ ID NO:11) |
| SP3G6: | 5'-GTCGCTACTG-3' | (SEQ ID NO:12) |
| SP4A5: | 5'-ACAGCGCCTT-3' | (SBQ ID NO:13) |
| SP4B9: | 5'-AGGCGTCTTC-3' | (SEQ ID NO:14) |
| SP6C2: | 5'-TAGCCAGACC-3' | (SEQ ID NO:15) |
| SP6G10: | 5'-TCTATGCCCC-3' | (SEQ ID NO:16) |
| SP7C3: | 5'-ATGGCAGATG-3' | (SEQ ID NO:17) |
| SP7H8: | 5'-CGAGTCAACT-3' | (SEQ ID NO:18) |
| SP8B8: | 5'-GTAGAAGCCT-3' | (SEQ ID NO:19) |
| SP8C6: | 5'-TCATGCGGAG-3' | (SEQ ID NO:20) |
| SP8E2: | 5'-CCATTTCCGT-3' | (SBQ ID NO:21) |
| SP8F1: | 5'-GGGAGGACTT-3' | (SEQ ID NO:22) |
| SP9F3: | 5'-AAAGGCAGTG-3' | (SEQ ID NO:23) |
| SP15B12: | 5'-TGTGCAACGG-3' | (SBQ ID NO:24) |

Initial Mapping of Markers Linked to the R-gene.

Segregation of linked RAPD molecular markers were scored for each of 119 individual DH rice lines. Linkage analysis between these RAPD markers and the R-gene was performed with the computer program MAPMAKER (version 2.0) (Konieczny and Ausubel, 1993, The Plant Journal 4:403). A LOD score>3 was used to establish linkage between RAPD markers and the R-gene.

Two-point analysis revealed strong linkage among the identified RAPD markers, and between these markers and the R-gene in the DH population. The order of these markers relative to the R-gene was determined by multiple point analysis. SP7C3, SP7H8 and SP8C6 mapped closest to the R-gene with no recombination observed among the 119 progeny, while SP8B8 and SP3G6 mapped to distal ends of the mapping region, with genetic distances of 8.6 and 7.3 cM from the R-gene, respectively. The most probable order of these markers is presented in FIG. 1A. However, the order of a number of markers could not be determined unambiguously because the probability of any particular order was not greater than 100:1 relative to other alternative orders based on this population size.

Fine Structure Mapping of the R-Gene.

Figure 1:
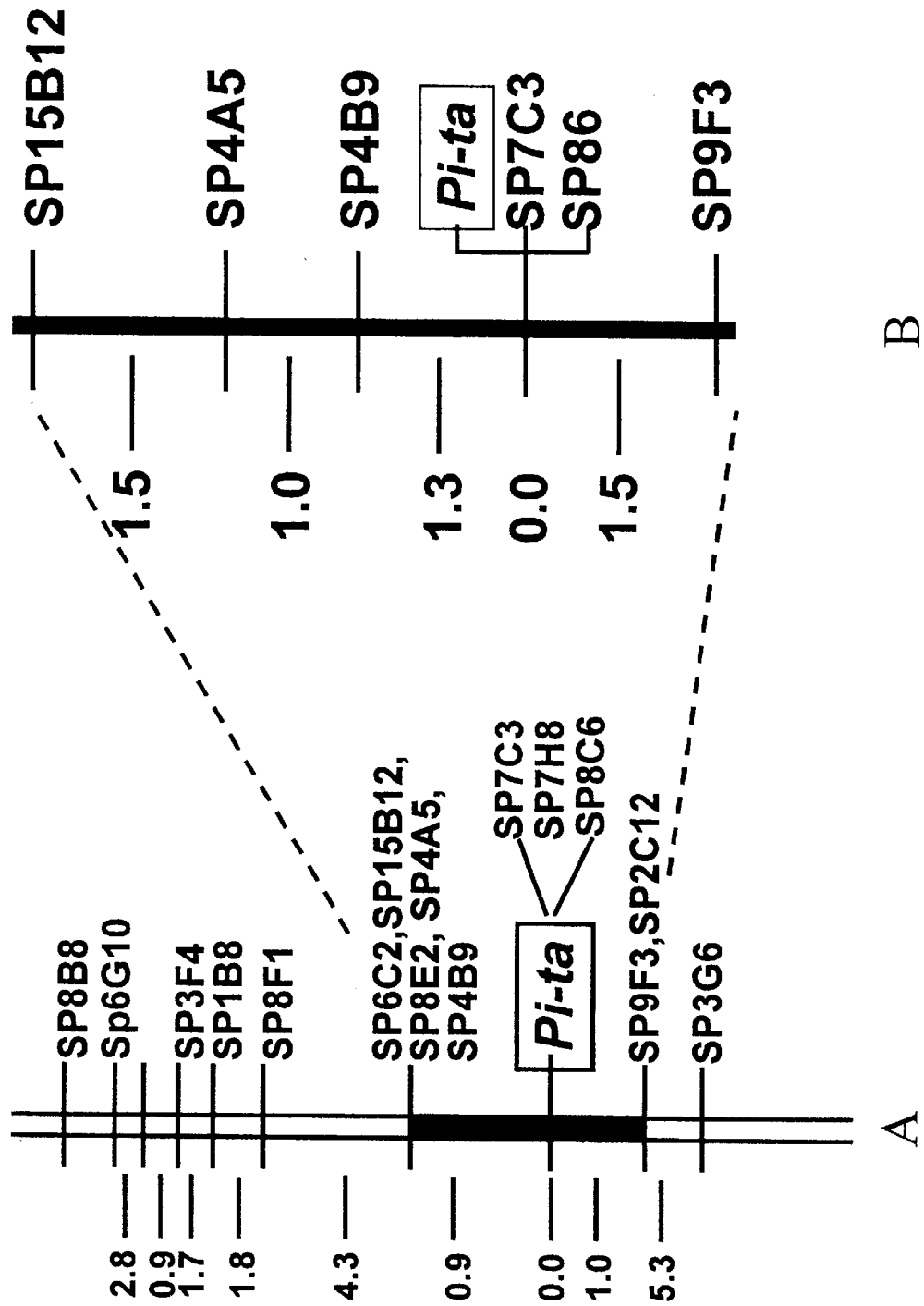
FIGS. 1A–B. Molecular map of the chromosome region containing the R-gene.

Increased mapping resolution was accomplished by scoring the segregation of the R-gene and the linked markers in a larger mapping population. Additional DH rice lines were included to bring the total to 270 lines in the mapping population. In addition, 720 F2 progeny from the genetic cross between DH lines YT4 and YT10 were included in this analysis. As described, 720 F2 plants were inoculated with fungal strain 4360-R-62 (containing only AVR-Pita) to determine which contained the corresponding R-gene. The susceptible plants from this analysis were recovered by removal of diseased tissue and by transplanting to fresh potting medium. As is well understood, F2 segregation analysis of RAPD markers is complicated because the dominance of these markers prevents discrimination between heterozygous and homozygous progeny. This difficulty can be overcome in some cases by isolating codominant markers from the the RAPD markers. For example, isolation of RFLP markers from RAPD markers is described in Example 4. Additional differentiation of heterozygous versus homozygous F2 rice lines was accomplished by checking for segregation of the resistance phenotype in the F3 generation. The fine structure map produced in this study is shown in FIG. 1B.

Example 4

Evidence that the R-gene Recognizing AVR-Pita is Pi-ta

Three lines of evidence were obtained that the R-gene corresponding to the cloned avirulence gene is the blast resistance gene previously identified as Pi-ta.

Mapping of Blast Resistance Genes to Rice Chromosome 12.

A recombinant inbred (RI) population of 192 individuals (prepared by crossing lines LH422 and 9024; Xiao et al., 1995, Genetics 140:745) was used to map the R-gene region to its rice chromosomal location. The R-gene was mapped indirectly using flanking RFLP markers that had been derived from polymorphic RAPD markers. RAPD fragments were eluted from gels, cleaned using Geneclean II (Bio 101, San Diego, Calif.) and subcloned into the TA cloning vector (Invitrogen, San Diego, Calif.). The subcloned DNA inserts were amplified by using T7 (SEQ ID NO:27) and SP6 (SEQ ID NO: 28) promoter primers and used as probes to survey the two parents of the mapping population. Probes P4A5, P1B8, P7C3 and P8C6 showed polymorphisms with restriction enzymes XbaI, EcoRI, EcoRV and DraI, respectively. Allelic patterns for the four RFLP markers were scored for the RI population members and mapped using the MAPMAKER (version 2.0) program. All the markers were placed with a LOD score of greater than 3. Two point analysis established that all these markers were linked to a number of RFLP markers on chromosome 12. Multiple point analysis placed P7C3 and P8G6 in the intervals between RG341 and RZ670 with a genetic distance of 1.3 cM and 3.2 cM respectively (Causse et al., 1994, Genetics 138:1251–1274). Markers P1B8 and P4A5 mapped between RG9 and RG869. Thus the R-gene corresponding to AVR-Pita maps to the same chromosomal region as the Pi-ta gene.

AVR-Pita Mutants and Segregating Progeny Show Identical Specificity Toward Other Rice Varieties Reported to Contain Pi-ta.

Although the R-gene maps to the chromosomal region containing the Pi-ta resistance gene, it might still be an unknown gene or one of the other R-genes mapping to this same region. A series of pathogen strains was identified, including O-137, the Chinese field isolate that is the source of the AVR-Pita gene; 4360-R-17 and 4360-R-27, progeny of cross 4360 that contain the AVR-gene; 4360-R-30, a progeny of cross 4360 that does not contain the AVR-gene; and CP987 and CP983, mutants that have lost AVR-gene function. These isolates of the pathogen were used in infection assays on other rice varieties that contain the Pi-ta gene, specifically, Tadukan and K1. The identical avirulence spectrum shown by these pathogen strains on Yashiro-mochi, K1 and Tadukan (Table 3) suggests that the R-gene corresponding to AVR-Pita is the previously identified gene Pi-ta. The rice variety Sariceltik which lacks the Pi-ta gene is susceptible to all of these strains of the pathogen.

TABLE 3

Lesion Type on Rice Cultivar

| Fungal Strain | AVR-Pita Functional | Sariceltik | Yashiro-mochi | Tadukan | K1 |
|---|---|---|---|---|---|
| 0-137 | Yes | S | R | R | R |
| 4360-R-17 | Yes | S | R | R | R |
| CP987 | no | S | S | S | S |
| CP983 | no | S | S | S | S |
| 4360-R-27 | Yes | S | R | R | R |
| 4360-R-30 | no | S | S | S | S |

S: Susceptible, Lesion Types 3–5
R: Resistant, Lesion Types 0–1

Infections with Japanese Differential Pathogen Strains Confirm the Specificity.

Finally, inoculations were conducted with Japanese pathogen strains Ken60-19, Ken54-20, Ina72, Ina168, Ken54-04 (Kiyosawa, 1976, SABRAO Journal 8:53–67; Yamada et al., 1976, Ann. Phytopath. Soc. Japan 42:216); these strains were used in the identifications of various blast resistance genes in rice, including Pi-ta. These strains were inoculated on DH progeny rice lines and differential rice varieties along with strains 4360-R-62 and 4360-R-67 obtained from this study. All of these field isolates, except Ina168, were avirulent on both differential rice varieties known to contain the Pi-ta R-gene, and DH progeny rice lines that contain the R-gene corresponding to AVR-Pita, thus demonstrating specificity of infection and disease that is consistent with the R-gene being Pi-ta.

Example 5

Construction of a BAC Library

Methods for constructing large insert libraries are now routine for those familiar with the art (Wang et al., 1995, The Plant Journal 7:525). Standard techniques were employed for the construction of a bacterial artificial chromosome (BAC) library using genomic DNA from protoplasts of leaves of the DH rice line YT14 that carries the R-gene. Protoplasts were isolated from young leaves and sheaths as previously described (Wu and Tanksley, 1993, Plant Mol. Biol. 23:243). The DNA was partially digested with HindIII in agarose plugs and fractionated on CHEF gels. DNA fragments ranging from 100 to 150 kb were eluted and subjected to a second size selection to remove small molecules. Size-selected DNA was then recovered from agarose by treating with GELase (Epicentre Tech) and ligated into the HindIII site of pBeloBACII vector (Shizuya et al., 1992, Proc. Natl. Acad. Sci. USA 89:8794). Transformation of *E. coli* DH10B cells was carried out by electroporation using Cell Porator Electroporation System I (BRL). BAC colonies were selected on LB plates with chloramphenicol at 12.5 μg/ml. A total of 20,160 independent colonies were picked and stored in 96-well microtiter plates containing 100 μl LB with chloramphenicol and 10% glycerol. The average insert size of clones in the library is 110 kb based on analysis of 28 randomly selected colonies. The library contains approximately 5 haploid genome equivalents of rice DNA.

Example 6

Chromosome Walking and Identification of Pi-ta R-gene Candidate PRG2

The BAC library, contained in 210 microtiter plates, was spotted onto high density filters using a Biomek robot (Beckman Instruments). The entire library was arrayed onto 14 filters with a density of 16 plates spotted per filter. The set of filters was probed with the single copy RFLP probe, p7C3, obtained from the RAPD marker SP7C3 as described in Example 3. This marker cosegregated with the Pi-ta gene in the entire DH and F2 mapping populations. Four overlapping BAC clones were identified in this hybridization: 5C1, 22H9, 136F8 and 179G5 (See FIG. 2). With these materials and information as a starting point, two methods were used to isolate probes from the ends of the BAC rice inserts, and these probes were used to screen the library filters again. BAC DNAs were isolated using a midi-prep procedure based on standard alkaline lysis plasmid purification methods (Sambrook). The method for isolating the insert border sequences for one side of the vector involved digestion of the DNA with either BamHI or SphI to remove the majority of the insert DNA. The remaining vector was religated and the insert sequences were isolated by PCR with either the M13–20 (SEQ ID NO:25) and reverse (SEQ ID NO:26) primers or the T7 (SEQ ID NO:27) and SP6 (SEQ ID NO:28) primers.

| | | |
|---|---|---|
| M13-20: | 5'-GTAAAACGACGGCCAGT-3' | (SEQ ID NO:25) |
| M13-RBV: | 5'-GGAAACAGCTATGACCATG-3' | (SBQ ID NO:26) |
| T7: | 5'-GTAATACGACTCACTATAGGGC-3' | (SEQ ID NO:27) |
| SP6: | 5'-ATTTAGGTGACACTATAG-3' | (SEQ ID NO:28) |

The opposite border fragment was isolated by one of two methods. In the first method BAC clones were digested with ScaI which deleted the majority of the genomic insert DNA. The remaining BAC clone was religated and the remainder of the insert amplified by PCR using the T7 (SEQ ID NO:27) and Belo840 (SEQ ID NO:29) primers. The second method involved an inverse PCR technique (Sambrook; Ochman H. et al. (1988) Genetics 120:621–623) after digestion of the BAC clone with BamHI and religation in which the opposite border fragment was amplified by PCR using primers IBAC1 (SEQ ID NO:30) and IBAC2 (SEQ ID NO:31). The border fragments obtained by PCR were subcloned from an agarose gel, and used as probes for isolating overlapping BAC clones.

| | | |
|---|---|---|
| Belo840: | 5'-TTTGTGATGGCTTCCATGTC-3' | (SEQ ID NO:29) |
| IBAC1: | 5'-GTCGACTCTAGAGGATCC-3' | (SEQ ID NO:30) |
| IBAC2: | 5'-CTGCAGGCATGCAAGCTT-3' | (SEQ ID NO:31) |

Walking One Step to the Left Defines the Left Recombination Border.

One insert border fragment of BAC clone 179G5, named 179G5R, appeared to be a single copy sequence using Southern gel blot analysis, and was used to probe the BAC library filters. This fragment identified four of the previously identified BAC clones, 5C1, 22H9, 136F8 and 179G5, as well as three new clones, 31H3, 107F10 and 157A9 (FIG. 2). An insert end fragment, named 31H3R, hybridized to new BAC clones 70F1 and 147G7. The overlapping rice BAC clones 31H3, 107F10, 157A9, 70F1 and 147G7 were subsequently shown to contain the DNA sequence corresponding to the RAPD marker SP4B9 that defines one border of the R-gene region (Recombination has occurred between SP4B9 and the Pi-ta gene in one progeny rice line out of the entire mapping population tested). The SP4B9 sequence was shown to reside at this location in the BAC contig using specific PCR primers GB24 and GB25 (SEQ ID NO:32 and 33) produced by subcloning and sequencing the linked SP4B9 PCR fragment from an agarose gel. This result defined the left border in the BAC contig of FIG. 2, indicating that the R-gene is located to the right in this figure.

```
GB24 5'-AGGCGTCTTCAGTTTTGTAATA-3'    (SEQ ID NO:32)

GB25 5'-AGGCGTCTTCCGGAAAGCAGCG-3'    (SEQ ID NO:33)
```

Walking to the Right:

The border fragment from the opposite end of BAC clone 179G5, called G179G5L, hybridized to itself on the BAC library filters as well as to new BAC clones 34H9, 50E12, 108E4 and 158C2. The BAC end fragment 158C2L hybridized to 158C2 as well as new BAC clones 35B3, 41F2 and 77D8. Because both the right and left border fragments of 77D8 contain repetitive DNA sequences, a single copy fragment internal to the BAC insert, called 77D8-12, was cloned from an agarose gel and used to probe the BAC library. This fragment identified 77D8 and 41F2, as well as new BAC clones 18D1, 6D5 and 142E8.

Random Genomic Sequencing of BAC Inserts to Identify R-Gene Candidates.

Overlapping BAC clones 31H3, 179G5, 34H9, 77D8 and 142E8 were nebulized by high pressure treatment with nitrogen gas (20 psi) in a reaction chamber (Nebulization tube, order #4207, IPI Medical Products, Chicago) for 90 seconds. The ends of the sheared and reprecipitated DNA fragments were blunt-ended by high fidelity DNA polymerase (PFU, Stratagene)—mediated fill-in reaction. DNA fragments in the size range of 1000–2000 bp were isolated from agarose gels using the QIAEX II Gel Extraction Kit (Qiagen, Chatsworth, Calif.) subcloned into the SmaI site of pUC18, and transformed into DH10B by electroporation. Clones containing BAC DNA inserts were sequenced in one direction using the universal reverse primer. Approximately 300 to 400 clones were sequenced for each BAC in order to have a reasonable chance of obtaining sequence from and identifying all genes contained in the set of clones. Similarity searches were done using the BlastX program (Gish, W. and States, D. J. (1993) Nature Genetics 3:266–272). For convenience, the P-value (probability) of observing a match of a sequence to a sequence contained in the searched databases merely by chance as calculated by BLAST is reported herein as "pLog" values, which represent the negative of the logarithm of the reported P-value. Accordingly, the greater the pLog value, the greater the likelihood that the sequence and the BLAST "hit" represent similar proteins. The clones were divided into three groups: those with highly significant hits (pLog>10); those with weakly significant hits (1<=[highest pLog]<=10); and those with no hits (pLog<1). For example, 370 sequences were obtained from RB142E8, with 60 (16.2%) falling in the highly significant class, 71 (19.2%) falling in the weakly significant class, and 239 (64.6%) falling in the no-hit class. Sequences with homology to previously cloned resistance genes, to plant receptor genes, or to plant defense genes were investigated further. Out of five candidates investigated in detail, one called PRG2 showed the most promise of being the Pi-ta gene.

PRG2 was identified by three sequences falling in the weakly significant hits category. For example, the amino acid sequence encoded by the 586 bp DNA fragment sequenced in bac142e8.pk0001.f12 (SEQ ID NO:34; "f12" in FIG. 3) possessed moderate similarity (pLog=5.80) to the protein PRF (GenBank accession U653391) that is required for R-gene function in tomato (Salmeron et al., 1996, Cell 86:123–133). It also was related (pLog=5.43) to the amino acid sequence encoded by the Arabidopsis R-gene RPM1 (X87851; Grant et al., 1995, Science 269:843–846). The 598 bp sequenced from bac142e8.pk0001.b7 (SEQ ID NO:35; "b7" in FIG. 3) identified the PRF gene and the Arabidopsis myosin heavy chain homolog (U19619), and the 605 bp insert of bac142e8.pk0001.f8 (SEQ ID NO:36; "f8" in FIG. 3) showed a 44 amino acid region with homology to the P-loop containing regions of RPM 1 and PRF. Primers from these genomic clones were made for further genomic sequencing in this region from the resistant rice variety Yashiro-mochi, described below. As the sequencing progressed, additional overlapping subclones were identified from the original set of 239 BAC fragments showing no significant hits (FIG. 3).

Example 7

Isolation of Genomic and cDNA Clones For the Pi-ta Candidate Gene

The nucleic acid fragments subcloned from BAC 142E8, described in Example 6 as comprising the putative Pi-ta locus, were accurately sequenced in order to design the strategy for cloning the full length gene. In particular, the rice genomic fragment in bac142e8.pk0001.f8 was 2 kb in size and contained 1255 bp of promoter sequence before the initiation codon (FIG. 3). Southern analyses of Yashiro-mochi genomic DNA and BAC 142E8 using agarose gel purified rice insert fragments from clones bac142e8.pk0001.b7 and bac142e8.pk0001.f12 showed that BAC RB142E8 contained a single copy of PRG2. This analysis also identified a 5.3 kb BamHI fragment from 142E8 that contained the remainder of the gene plus approximately 2 kb of 3' untranslated region. This 5.3 kb BamHI fragment was subcloned from the BAC DNA into the vector pBluescriptIISK+ (Stratagene) and was designated Clone #7 (FIG. 3). The entire gene was assembled by digesting both bac142e8.pk0001.f8 and Clone #7 with EcoRI, and ligating the 5.3 kb EcoRI fragment from Clone #7 in place of the small EcoRI fragment in bac142e8.pk0001.f8 (FIG. 4). The resulting vector, pCB1641, contained a 7.5 kb insert of rice DNA in the 2.7 kb vector. This rice clone included the full length PRG2 coding sequence along with 1255 bp of promoter sequence and approximately 2 kb of 3' untranslated sequence. The DNA sequence of 5757 bp of the genomic clone (SEQ ID NO:1, including the entire 5' sequence, the coding sequence and intron, and 252 bp past the termination codon) in pCB 1641 was determined for both strands by the primer walk method, with the use of DyeDeoxy terminator cycle sequencing and a model 377A DNA sequencing system (Applied Biosystems, Foster City, Calf.). Relative locations of some of the primers used are diagramed in FIG. 5 (SEQ ID NOS:37–64).

| | | |
|---|---|---|
| F8-2: | 5'-CCATCGGTGACCATGGG-3' | (SEQ ID NO:37) |
| 1641-1: | 5'-CCCTCTCCGTTGTTCCCATGG-3' | (SEQ ID NQ:38) |
| F8-4: | 5'-GGGTTGGAGAATGCATGG-3' | (SEQ ID NO:39) |
| 1641-2: | 5'-CCATGCATTCTCCAACCC-3' | (SEQ ID NO:40) |
| F8-3: | 5'-CATGGATGGAGACCTCTGC-3' | (SEQ ID NO:41) |
| F8-5: | 5'-TCCTCAGAGGCGATCTCC-3' | (SEQ ID NO:42) |
| F8-1: | 5'-GAACAGGGTGACCTCGTCG-3' | (SEQ ID NO:43) |
| F12-1: | 5'-GTGGCTTCCATTGTTGGATC-3' | (SEQ ID NO:44) |
| F12-5: | 5'-CGAACGGCGCATCCAACC-3' | (SEQ ID NO:45) |
| F12-6: | 5'-GTGTCCTCTATTAGTAAATAC-3' | (SEQ ID NO:46) |
| F12-7: | 5'-GTATTTACTAATAGAGGACAC-3' | (SEQ ID NO:47) |
| 1641-3: | 5'-GGGCCTCCCTTGTTCGG-3' | (SEQ ID NO:48) |
| 1641-4: | 5'-CCGAACAAGGGAGGCCC-3' | (SEQ ID NO:49) |
| F12-4: | 5'-CCTACAGATCTGTAGCCAGC-3' | (SEQ ID NO:50) |
| F12-3: | 5'-GCTGGCTACAGATCTGTAGG-3' | (SEQ ID NO:51) |
| F12-2: | 5'-GCTGGCTACAGATCTGTAGG-3' | (SEQ ID NO:52) |
| B7-1: | 5'-GCTGGCTACAGATCTGTAGG-3' | (SEQ ID NO:53) |
| B7-3: | 5'-GTGATTCCATTGCTGCATTCC-3' | (SEQ ID NO:54) |
| B7-4: | 5'-CATGTGTAGTGCACCACATGG-3' | (SEQ ID NO:55) |
| B7-2: | 5'-CTGTCGTCTGAGAATGATCC-3' | (SEQ ID NO:56) |
| C10-1: | 5'-CCAAGGACTACAACACTTGC-3' | (SEQ ID NO:57) |
| 173C12-5: | 5'-GCATCCCCAAATGGACTGG-3' | (SEQ ID NO:58) |
| 1641-5: | 5'-CCAGTCCATTTGGGGATGC-3' | (SEQ ID NO:59) |
| 173-6: | 5'-CAAGCATCCGACGCCGAGC-3' | (SEQ ID NO:60) |
| 173-7: | 5'-TTGTATATCAACCATAAGAGTGC-3' | (SEQ ID NO:61) |
| 1641-6: | 5'-GTTCTTTGATCCAAGTGTTAGG-3' | (SEQ ID NO:62) |
| GB46: | 5'-CATTAAAGTCGACCTCAAACAATCATCAAGTCAGGT-3' | (SEQ ID NO:63) |
| GB47: | 5'-AATGCAGAATTCACAACACCACTAGCAGGTTTG-3' | (SEQ ID NO:64) |

DNA sequence analysis of the rice genomic fragment (SEQ ID NO: 1; 5757 nucleotides) subcloned in pCB 1641 identified an open reading frame of 2784 nucleotides beginning at nucleotide 1256 and interrupted by one 1463 bp intron between nucleotides 2199 and 3663. The coding sequence corresponds to a deduced polypeptide with 928 amino acids (FIG. 6). The putative protein has a relative molecular weight of 105 kDa and a pI of 7.05. Four amino acid sequences matching the N-glycosylation consensus [NX(S/T) with X not being P] (Kornfeld et al., 1985, Ann. Rev. Biochem. 54:631) are present in the PRG2 protein.

To determine if PRG2 is present in a single copy or in multiple copies in the rice genome, blots of total genomic rice DNA were probed using nucleic acid fragments encoding either the amino-terminal portion of the gene (639 bp fragment amplified by primers F8-5 and F12-5) or the carboxy-terminal portion (nucleotides 4477 to 5503, amplified by primers GB47 and GB46). Blots were washed at 50° to 55° in 2×SSPE with 0.1% SDS, for low stringency hybridizations, and at 65° in 0.1×SSPE with 0.1% SDS for high stringency hybridization. Even under the high stringency conditions, the N-terminal probe (nucleic acid fragment comprising bases 1401 to 2040) identified a single copy against a general smear of background hybridization. Probing the very same blots with the C-terminal nucleic acid fragment (subcloned as pCB 1645, described below) identified one copy with no background smear. It was concluded that PRG2 is a single copy gene, but that there may be related genes in the rice genome.

The single copy C-terminal probe was subcloned for use as a hybridization probe. Primer GB47 was synthesized based on the sequence of this region from nucleotides 4465 through 4497, except that residues between 4471 and 4476 were modified to incorporate an EcoRI restriction site. Likewise, primer GB46 was the reverse-complement of nucleotides 5519 through 5484, except that the residues corresponding to nucleotides 5512 and 5506 were modified to incorporate a SalI restriction site. Primers GB46 and GB47 were used to amplify the gene fragment. After purification from an agarose gel as described in Example 6, and following digestion with the indicated enzymes, the nucleic acid fragment was subcloned into the EcoRI/SalI sites of the vector pBD-GAL4 Cam (Stratagene) to produce plasmid pCB1645 (FIG. 4B). The subcloned fragment was sequenced to confirm its structure.

A full-length Pi-ta cDNA fragment was cloned using reverse transcriptase (RT) PCR and subcloning. The approach involved isolating mRNA from transgenic Nipponbare line 27-4-8-1 which contained the transgene comprising a genomic Pi-ta nucleic acid fragment operably linked to the CaMV 35S promoter (Example 10, expression construct 3) and which was shown on a northern blot to overexpress Pi-ta. First strand cDNA was synthesized using the isolated mRNA fraction as template and the oligonucleotide GB67 (SEQ ID NO:65) as primer.

GB67: 5'-CCATTAAGCTTGGTTTCAAACAATC-3' (SEQ ID NO:65)

A partial Pi-ta cDNA (2.1 kb) was amplified from first strand cDNA using primers F12-1 (SEQ ID NO:44) and GB67 (SEQ ID NO:65). It was then cloned into pSL1180 (Pharmacia) using the BamHI (restriction site present in the Pi-ta nucleic acid fragment) and HindIII (restriction site present in GB67 sequence) cloning sites. To obtain a full-length synthetic cDNA, a 706 bp NcoI-BamHI fragment containing the 5' end of the Pi-ta coding sequence was isolated from pCB1649 and cloned into the NcoI-BamHI site upstream of the 2090 bp BamHI-HindIII partial Pi-ta cDNA fragment to create a full-length promoter-less Pi-ta cDNA. DNA sequence analysis determined that there was a 2 bp deletion present at codon 796 (probably a PCR artifact) resulting in a frameshift mutation that would have truncated the predicted Pi-ta protein by 119 amino acids. This was corrected by replacing a 1400 bp SphI-BglII fragment with the corresponding fragment from pCB 1649 which contained the correct sequence, to create pCB 1906. DNA sequence analysis also determined that the predicted intron was precisely spliced in this synthetic cDNA. A native Pi-ta promoter fragment (2425 bp) was added by cloning a 3173 bp EcoRI fragment from pCB 1649 into the EcoRI sites of pCB 1906, resulting in plasmid pCB 1926 which contained the final Pi-ta cDNA construct (FIG. 7C).

Example 8

Cloning of the Pi-ta Candidate Gene From Susceptible Rice Variety Tsuyuake and Sequence Analysis for Comparison of Resistant and Sensitive Alleles A rice genomic library was constructed in bacteriophage lambda using DNA from the susceptible variety Tsuyuake (Sambrook). Genomic DNA was prepared using a procedure described by Dellaporta et al., (1983) *Plant Mol. Biology Reporter* 1: 19–27. The genomic DNA was subjected to partial digestion with the restriction enzyme Tsp509I (cuts at 5'-AATT-3'). DNA fragments in the size range of 7 to 10 kb were purified from an agarose gel and subcloned into the EcoRI site of vector λZapII (Stratagene). Screening the Tsuyuake library by hybridization with the DNA insert of pCB 1641 identified 8 overlapping clones with sequences related to PRG2. Two clones that overlapped by 1 kb and included the entire coding sequence, T2-9 and T2-2, were sequenced using the primers in FIG. 5. The sequence of the cloned genomic fragments from Tsuyuake were identical to sequences obtained from PCR-amplified genomic DNA of the susceptible DH rice line YT16.

Comparison of Resistant and Sensitive Alleles From Multiple Rice Lines.

The functional Pi-ta coding sequence from resistant Yashiro-mochi rice (contained in SEQ ID NOS:1 and 68) differs by 7 nucleotides from the sequence of the nonfunctional coding sequence from sensitive Tsuyuake rice (contained in SEQ ID NO:3). The 7 basepair substitutions in the coding region result in 5 amino acid differences between the two proteins (FIG. 6). Six additional basepair changes occur in the intron sequences. Most of the nucleotide differences in the coding region occur in the region preceding the P-loop motif. Both genes encode proteins with identical NBS motifs and with the 4 potential N-glycosylation sites at positions 339, 556, 654 and 838.

As determined by RNA gel blot analysis with polyA$^+$-RNA, both the Pi-ta gene from Yashiro-mochi and the susceptible allele from Tsuyuake are transcribed with an estimated transcript size of 3.3 kb. Further, RNA blot analysis demonstrates that both alleles are constitutively expressed. This analysis was done by probing polyA$^+$-RNA blots with the C-terminal Pi-ta fragment that had been cloned in pCB1645. Poly A$^+$-mRNA was prepared from 2 week old leaves of resistant rice variety YT14, or from susceptible rice variety YT16 by the method of Perry and Francki (1992, J. Gen. Virol. 73:2105–2114). RNA gel blot analysis was performed according to the method of Ausubel et al. (1987 Protocols in Molecular Biology, New York, John Wiley and Sons).

The sequences of genomic clones of Pi-ta nucleic acid fragments from additional varieties of rice were obtained in order to see if the differences in nucleic acid sequences were conserved in resistant versus susceptible forms of the Pi-ta gene. Using primers listed in FIG. 5, PCR products of the Pi-ta gene were sequenced from the resistant varieties Tadukan and K1. These varieties are believed to have acquired a Pi-ta resistance gene in a manner independent of that which resulted in the presence of the gene in Yashiro-mochi. The same PCR primers were used to sequence the nucleic acid fragment from an additional susceptible Japanese rice variety, Nipponbare, and from the unrelated susceptible variety, Sariceltik. To determine if the sequence differences were due to a difference between japonica versus indica alleles, the nucleic acid fragment was sequenced from the susceptible indica variety C101A51. The result shows a strong correlation between nucleic acid sequence and resistance to strains of the rice blast pathogen containing AVR-Pita; over the region sequenced, Tadukan and K1 have an identical sequence to Pi-ta from Yashiro-mochi (Table 4), and the genes from Nipponbare and Sariceltik have the identical sequence to the susceptible pi-ta gene from Tsuyuake. The nucleotide sequence of the indica C101A51 allele suggests that a single amino acid difference, alanine versus serine at position 918, determines the specificity of Pi-ta function.

TABLE 4

Amino Acid Differences Between Resistant and Sensitive R-Proteins

| | | AMINO ACID AT POS. NO. | | | | |
|---|---|---|---|---|---|---|
| RICE VARIETY | PHENOTYPE | 6 | 148 | 158 | 176 | 918 |
| YTI4* | Resistant | I | R | H | D | A |
| Tadukan | Resistant | I | R | H | D | A |
| K1 | Resistant | I | R | H | D | A |
| C101A51 | Susceptible | I | R | H | D | S |
| Tsuyuake | Susceptible | S | S | Q | V | S |

TABLE 4-continued

Amino Acid Differences Between Resistant and Sensitive R-Proteins

| | | AMINO ACID AT POS. NO. | | | | |
|---|---|---|---|---|---|---|
| RICE VARIETY | PHENOTYPE | 6 | 148 | 158 | 176 | 918 |
| Nipponbare | Susceptible | S | S | Q | V | S |
| Sariceltik | Susceptible | S | S | Q | V | S |

*Has R-gene from Yashiro-mochi

Example 9

Identification of Pi-ta Function by Transient Expression in Rice

As is standard practice to those skilled in the art, high velocity biolistic bombardment of plant tissue with particles coated with recombinant expression constructs of interest results in transient expression of the nucleic acid fragments from the introduced plasmids. Function of disease resistance genes can be demonstrated in transient leaf bombardment experiments using reporter gene expression to assay for triggering of the hypersensitive cell death resistance response. Such assays have demonstrated utility for identifying R-genes for bacterial pathogens because the corresponding AVR-gene required for triggering resistance responses can be supplied by uniform infiltration of the plant tissue with the bacterial pathogen (Mindrinos et al., 1994, Cell 78:1089–1099). Uniform pathogen infiltration is not possible with fungal pathogens such as M. grisea that directly penetrate through the plant cuticle and produce localized lesions at the point of penetration.

In order to overcome the obstacle to uniform incorporation of the fungal AVR-gene within the plant tissue, introduction of an AVR-Pita expression construct was tested by co-bombardment along with the GUS reporter gene. In particular, a construct was engineered that expresses the putative mature protease (AVR-Pita176) under control of the 35S promoter for constitutive expression in plant cells. First, pML63 (FIG. 7B) was cut with NcoI, and blunted with S1 nuclease. The GUS nucleic acid fragment was then removed by further digestion with Asp718. A linker fragment generated with primers ML132 (SEQ ID:69) and ML 133 (SEQ ID: 70) was cloned into the blunted NcoI and Asp718 sites to produce pML 135.

ML132: 5'-CACGTGGAATTCCCCGGGG-3'  (SEQ ID NO:69)

ML133: 5'-GTACCCCCGGGGAATTCCACGTG-3' (SEQ ID NO:70)

pML135 was digested with PmlI and Asp718, and the Adh1–6 intron amplified by PCR from maize genomic DNA using primers ML 111 (SEQ ID:71) and ML135 (SEQ ID:72) was cloned into pML 135 to create pML 141.

(SEQ ID NO:71)
ML111:   5'-CCCGGGGAATTCCTGCAGAAGGTG
         CAAGGATTGCTGGAGCG-3'

(SEQ ID NO:72)
ML135:   5'-TTTAAAGGTACCCCATGGCACGTGCCGGC
         TTGTTGTGGTCTTTTGGGTTCAC-3' pML142 was finally created by digested pML141 with BamHI and NcoI and the 1.9 kb fragment containing the 35S/Adh1–6 sequence from pML141 was cloned into the BamHI/NcoI sites of pML63.

Plasmid pAVR3 contained nucleotides 139–672 of the AVR-Pita nucleic acid fragment (SEQ ID NO:5) encoding the predicted mature protease plus one additional N-terminal amino acid (AVR-Pita$_{177}$, beginning with Ile-47 of the preproprotein) and a start codon met fused to the 35S/Adh1–6 promoter in vector pML 142. The AVR-Pita nucleic acid fragment (SEQ ID NO:5) was amplified by PCR from AVR-Pita cDNA using primers AV1 (SEQ ID NO:73) and AV3 (SEQ ID NO:74), digested with PmlI and KpnI, blunted with Klenow polymerase and cloned into pML 142 that had also been cut with PmlI and KpnI and blunted with Klenow polymerase, resulting in pAVR3.

(SEQ ID NO:73)
AV1:   5'-GCCGGCACGTGCCATGATTGAACGCTATTCCCAATG-3'

(SEQ ID NO:74)
AV3:   5'-GCCGGGATCCCCCTCTATTGTTAGATTGAC-3'

The coding sequence for the predicted mature protease (beginning with Glu-48 of the preproprotein) was obtained by PCR-amplification from the AVR-Pita nucleic acid fragment (SEQ ID NO:5) in plasmid pAVR3 using oligonucleotides YL30 containing an in-frame NcoI site (SEQ ID NO:66) and YL37 (SEQ ID NO:67). The PCR fragment was cloned NcoI/KpnI into pML142 resulting in vector pCB1947. This was done to eliminate the Ile-47 codon (att) in pAVR3 and generate AVR-Pita$_{176}$. Additional details are described in the Legend to FIG. 7A.

(SEQ ID NO:66)
YL30:   5'-ACAACAAGCCGGCACGTGCCATGGAACGCT-3'
(SEQ ID NO:67)
YL37:   5'-TCCTTCTTTAGGTACCGCTCTCTC-3'

To determine if expression of the AVR-Pita$_{176}$ construct triggers Pi-ta mediated defense responses when introduced into Pi-ta-containing plant cells, seedlings from Pi-ta-plants (Yashiro-mochi and YT14) and plants that lack Pi-ta (Nipponbare and YT16) were co-bombarded with the 35S/Adh1–6:.AVR-Pita$_{176}$ gene construct and the 35S::GUS reporter gene (FIG. 7). Seeds were germinated on leaf assay media: ½ strength MS medium (Murashige and Skoog, 1962, Physiol. Plant. 15:473–497) supplemented with 100 mg casein hydrolysate and 0.5% agarose for a week in an incubator at 25° C. for 48 hours in 12 hr photoperiod with a 100 $\mu Em^{-2}s^{-1}$ of cool, white light. Two-leaf seedlings were excised from the agar medium using a surgical razor and placed in a petri dish containing a prewetted filter paper. Plantlets were labeled at the base with a permanent marker for identification. Biolistic bombardment of the seedlings was performed using Bio-Rad PDS-1000/He apparatus and 1150-psi rupture disks. Gold particles, (0.6 $\mu$m diameter), were prepared according to the instructions provided by the manufacturer. For each cobombardment, 1 $\mu$g of gold particles was coated with 1.5 $\mu$g of 35S/GUS and 1 $\mu$g of other plasmids. After bombardment, seedlings were maintained at 25° C. for 48 hours in Petri dishes containing prewetted filter paper. Leaves were cleared in 70% ethanol and histochemically assayed for β-Glucuronidase (GUS) activity using 5-bromo-4-chloro-3-indolyl glucuronide (X-gluc) as a substrate (Jefferson, 1987, Plant Mol. Bio. Rep. 5:387–405).

The functional AVR-Pita$_{176}$ expression construct mediated a striking decrease in GUS expression (suggesting cell death prior to expression), when co-bombarded with the GUS construct into leaves containing the endogenous Pi-ta gene. As predicted, the AVR-Pita$_{176}$ expression construct showed significantly higher activity than a similar expression construct containing the full lengthAVR-Pita coding sequence. Early experiments revealed a hypersensitive-like response upon bombardment of leaves of intact Yashiro-mochi seedlings, based on observation of typical Type 1 necrotic lesions and a decrease in GUS expression, but necrotic lesion formation was not as reproducible as the decrease in GUS activity. Mutant forms of AVR-$Pita_{176}$ that fail to confer avirulence also fail to decrease GUS expression. Nor is the effect seen in rice varieties that lack an endogenous Pi-ta gene. Thus, expression of the AVR-Pita coding sequence triggers the rice defense response when introduced directly into rice leaves containing the endogenous Pi-ta gene.

PRG2 functions in place of the endogenous Pi-ta gene in the transient expression assay.

Resistant (YT14) and susceptible (YT16) rice leaves were co-bombarded with the AVR-$Pita_{176}$ (pCB1947; FIG. 7A), GUS (pML63; FIG. 7B) and the Pi-ta cDNA (pCB1926; FIG. 7C) expression constructs in order to see if exogenously supplied PRG2 can complement endogenous Pi-ta function. Typical leaves from this assay are shown in FIG. 8. Decreased levels of GUS expression were observed in resistant (YT14) leaves whether or not the Pi-ta expression construct was co-bombarded with AVR-$Pita_{176}$, and GUS. In susceptible (YT16) rice leaves, however, a marked decrease in GUS expression was noted only if the Pi-ta expression construct was co-bombarded with AVR-$Pita_{176}$, and GUS. Thus, PRG2 functions in place of the endogenous Pi-ta gene in recognizing AVR-$Pita_{176}$ and inducing localized cell death. Control leaves of susceptible YT16 seedlings shot with AVR-$Pita_{176}$ and GUS only had high levels of GUS expression. The sensitive allele from variety C10A51, which differs by a single amino acid from Pi-ta, did not result in a decrease in GUS expression when co-bombarded with AVR-$Pita_{176}$ and GUS, indicating that specificity is maintained in this assay. These experiments are consistent with a conclusion that PRG2 is, in fact, a Pi-ta gene.

Example 10

Production of Transgenic Rice Containing the Putative R-gene

As is standard practice in molecular plant pathology, identification of R-gene function involves stable introduction (i.e., transformation) of a transgene into susceptible plants, and the demonstration that this transgene confers a resistance phenotype to the host plant that was previously characterized as susceptible. One method for transforming DNA into eukaryotic cells of higher plants that is available to those skilled in the art is high-velocity ballistic bombardment using metal particles coated with the nucleic acid constructs of interest (see Klein et al. Nature (1987) (London) 327:70–73, and see U.S. Pat. No. 4,945,050). A Biolistic PDS-1000/He (BioRAD Laboratories, Hercules, Calif.) was used for these experiments. The particle bombardment technique was used to transform the susceptible rice variety Nipponbare with four different expression constructs containing the putative Pi-ta nucleic acid fragments:

1) pCB1641—plasmid containing the 7 kb Pi-ta nucleic acid fragment including a 1255 bp native promoter region (FIG. 4A, SEQ ID NO:1).
2) pCB 1649—plasmid containing an 8.4 kb Pi-ta nucleic acid fragment including a 3 kb native promoter. This vector is identical to pCB1641 except that it contains a longer promoter region. To make pCB1649, pCB1641 was cut with HindIII/SacII to excise a 1.58 kb fragment. This was replaced by a 4.98 kb HindIII/SacII subclone of BAC142E8 to create pCB 1649. This cloning step essentially replaced the 1255 bp promoter in pCB1641 with a longer 4656 bp promoter fragment.
3) 35S/Pi-ta—plasmid containing a 5.36 kb Pi-ta nucleic acid fragment operably linked to a 1.9 kb modified 35S promoter fragment. This vector was constructed by cloning a 5.36 kb NcoI/KpnI fragment from pCB1641 into the NcoI/KpnI sites of plasmid pML63 which contained the 35S promoter fragment.
4) pCB 1926—plasmid containing Pi-ta cDNA nucleic acid fragment and a 2425 bp native promoter region described in FIG. 7C, SEQ ID NO:68.

The bacterial hygromycin B phosphotransferase (Hpt II) gene from *Streptomyces hygroscopicus* that confers resistance to the antibiotic was used as the selectable marker for rice transformation. In the vector was used, pML18, the Hpt II gene was engineered with the 35S promoter from Cauliflower Mosaic Virus and the termination and polyadenylation signals from the octopine synthase gene of *Agrobacterium tumefaciens*. pML 18 is described in WO 97/47731, which was published on Dec. 18, 1997, the disclosure of which is hereby incorporated by reference.

Embryogenic callus cultures derived from the scutellum of germinating Nipponbare seeds served as source material for transformation experiments. This material was generated by germinating sterile rice seeds on a callus initiation media (MS salts, Nitsch and Nitsch vitamins, 1.0 mg/l 2,4-D and 10 $\mu$M $AgNO_3$) in the dark at 27–28° C. Embryogenic callus proliferating from the scutellum of the embryos was the transferred to CM media (N6 salts, Nitsch and Nitsch vitamins, 1 mg/l 2,4-D, Chu et al., 1985, Sci. Sinica 18: 659–668). Callus cultures were maintained on CM by routine sub-culture at two week intervals and used for transformation within 10 weeks of initiation.

Callus was prepared for transformation by subculturing 0.5–1.0 mm pieces approximately 1 mm apart, arranged in a circular area of about 4 cm in diameter, in the center of a circle of Whatman #541 paper placed on CM media. The plates with callus were incubated in the dark at 27–28° C. for 3–5 days. Prior to bombardment, the filters with callus were transferred to CM supplemented with 0.25 M mannitol and 0.25 M sorbitol for 3 hr. in the dark. The petri dish lids were then left ajar for 20–45 minutes in a sterile hood to allow moisture on tissue to dissipate.

Circular plasmid DNA from two different plasmids, for example, pML 18 containing the selectable marker for rice transformation and pCB 1641 containing the putative R-gene, were co-precipitated onto the surface of gold particles. To accomplish this, a total of 10 $\mu$g of DNA at a 2:1 ratio of trait:selectable marker DNAs were added to 50 $\mu$l aliquot of gold particles that had been resuspended at a concentration of 60 mg $ml^{-1}$. Calcium chloride (50 $\mu$l of a 2.5 M solution) and spermidine (20 $\mu$l of a 0.1 M solution) were then added to the gold-DNA suspension as the tube was vortexing for 3 min. The gold particles were centrifuged in a microfuge for 1 sec and the supernatant removed. The gold particles were then washed twice with 1 ml of absolute ethanol and then resuspended in 50 $\mu$l of absolute ethanol and sonicated (bath sonicator) for one second to disperse the gold particles. The gold suspension was incubated at −70° C. for five minutes and sonicated (bath sonicator) if needed to disperse the particles . Six $\mu$l of the DNA-coated gold particles were then loaded onto mylar macrocarrier disks and the ethanol was allowed to evaporate.

At the end of the drying period, a petri dish containing the tissue was placed in the chamber of the PDS-1000/He. The air in the chamber was then evacuated to a vacuum of 28–29 inches Hg. The macrocarrier was accelerated with a helium shock wave using a rupture membrane that bursts when the He pressure in the shock tube reaches 1080–1100 psi. The tissue was placed approximately 8 cm from the stopping screen and the callus was bombarded two times. Five to seven plates of tissue were bombarded in this way with the DNA-coated gold particles. Following bombardment, the callus tissue was transferred to CM media without supplemental sorbitol or mannitol.

Within 3–5 days after bombardment the callus tissue was transferred to SM media (CM medium containing 50 mg/l hygromycin). To accomplish this, callus tissue was transferred from plates to sterile 50 ml conical tubes and weighed. Molten top-agar at 40° C. was added using 2.5 ml of top agar/100 mg of callus. Callus clumps were broken into fragments of less than 2 mm diameter by repeated dispensing through a 10 ml pipet. Three ml aliquots of the callus suspension were plated onto fresh SM media and the plates were incubated in the dark for 4 weeks at 27–28° C. After 4 weeks, transgenic callus events were identified, transferred to fresh SM plates and grown for an additional 2 weeks in the dark at 27–28° C.

Growing callus was transferred to RM1 media (MS salts, Nitsch and Nitsch vitamins, 2% sucrose, 3% sorbitol, 0.4% gelrite +50 ppm hyg B) for 2 weeks in the dark at 25° C. After 2 weeks the callus was transferred to RM2 media (MS salts, Nitsch and Nitsch vitamins, 3% sucrose, 0.4% gelrite +50 ppm hyg B) and placed under cool white light (~40 $\mu Em^{-2}s^{-1}$) with a 12 hr photoperiod at 25° C. and 30–40% humidity. After 2–4 week in the light, callus began to organize, and form shoots. Shoots were removed from surrounding callus/media and gently transferred to RM3 media (½× MS salts, Nitsch and Nitsch vitamins, 1% sucrose +50 ppm hygromycin B) in phytatrays (Sigma Chemical Co., St. Louis, Mo.) and incubation was continued using the same conditions as described in the previous step.

Plants were transferred from RM3 to 4″ pots containing Metro mix 350 after 2–3 weeks, when sufficient root and shoot growth had occurred. Plants were grown using a 12 hr/12 hr light/dark cycle using ~30/18° C. day/night temperature regimen.

Example 11

Identification of Pi-ta by Functional Complementation in Transgenic Rice

Molecular Analysis of the Transformants.

Allele specific PCR, as well as DNA gel blot analysis, was used to analyze transformants for the presence of R-gene sequences. High-stringency DNA gel blot analysis was performed, as described in Example 7, using the PRG2 DNA insert from pCB1645 as the hybridization probe. FIG. 9 shows a typical result from analysis of transformants produced with the PRG2 isolated nucleic acid fragment in pCB1641. Events ranged from insertion of single copies of the putative Pi-ta gene to complex multi-copy insertions.

Assay for Gain of the Resistance Phenotype. Pathogenicity assays were done as described in Example 2 using the AVR-gene containing pathogen strains 4360-R-62 or O-137 to test for gained resistance function. Table 5 shows the results from assays performed on primary transformants produced by co-bombardment with pCB 1641 and the $Hyg^R$ plasmid (pML 18).

TABLE 5

| TRANSFORMANT | DISEASE PHENOTYPE | | |
|---|---|---|---|
| | RESISTANT | INTER-MEDIATE | SUSCEPTIBLE |
| $Hyg^R$,Pi-ta | 7 | 13 | 22 |
| $Hyg^R$,lack Pi-ta | 0 | 0 | 16 |

For construct pCB1641, 7 out of 42 transformants assayed were resistant and 13 out of 42 were intermediate. Intermediate resistance was characterized by uniformly lower numbers of lesions that were also smaller than produced by fungal strains lacking AVR-Pita. For the construct with the PRG2 coding sequence operably linked to the 35S promoter, 4 out of 41 showed intermediate resistance. It was not surprising that 22/42 primary transformants containing the Pi-ta transgene (pCB1641) were susceptible, this was likely a result of three different problems affecting biolistic plant transformation. Many integration events contained multiple copies of the Pi-ta transgene (FIG. 9) including some that may have been fragmented. This can result in gene silencing events. Secondly in some integration events the transgene can be inserted into a chromosomal region that is unfavourable for gene expression. A third possible factor may have been gene inactivation by small deletions or frameshift mutations in the transgene that could not be detected on a Southern blot.

R1 seedlings derived from a single R0 transformant were divided into two sets and inoculated with either the avirulent stain O-137 or a virulent mutant derived from O-137 (CP3337) in order to determine if the resistance phenotype was stable through meiosis and if the resistance had specificity characteristic of the Pi-ta resistance gene. For example, DNA gel blot analysis (FIG. 10) of R1 seedling family 22-6-10-1 shows stable inheritance of the transgene correlating with Pi-ta-specific resistance. Results of the R1 analysis demonstrate that PRG2 confers resistance with specificity characteristic of the Pi-ta gene and that this resistance is stably inherited. Thus, it was concluded that SEQ ID NO:1 corresponds to the Pi-ta resistance gene.

Example 12

Characterization of the Pi-ta Resistance Gene Product

The encoded polypeptide of a candidate Pi-b gene sequence (accession AB013448), now available in Genbank, displays 30% identity (49% similarity) with a subfragment corresponding substantially to amino acid residues 200 to 680 of the Pi-ta polypeptide set forth in SEQ ID NO:2. Using BESTFIT (Smith and Waterman, 1981, Advances in Applied Mathematics 2: 482–489), the translated Pi-ta polypeptide sequence from amino acid residues 208 to 527 was found to show 30.3% identity (44.3% similarity) to the amino acid sequence of the RPM1 protein (Grant et al., 1995, Science 269:843–846). The same region shows 27.4% identity (38.8% similarity) to the tomato PRF protein, which is implicated in disease resistance signal transduction pathways (Salmeron et al., 1996, Cell 86:123–133), and 24.5% identity (38% similarity) to the product of the Arabidopsis R-gene RPS2 (Bent et al., 1994, Science 265:1856–1860; Mindrinos et al., 1994, Cell 78:1089–1099). No significant similarity is seen to the leucine-rich regions of any of these previously cloned R-gene products.

A prominent feature of the Pi-ta gene product is the NBS motif characteristic of numerous ATP- and GTP-binding proteins (Traut, 1994, Eur. J. Biochem. 229:9–19). Amino acids 236 to 244 match the generalized consensus GXGXXG(R/k)V for the phosphate binding (P) loop. The probable companion kinase domains are located at amino acids 314–323 (kinase domain 2a) and around amino acids 342 to 353 (kinase domain 3a). A conserved internal hydrophobic domain found in the two subclasses of cytoplasmic R-gene products (Jones and Jones, 1997, Adv. Bot. Res. Incorp. Adv. Plant Pathol. 24:89–167) is partially present between amino acids 407 to 415. However, key features of the two R-gene subclasses are not found in Pi-ta. First, the Pi-ta gene product has a unique amino terminus, lacking either the potential leucine zipper motif of the RPS2 gene-product subfamily (Bent et al., 1994, Science 265:1856–1860; Mindrinos et al., 1994, Cell 78:1089–1099) or the Toll/Interleukin-1 receptor homology encoded by the N gene subfamily (Whitman et al., 1994, Cell 78:1101–1115). Perhaps most importantly, the carboxy terminal portion of the Pi-ta gene product is leucine rich, but it does not fit any consensus sequence for leucine-rich repeats reported for R-gene products (Jones and Jones, 1997, Adv. Bot. Res. Incorp. Adv. Plant Pathol. 24:89–167).

What is claimed is:

1. An isolated nucleic acid fragment which confers a Pi-ta resistance gene mediated defense response against diseases caused by fungal pathogens comprising an AVR-Pita gene wherein said nucleic acid fragment encodes a polypeptide having a sequence identity of at least 90% when compared to a polypeptide sequence as set forth in SEQ ID NO:2.

2. A gene comprising the nucleic acid fragment of claim 1 operably linked to regulatory sequences.

3. The gene of claim 2 wherein said gene is chimeric.

4. A transgenic plant comprising in its genome the nucleic acid fragment of claim 1 operably linked to a native promoter wherein said fragment is not endogenous to the plant into which it is transformed.

5. A plant comprising in its genome the gene of claim 2 or claim 3.

6. The plant of claim 4 wherein the plant is a monocot.

7. The plant of claim 5 wherein the plant is a monocot.

8. The plant of claim 4 wherein the plant is a cereal.

9. The plant of claim 5 wherein the plant is a cereal.

10. The plant of claim 8 wherein the cereal is selected from the group consisting of rice, wheat, barley, corn, finger millet and pearl millet.

11. The plant of claim 4 wherein the plant is a natural host for *Magnaporthe grisea*.

12. The plant of claim 5 wherein the plant is a natural host for *Magnaporthe grisea*.

13. Seeds of the plants of one of claims 4,6,8, 10 or 11.

14. Seeds of the plants of claim 5.

15. Seeds of the plants of claim 7.

16. Seeds of the plants of claim 9.

17. Seeds of the plants of claim 12.

18. The nucleic acid fragment of claim 1 wherein said fragment confers resistance to the rice blast fungus.

19. The nucleic acid fragment of claim 1 wherein said fragment confers resistance to a fungal pathogen comprising the AVR-Pita gene wherein the AVR-Pita gene encodes a polypeptide having a sequence identity of at least 80% when compared to a polypeptide sequence as set forth in SEQ ID NOS: 6 or 8.

20. A method of conferring a resistance gene-mediated defense response in plants, which comprises transforming the plant with an expression construct comprising the nucleic acid fragment of claim 1 operably linked to regulatory sequences.

21. A method of conferring a resistance gene-mediated defense response in plants, comprising transforming the plant with a recombinant expression construct which comprises (1) the nucleic acid fragment of claim 1 and (2) an AVR-Pita isolated nucleic acid fragment wherein the AVR-Pita isolated nucleic acid fragment encodes a polypeptide having a sequence identity of at least 80% when compared to a polypeptide sequence as set forth in SEQ ID NOS: 6 or 8 wherein said nucleic acid fragments are operably linked to regulatory sequences and further wherein said construct confers a resistance gene-mediated defense response in plants against diseases caused by a fungal pathogen at the site of infection.

22. The method of claim 20 or 21 wherein resistance to rice blast fungus is conferred.

23. The method of claim 20 or 21 wherein the plant is a monocot.

24. The method of claim 20 or 21 wherein the plant is a cereal.

25. The method of claim 20 or 21 wherein the cereal is selected from the group consisting of rice, wheat, barley, corn, finger millet and pearl millet.

26. The method of claim 20 or 21 wherein the plant is a natural host for *Magnaporthe grisea.*

27. A recombinant expression construct which confers a resistance gene-mediated defense response in plants against diseases caused by a fungal pathogen at the site of infection which comprises (1) the isolated nucleic acid fragment of claim 1 and (2) an AVR-Pita isolated nucleic acid fragment wherein said AVR-Pita fragment encodes a polypeptide having a sequence identity of at least 80% when compared to a polypeptide sequence as set forth in SEQ ID NOS: 6 or 8 wherein said nucleic acid fragments are operably linked to regulatory sequences.

28. The recombinant expression construct of claim 27 wherein said construct confers resistance to rice blast fungus.

29. A plant comprising in its genome the expression construct of claim 27 or 28.

30. The plant of claim 29 wherein the plant is a monocot.

31. The plant of claim 30 wherein the plant is a cereal.

32. The plant of claim 31 wherein the cereal is selected from the group consisting of rice, wheat, barley, corn, finger millet and pearl millet.

33. The plant of claim 29 wherein the plant is a natural host for *Magnaporthe grisea*.

34. Seeds of the plant of claim 29.

35. Seeds of any of the plants of one of claims 30, 31, 32 or 33.

36. An isolated nucleic acid fragment which confers a Pi-ta resistance gene mediated defense response in plants against diseases caused by fungal pathogens wherein said nucleic acid fragment has a sequence identity of at least 90% when compared to the nucleotide sequence set forth in SEQ ID NOS: 1 or 68.

37. The nucleic acid fragment of claim 36 wherein the sequence identity is at least 95%.

* * * * *

SEQUENCE LISTING

<160> NUMBER OF SEQ ID NOS: 74

<210> SEQ ID NO 1
<211> LENGTH: 5757
<212> TYPE: DNA
<213> ORGANISM: Oryza sativa

<400> SEQUENCE: 1

```
gatgccgtcg tatactcgta tgctgctgcc ttctatcgat cgatcaaact cccgagtccc      60
gagtccgagt cgcgtacgcg tgccggcgtg cggcgccgtg tgcgtccgca gttcgcaggc     120
cgcacgctcg gctgggctgg ctctagtcct actgggcttc tcgcaggtgg gggcccctgg     180
aaattggggg ccccctgcga tcgcccagct cgctctccgc gatcgacggg cctgggtagt     240
tagcaccttg atcctggtta ccactacctc tcgagtagat ggcatctact cgagaggtag     300
tggcagccaa gaattaacaa cataggccgg tgatgacgag ggagacagca ccatcggtga     360
ccatgggaac aagggagagg gcattaatgg aagtgttgct aacccaaagc tactactatg     420
aagataagta ctgtaggatt agtactctca actcagtggc atgcttttat ccaaaaggct     480
acaatcaaga gttgcttcca gggcaaatgc ccttagttat gctttttttt tttaatcccc     540
aatgggctct cctctgtaga attttcttcc aactttatcc tctttggagt ttggcctaac     600
ctaacatcta attatatagt taccatcgta caacgttact ctcaagcgag aaccaagtcg     660
tcatagttcc aaagtaggaa aagttattcc attaattagc tactcggtcc atgcaaagat     720
cgtaagcata tttatttat catcgagacc aagaaaaaaa attaactcat tcgatttgta     780
ctcccatgta acaaactttt tcatatgcat gcaaaagggt tggagaatgc atggcagctc     840
aagtttcggt caacaattta atcatacacg gtaaaacgaa aagagactct cttcatttaa     900
ggctcggatg catggagact atatgaataa gctcatctca tttggaaaaa aataatcaaa     960
acaatgaaat atgcttaata catttggatt tggatggagt atctccctat gacgaaagag    1020
acgagggatt gcctacttct ttccacatca acctttgaag gctatggcag agctacattt    1080
gcagcgcagc ctctctgcat gatttcttac tagataggat taagtttcaa gagttaattt    1140
cttgtactct tgggcgatcc atgctgtcaa atcagcaact aacgaggcat aatctcgatc    1200
actagctctg atctgatctt cagctagcgc cggcgagctg cagaggtctc catccatggc    1260
gccggcggtc attgcatcgc agggtgtcat catgcggtcc ctgacgagca agctcgactc    1320
gctgctgctg cagccgccgg agccgccgcc gcctgcgcaa ccgtcgtcgc tgcggaaggg    1380
ggagaggaag aagatcctcc tcctcagagg cgatctccga cacctgctag atgactacta    1440
cctcctcgtg gagccgccgt cagacaccgc gccaccgcca gactcgacgg cggcgtgctg    1500
ggctaaggag gttcgcgagc tctcctacga cgtcgacgac ttcctcgacg agctaacgac    1560
```

-continued

```
ccagctcctc caccaccgcg gcggcggcga tggcagtagc actgctggtg ccaagaagat    1620
gatcagcagc atgatcgcgc ggcttcgagg ggagcttaac cggcggcggt ggatcgccga    1680
cgaggtcacc ctgttcaggg cccgcgtgaa ggaggccatt cgccgccacg agagctacca    1740
tcttggcagg cgcacctcga gctcgaggcc gagagaagaa gacgacgacg acgatcgcga    1800
ggactccgcc ggcaacgaac gccgccggtt tctgtcgctg acgttcggga tggacgacgc    1860
tgctgtgcac ggccagctcg ttggtaggga tatttcgatg caaaagctcg tccggtggct    1920
ggccgacggc gagccgaagc tcaaggtggc ttccattgtt ggatccggag gtgttggcaa    1980
gacgacgctg gccacagaat tctatcgtct gcatggccgg cggttggatg cgccgttcga    2040
ctgccgggct ttcgtgcgga cgccccggaa gcctgacatg acgaagatcc tcaccgacat    2100
gctgtcacag ctgcggccac aacatcagca tcagtcttcg gatgtttggg aggttgatcg    2160
actccttgaa actatccgga cgcatttgca agataaaagg taattcatgt ctacatctat    2220
ctctagtatt ttttcatga atttacaaac tattttctca aatttcccct tttttatcct    2280
tcatatagta attaagttag taactataca tatgaattta atttactcga caatgccaat    2340 aatatttta attacttta tagtgtcctc tattattaaa tacaattcga tcgagccatg    2400
aatcatactg gtaatctaaa caattattat acccacctca ttctactaac agcaattgag    2460
ttgttaatat aaatagatat ggtctattgc atgaaaaaat aaaggtaaag tgtttacatt    2520
atttctacta ctagtagcag aactacaaag ttgtttgtat ttttaattat taaatgtaaa    2580
tgaaagtaca tgtttcatac ccttgttatt tttttaggcg actaaactac tagtacatta    2640
tttctactac tagtagaaca actacaaagt tgtttgtatt tttaattact aaatgtaaat    2700
gaaagtacat gcttcatacc cttgttataa tattttagac taaactacca caatggcatg    2760
ttaacttata gcagtaagtt gtaatttatt ttcttttcat tttctcagtt gttacaagaa    2820 cttttttta cttaataaaa aatagtcgta agggcctccc ttgttcggtc aaaaaagaat    2880
tagactaaac tcaatcgtat ttgtacataa acaaaattta aatataact aaaacgaaac    2940 agtgataaaa atggtgcaat ttaactgctg cctcttgttt taatgtctga caatgttgat    3000
tttgtatata tgtttggcca tttattttat tcaattttt tacaaatatg aaaaatataa    3060
tatgtgctta aattacttt aatgataaaa taaatttaag aaaatgataa ttatattttt    3120
aataagatgg atgatctaac atatatatgt ccaaaagttt gacatcaaac attaaaaaca    3180
agagagagta tttgcttagg agtacgtgtc tttttccatg ccttagaaca ggtacaatag    3240
caggttataa gctaggccaa acatatttta aagagatata ggaagagaga gaagagcagc    3300
agcctacaga tctgtagcca gctgcagcac ggactctaag acgtaatgtg tgtatgacag    3360
gtaggaccaa gtattaatag tatagtaagc aactattgta tgaattggct atttggctct    3420
agatgatttg gagctagtag tcggctatac tattaaactt gctcttagat atgtggttaa    3480
atttaatttc tgaaatttac aagatataga acatgtcttc accatgtttg caaagttgat    3540
aaaatgaaat tgcactcaac ttttaaatt cagcatgcta tcccacgtat agcttttaa    3600 atatgattta ttttttcgta cattagaagt ttaatgttta cgaagtacta atgttctgc    3660 aggtacttca tcataattga agatttatgg gcttcatcaa tgtgggatat tgttagccgt    3720
ggtttgcctg ataataatag ttgcagtaga atactaataa caacagaaat tgaacctgta    3780
gctttggcat gctgtggata taactcagag cacattatta agattgatcc actgggtgat    3840
gatgtctcaa gtcaattgtt tttcagtgga gttgttggcc aaggaaatga atttcctgga    3900
catcttactg aagtttctca tgacatgata aaaaaatgtg gtggcttgcc actagcaata    3960
```

-continued

```
actataacag ccagacattt taaaagccag ctgttagatg gaatgcagca atggaatcac    4020
atacaaaaat cattgactac ttccaatttg aagaaaaatc ctactttgca ggggatgagg    4080
caagtactca accttattta caataatctt cctcattgtt tgaaagcatg tctgttatac    4140
cttagcatct acaaagagga ctacataatt aggaaggcca acttggtgag gcaatggatg    4200
gctgaaggtt tcatcaattc catagaaaat aaagtcatgg aagaagttgc agggaactat    4260
tttgatgaac ttgttggtag gggcctggtc caaccagtag atgttaactg caaaaatgag    4320
gtattgtcat gtgtagtgca ccacatggta ttaaatttca tcaggtgtaa gtcaatagag    4380
gagaatttca gcattacatt ggatcattct cagacgacag taagacatgc tgacaaggtt    4440
cgccgactct cgcttcactt cagcaatgca catgatacaa caccactagc aggtttgaga    4500
ctctcacaag ttcgatcgat ggcattttc ggacaagtca agtgtatgcc ttccattgca    4560
gattataggc ttcttcgagt tctgattctt tgttttggg ctgatcaaga gaaacaagc    4620
tatgacctca caagcatttt tgaactgtta caactgagat atctgaagat aacaggtaat    4680
atcacagtta aacttccaga agatccaa ggactacaac acttgcagac actggaagca    4740
gatgcaagag caactgctgt cctattggat attgttcata cacagtgttt gttgcacctt    4800
cgtcttgtac tacttgatct gctccctcac tgtcacaggt acatcttcac cagcatcccc    4860
aaatggactg gaaagctcaa caatctccgc attttaaaca ttgcagtcat gcaaatttcc    4920
caggatgacc ttgacactct caaggactg ggatctctca ctgctctttc gctgcttgtt    4980
cgaacagcgc ctgcgcaaag aatcgtcgct gcgaatgagg ggttcgggtc tctcaagtac    5040
ttcatgtttg tctgtacagc accatgcatg acttttgtgg aaggagcaat gccgagtgtg    5100
caaaggttaa atctaaggtt caatgccaac gagttcaagc agtatgactc taaggagaca    5160
gggttggaac acttggtcgc ccttgcagag atctctgcaa gaattggggg cactgatgat    5220
gatgaatcaa acaaaactga agtggagtct gccttgagga ctgcaattcg caagcatccg    5280
acgccgagca ctcttatggt tgatatacaa tgggtggatt ggatctttgg tgctgaaggg    5340
agagacttgg atgaagattt ggcacaacaa gatgatcacg ggtatggatt tttcattcta    5400
ttcccaggtt acaacttaca aggattattg agcttctttc tttctctgcc gtggcttcta    5460
tctttacctg ctatgcatct tcaacctgac ttgatgattg tttgaaacca atttaatgg    5520
aagttaaatg ttattgttgt gaccctgaat caggttttgt atgctaccgg aatcctcttc    5580
acgtcttcag agtagaggta attttgtttc ttgtcatttt acagttacag ttcatcttct    5640
taaggaatta atgggaggtc ctatattttc tcgggtacct agaaggtgtg gttcctagtc    5700
ttacctcctt aagaaccgta gaatgttggc cctaacactt ggatcaaaga acgaaag      5757
```

<210> SEQ ID NO 2
<211> LENGTH: 928
<212> TYPE: PRT
<213> ORGANISM: Oryza sativa

<400> SEQUENCE: 2

```
Met Ala Pro Ala Val Ile Ala Ser Gln Gly Val Ile Met Arg Ser Leu
  1               5                  10                  15

Thr Ser Lys Leu Asp Ser Leu Leu Gln Pro Glu Pro Pro
             20                  25                  30

Pro Ala Gln Pro Ser Ser Leu Arg Lys Gly Glu Arg Lys Lys Ile Leu
         35                  40                  45

Leu Leu Arg Gly Asp Leu Arg His Leu Leu Asp Asp Tyr Tyr Leu Leu
```

```
              50                  55                  60
Val Glu Pro Pro Ser Asp Thr Ala Pro Pro Asp Ser Thr Ala Ala
65                  70                  75                  80

Cys Trp Ala Lys Glu Val Arg Glu Leu Ser Tyr Asp Val Asp Phe
                85                  90                  95

Leu Asp Glu Leu Thr Thr Gln Leu Leu His His Arg Gly Gly Asp
                100                 105                 110

Gly Ser Ser Thr Ala Gly Ala Lys Lys Met Ile Ser Ser Met Ile Ala
                115                 120                 125

Arg Leu Arg Gly Glu Leu Asn Arg Arg Trp Ile Ala Asp Glu Val
                130                 135                 140

Thr Leu Phe Arg Ala Arg Val Lys Glu Ala Ile Arg Arg His Glu Ser
145                 150                 155                 160

Tyr His Leu Gly Arg Arg Thr Ser Ser Arg Pro Arg Glu Glu Asp
                165                 170                 175

Asp Asp Asp Asp Arg Glu Asp Ser Ala Gly Asn Glu Arg Arg Arg Phe
                180                 185                 190

Leu Ser Leu Thr Phe Gly Met Asp Asp Ala Ala Val His Gly Gln Leu
                195                 200                 205

Val Gly Arg Asp Ile Ser Met Gln Lys Leu Val Arg Trp Leu Ala Asp
                210                 215                 220

Gly Glu Pro Lys Leu Lys Val Ala Ser Ile Val Gly Ser Gly Gly Val
225                 230                 235                 240

Gly Lys Thr Thr Leu Ala Thr Glu Phe Tyr Arg Leu His Gly Arg Arg
                245                 250                 255

Leu Asp Ala Pro Phe Asp Cys Arg Ala Phe Val Arg Thr Pro Arg Lys
                260                 265                 270

Pro Asp Met Thr Lys Ile Leu Thr Asp Met Leu Ser Gln Leu Arg Pro
                275                 280                 285

Gln His Gln His Gln Ser Ser Asp Val Trp Glu Val Asp Arg Leu Leu
                290                 295                 300

Glu Thr Ile Arg Thr His Leu Gln Asp Lys Arg Tyr Phe Ile Ile Ile
305                 310                 315                 320

Glu Asp Leu Trp Ala Ser Ser Met Trp Asp Ile Val Ser Arg Gly Leu
                325                 330                 335

Pro Asp Asn Asn Ser Cys Ser Arg Ile Leu Ile Thr Thr Glu Ile Glu
                340                 345                 350

Pro Val Ala Leu Ala Cys Cys Gly Tyr Asn Ser Glu His Ile Ile Lys
                355                 360                 365

Ile Asp Pro Leu Gly Asp Val Ser Ser Gln Leu Phe Phe Ser Gly
                370                 375                 380

Val Val Gly Gln Gly Asn Glu Phe Pro Gly His Leu Thr Glu Val Ser
385                 390                 395                 400

His Asp Met Ile Lys Lys Cys Gly Gly Leu Pro Leu Ala Ile Thr Ile
                405                 410                 415

Thr Ala Arg His Phe Lys Ser Gln Leu Leu Asp Gly Met Gln Gln Trp
                420                 425                 430

Asn His Ile Gln Lys Ser Leu Thr Thr Ser Asn Leu Lys Lys Asn Pro
                435                 440                 445

Thr Leu Gln Gly Met Arg Gln Val Leu Asn Leu Ile Tyr Asn Asn Leu
                450                 455                 460

Pro His Cys Leu Lys Ala Cys Leu Leu Tyr Leu Ser Ile Tyr Lys Glu
465                 470                 475                 480
```

```
Asp Tyr Ile Ile Arg Lys Ala Asn Leu Val Arg Gln Trp Met Ala Glu
            485                 490                 495
Gly Phe Ile Asn Ser Ile Glu Asn Lys Val Met Glu Val Ala Gly
            500                 505                 510
Asn Tyr Phe Asp Glu Leu Val Gly Arg Gly Leu Val Gln Pro Val Asp
            515                 520                 525
Val Asn Cys Lys Asn Glu Val Leu Ser Cys Val Val His His Met Val
            530                 535                 540
Leu Asn Phe Ile Arg Cys Lys Ser Ile Glu Glu Asn Phe Ser Ile Thr
545                 550                 555                 560
Leu Asp His Ser Gln Thr Thr Val Arg His Ala Asp Lys Val Arg Arg
                565                 570                 575
Leu Ser Leu His Phe Ser Asn Ala His Asp Thr Thr Pro Leu Ala Gly
                580                 585                 590
Leu Arg Leu Ser Gln Val Arg Ser Met Ala Phe Gly Gln Val Lys
            595                 600                 605
Cys Met Pro Ser Ile Ala Asp Tyr Arg Leu Leu Arg Val Leu Ile Leu
            610                 615                 620
Cys Phe Trp Ala Asp Gln Glu Lys Thr Ser Tyr Asp Leu Thr Ser Ile
625                 630                 635                 640
Phe Glu Leu Leu Gln Leu Arg Tyr Leu Lys Ile Thr Gly Asn Ile Thr
                645                 650                 655
Val Lys Leu Pro Glu Lys Ile Gln Gly Leu Gln His Leu Gln Thr Leu
                660                 665                 670
Glu Ala Asp Ala Arg Ala Thr Ala Val Leu Leu Asp Ile Val His Thr
            675                 680                 685
Gln Cys Leu Leu His Leu Arg Leu Val Leu Leu Asp Leu Leu Pro His
            690                 695                 700
Cys His Arg Tyr Ile Phe Thr Ser Ile Pro Lys Trp Thr Gly Lys Leu
705                 710                 715                 720
Asn Asn Leu Arg Ile Leu Asn Ile Ala Val Met Gln Ile Ser Gln Asp
                725                 730                 735
Asp Leu Asp Thr Leu Lys Gly Leu Gly Ser Leu Thr Ala Leu Ser Leu
                740                 745                 750
Leu Val Arg Thr Ala Pro Ala Gln Arg Ile Val Ala Ala Asn Glu Gly
            755                 760                 765
Phe Gly Ser Leu Lys Tyr Phe Met Phe Val Cys Thr Ala Pro Cys Met
            770                 775                 780
Thr Phe Val Glu Gly Ala Met Pro Ser Val Gln Arg Leu Asn Leu Arg
785                 790                 795                 800
Phe Asn Ala Asn Glu Phe Lys Gln Tyr Asp Ser Lys Glu Thr Gly Leu
                805                 810                 815
Glu His Leu Val Ala Leu Ala Glu Ile Ser Ala Arg Ile Gly Gly Thr
            820                 825                 830
Asp Asp Asp Glu Ser Asn Lys Thr Glu Val Glu Ser Ala Leu Arg Thr
            835                 840                 845
Ala Ile Arg Lys His Pro Thr Pro Ser Thr Leu Met Val Asp Ile Gln
850                 855                 860
Trp Val Asp Trp Ile Phe Gly Ala Glu Gly Arg Asp Leu Asp Glu Asp
865                 870                 875                 880
Leu Ala Gln Gln Asp Asp His Gly Tyr Gly Phe Phe Ile Leu Phe Pro
                885                 890                 895
```

| Gly | Tyr | Asn | Leu | Gln | Gly | Leu | Leu | Ser | Phe | Phe | Leu | Ser | Leu | Pro | Trp |
|---|---|---|---|---|---|---|---|---|---|---|---|---|---|---|---|
| | | | | 900 | | | | | 905 | | | | | 910 | |

| Leu | Leu | Ser | Leu | Pro | Ala | Met | His | Leu | Gln | Pro | Asp | Leu | Met | Ile | Val |
|---|---|---|---|---|---|---|---|---|---|---|---|---|---|---|---|
| | | | 915 | | | | 920 | | | | | 925 | | | |

<210> SEQ ID NO 3
<211> LENGTH: 5113
<212> TYPE: DNA
<213> ORGANISM: Oryza sativa

<400> SEQUENCE: 3

```
aattatatag ttaccatcgt acaacgttac tctcaagcga gaaccaagtc gtcatagttc    60
caaagtagga aaagttattc cattaattag ctactcggtc catgcaaaga tcgtaagcat   120
atttatttta tcatcgagac caagaaaaaa aattaactca ttcgatttgt actcccatgt   180
aacaaacttt tcatatgca tgcaaaaggg ttggagaatg catggcagct caagtttcgg   240
tcaacaattt aatcatacac ggtaaaacga aaagagactc tcttcattta aggctcggat   300
gcatggagac tatatgaata agctcatctc atttggaaaa aaataatcaa acaatgaaa   360
tatgcttaat acatttggat ttggatggag tatctcccta tgacgaaaga gacgagggat   420
tgcctacttc tttccacatc aacctttgaa ggctatggca gagctacatt tgcagcgcag   480
cctctctgca tgatttctta ctagatagga ttaagtttca agagttaatt tcttgtactc   540
ttgggcgatc catgctgtca aatcagcaac taacgaggca taatctcgat cactagctct   600
gatctgatct tcagctagcg ccggcgagct gcagaggtct ccatccatgg cgccggcggt   660
cagtgcatcg cagggtgtca tcatgcggtc cctgacgagc aagctcgact cgctgctgct   720
gcagccgccg gagccgccgc cgcctgcgca accgtcgtcg ctgcggaagg gggagaggaa   780
gaagatcctc ctcctcagag gcgatctccg cacctgcta gatgactact acctcctcgt   840
ggagccgccg tcagacaccg cgccaccgcc agactcgacg gcggcgtgct gggctaagga   900
ggttcgcgag ctctcctacg acgtcgacga cttcctcgac gagctaacga cccagctcct   960
ccaccaccgc ggcggcggcg atggcagtag cactgctggt gccaagaaga tgatcagcag  1020
catgatcgcc cggcttcgag gggagcttaa ccggcggcgg tggatcgccg acgaggtcac  1080
cctgttcagc gcccgcgtga aggaggccat tcgccgccac gagagctacc atcttggcag  1140
gcgcacctcg agctcgaggc cgagagaaga agtcgacgac gacgatcgcg aggactccgc  1200
cggcaacgaa cgccgccggt ttctgtcgct gacgttcggg atggacgacg ctgctgtgca  1260
cggccagctc gttggtaggg atatttcgat gcaaaagctc gtccggtggc tggccgacgg  1320
cgagccgaag ctcaaggtgg cttccattgt tggatccgga ggtgttggca agacgacgct  1380
ggccacagaa ttctatcgtc tgcatggccg gcggttggat gcgccgttcg actgccgggc  1440
tttcgtgcgg acgccccgga agcctgacat gacgaagatc ctcaccgaca tgctgtcaca  1500
gctgcggcca caacatcagc atcagtcttc ggatgtttgg gaggttgatc gactccttga  1560
aactatccgg acgcatttgc aagataaaag gtaattcatg tctacatcta tctctagtat  1620
ttttttcatg aatttacaaa ctattttctc aaatttcccc ttttttatcc ttcatatagt  1680
aattaagtta gtaactatac atatgaattt aatttactcg acaatgccaa taatatttta  1740
aattactttt atagtgcccc tctattatta aatacaattc gatcgagcca tgaatcatac  1800
tggtaatcta aacaattatt atacccacct cattctacta acagcaattg agttgttaat  1860
ataaatagat atggtctatt gcatgaaaaa ataaggtaa agtgtttaca ttatttctac  1920
tactagtagc agaactacaa agttgtttgt atttttaatt attaaatgta aatgaaagta  1980
```

```
catgtttcat accettgtta ttttttagg cgactaaact actagtacat tatttctact   2040
actagtagaa caactacaaa gttgtttgta tttttaatta ctaaatgtaa atgaaagtac   2100
atgcttcata cccttgttat aatattttag actaaactac cacaatggca tgttaactta   2160
tagcagtaag ttgtaattta ttttcttttc attttctcag ttgttacaag aactttttt    2220
tacttaataa aaaatagtcg taagggcctc ccttgttcgg tcaaaaaga attagactaa    2280
actcaatcgt atttgtacat aaacaaaatt taaaatataa ctaaaacgaa acagtgataa   2340
aaatggtgca atttaactgc tgcctcttgt tttaatgtct gacaatgttg attttgtata   2400
tatgtttggc catttatttt attcaaattt tttacaaata tgaaaaatat aatatatgct   2460
taaattactt ttaatgataa aataaattta aaaaaatgat aattatattt ttaataagat   2520
ggatgatcta acatatatat gtccaaaagt ttgacatcaa acattaaaaa caagagagag   2580
tatttgctta ggagtacgtg tctttttcca tgtctaagaa caggtacaat agcaggttat   2640
aagctagcta taaacatatt ttaaagagat ataggaagag agagaagagc agcagcctac   2700
agatctgtag ccagctgcag cacggactct aagacgtaat gtgtgtatga caggtaggac   2760
caagtattaa tagtatagta agcaactatt gtatgaattg gctatttggc tctagatgat   2820
ttggagctag tagtcggcta tactattaaa cttgctctta gatatgtggt taaatttaat   2880
ttctgaaatt tacaagatat agaacatgtc ttcaccatgt ttgcaaagtt gataaaatga   2940
aattgcactc aactttttaa attcagcatg ctatcccacg tatagctttt taaatatgat   3000
ttatttttc gtacattaga agtttaatgt ttacgaagta ctaaatgttc tgcaggtact    3060
tcatcataat tgaagattta tgggcttcat caatgtggga tattgttagc cgtggtttgc   3120
ctgataataa tagttgcagt agaatactaa taacaacaga aattgaacct gtagctttgg   3180
catgctgtgg atataactca gagcacatta ttaagattga tccactgggt gatgatgtct   3240
caagtcaatt gttttttcagt ggagttgttg gccaaggaaa tgaatttcct ggacatctta  3300
ctgaagtttc tcatgacatg ataaaaaaat gtggtggctt gccactagca ataactataa   3360
cagccagaca ttttaaaagc cagctgttag atggaatgca gcaatggaat cacatacaaa   3420
aatcattgac tacttccaat ttgaagaaaa atcctacttt gcaggggatg aggcaagtac   3480
tcaaccttat ttacaataat cttcctcatt gtttgaaagc atgtctgtta taccttagca   3540
tctacaaaga ggactacata attaggaagg ccaacttggt gaggcaatgg atggctgaag   3600
gtttcatcaa ttccatagaa aataaagtca tggaagaagt tgcagggaac tatttttgatg  3660
aacttgttgg tagggcctg gtccaaccag tagatgttaa ctgcaaaaat gaggtattgt    3720
catgtgtagt gcaccacatg gtattaaatt tcatcaggtg taagtcaata gaggagaatt   3780
tcagcattac attggatcat tctcagacga cagtaagaca tgctgacaag gttcgccgac   3840
tctcgcttca cttcagcaat gcacatgata caacaccact agcaggtttg agactctcac   3900
aagttcgatc gatggcattt ttcggacaag tcaagtgtat gccttccatt gcagattata   3960
ggcttcttcg agttctgatt ctttgttttt gggctgatca agagaaaaca agctatgacc   4020
tcacaagcat ttttgaactg ttacaactga gatatctgaa gataacaggt aatatcacag   4080
ttaaacttcc agagaagatc caaggactac aacacttgca gacactggaa gcagatgcaa   4140
gagcaactgc tgtcctattg gatattgttc atacacagtg tttgttgcac cttcgtcttg   4200
tactacttga tctgctcct cactgtcaca ggtacatctt caccagcatc cccaaatgga    4260
ctggaaagct caacaatctc cgcattttaa acattgcagt catgcaaatt tcccaggatg   4320
```

-continued

```
accttgacac tctcaaagga ctgggatctc tcactgctct ttcgctgctt gttcgaacag    4380
cgcctgcgca aagaatcgtc gctgcgaatg aggggttcgg gtctctcaag tacttcatgt    4440
ttgtctgtac agcaccatgc atgacttttg tggaaggagc aatgccgagt gtgcaaagat    4500
taaatctaag gttcaatgcc aacgagttca agcagtatga ctctaaggag acagggttgg    4560
aacacttggt cgcccttgca gagatctctg caagaattgg gggcactgat gatgatgaat    4620
caaacaaaac tgaagtggag tctgccttga ggactgcaat tcgcaagcat ccgacgccga    4680
gcactcttat ggttgatata caatgggtgg attggatctt tggtgctgaa gggagagact    4740
tggatgaaga tttggcacaa caagatgatc acgggtatgg attttcatt ctattcccag    4800 gttacaactt acaaggatta ttgagcttct ttctttctct gccgtggctt ctatctttac    4860
cttctatgca tcttcaacct gacttgatga ttgtttgaaa ccaattttaa tggaagttaa    4920
atgttattgt tgtgaccctg aatcaggttt tgtatgctac cggaatcctc ttcacgtctt    4980
cagagtagag gtaattttgt ttcttgtcat tttacagtta cagttcatct acttaaggaa    5040
ttaatgggag gtcctatatt ttctcgggta cctagaaggt gtggttccta gtcttacctc    5100
cttaagaacc gta                                                      5113
```

<210> SEQ ID NO 4
<211> LENGTH: 928
<212> TYPE: PRT
<213> ORGANISM: Oryza sativa

<400> SEQUENCE: 4

```
Met Ala Pro Ala Val Ser Ala Ser Gln Gly Val Ile Met Arg Ser Leu
 1               5                  10                  15

Thr Ser Lys Leu Asp Ser Leu Leu Gln Pro Glu Pro Pro Pro
            20                  25                  30

Pro Ala Gln Pro Ser Ser Leu Arg Lys Gly Glu Arg Lys Lys Ile Leu
        35                  40                  45

Leu Leu Arg Gly Asp Leu Arg His Leu Leu Asp Asp Tyr Tyr Leu Leu
    50                  55                  60

Val Glu Pro Pro Ser Asp Thr Ala Pro Pro Asp Ser Thr Ala Ala
65                  70                  75                  80

Cys Trp Ala Lys Glu Val Arg Glu Leu Ser Tyr Asp Val Asp Asp Phe
                85                  90                  95

Leu Asp Glu Leu Thr Thr Gln Leu Leu His His Arg Gly Gly Asp
            100                 105                 110

Gly Ser Ser Thr Ala Gly Ala Lys Lys Met Ile Ser Ser Met Ile Ala
        115                 120                 125

Arg Leu Arg Gly Glu Leu Asn Arg Arg Trp Ile Ala Asp Glu Val
    130                 135                 140

Thr Leu Phe Ser Ala Arg Val Lys Glu Ala Ile Arg Arg Gln Glu Ser
145                 150                 155                 160

Tyr His Leu Gly Arg Arg Thr Ser Ser Arg Pro Arg Glu Glu Val
                165                 170                 175

Asp Asp Asp Asp Arg Glu Asp Ser Ala Gly Asn Glu Arg Arg Arg Phe
            180                 185                 190

Leu Ser Leu Thr Phe Gly Met Asp Asp Ala Ala Val His Gly Gln Leu
        195                 200                 205

Val Gly Arg Asp Ile Ser Met Gln Lys Leu Val Arg Trp Leu Ala Asp
    210                 215                 220

Gly Glu Pro Lys Leu Lys Val Ala Ser Ile Val Gly Ser Gly Gly Val
```

-continued

```
           225                 230                 235                 240
Gly Lys Thr Thr Leu Ala Thr Glu Phe Tyr Arg Leu His Gly Arg Arg
                245                 250                 255
Leu Asp Ala Pro Phe Asp Cys Arg Ala Phe Val Arg Thr Pro Arg Lys
                260                 265                 270
Pro Asp Met Thr Lys Ile Leu Thr Asp Met Leu Ser Gln Leu Arg Pro
                275                 280                 285
Gln His Gln His Gln Ser Ser Asp Val Trp Glu Val Asp Arg Leu Leu
                290                 295                 300
Glu Thr Ile Arg Thr His Leu Gln Asp Lys Arg Tyr Phe Ile Ile Ile
305                 310                 315                 320
Glu Asp Leu Trp Ala Ser Ser Met Trp Asp Ile Val Ser Arg Gly Leu
                325                 330                 335
Pro Asp Asn Asn Ser Cys Ser Arg Ile Leu Ile Thr Thr Glu Ile Glu
                340                 345                 350
Pro Val Ala Leu Ala Cys Cys Gly Tyr Asn Ser Glu His Ile Ile Lys
                355                 360                 365
Ile Asp Pro Leu Gly Asp Asp Val Ser Ser Gln Leu Phe Phe Ser Gly
                370                 375                 380
Val Val Gly Gln Gly Asn Glu Phe Pro Gly His Leu Thr Glu Val Ser
385                 390                 395                 400
His Asp Met Ile Lys Lys Cys Gly Gly Leu Pro Leu Ala Ile Thr Ile
                405                 410                 415
Thr Ala Arg His Phe Lys Ser Gln Leu Leu Asp Gly Met Gln Gln Trp
                420                 425                 430
Asn His Ile Gln Lys Ser Leu Thr Thr Ser Asn Leu Lys Lys Asn Pro
                435                 440                 445
Thr Leu Gln Gly Met Arg Gln Val Leu Asn Leu Ile Tyr Asn Asn Leu
                450                 455                 460
Pro His Cys Leu Lys Ala Cys Leu Leu Tyr Leu Ser Ile Tyr Lys Glu
465                 470                 475                 480
Asp Tyr Ile Ile Arg Lys Ala Asn Leu Val Arg Gln Trp Met Ala Glu
                485                 490                 495
Gly Phe Ile Asn Ser Ile Glu Asn Lys Val Met Glu Val Ala Gly
                500                 505                 510
Asn Tyr Phe Asp Glu Leu Val Gly Arg Gly Leu Val Gln Pro Val Asp
                515                 520                 525
Val Asn Cys Lys Asn Glu Val Leu Ser Cys Val Val His Met Val
                530                 535                 540
Leu Asn Phe Ile Arg Cys Lys Ser Ile Glu Glu Asn Phe Ser Ile Thr
545                 550                 555                 560
Leu Asp His Ser Gln Thr Thr Val Arg His Ala Asp Lys Val Arg Arg
                565                 570                 575
Leu Ser Leu His Phe Ser Asn Ala His Asp Thr Thr Pro Leu Ala Gly
                580                 585                 590
Leu Arg Leu Ser Gln Val Arg Ser Met Ala Phe Gly Gln Val Lys
                595                 600                 605
Cys Met Pro Ser Ile Ala Asp Tyr Arg Leu Leu Arg Val Leu Ile Leu
610                 615                 620
Cys Phe Trp Ala Asp Gln Glu Lys Thr Ser Tyr Asp Leu Thr Ser Ile
625                 630                 635                 640
Phe Glu Leu Leu Gln Leu Arg Tyr Leu Lys Ile Thr Gly Asn Ile Thr
                645                 650                 655
```

Val Lys Leu Pro Glu Lys Ile Gln Gly Leu Gln His Leu Gln Thr Leu
            660                 665                 670

Glu Ala Asp Ala Arg Ala Thr Ala Val Leu Leu Asp Ile Val His Thr
        675                 680                 685

Gln Cys Leu Leu His Leu Arg Leu Val Leu Leu Asp Leu Leu Pro His
    690                 695                 700

Cys His Arg Tyr Ile Phe Thr Ser Ile Pro Lys Trp Thr Gly Lys Leu
705                 710                 715                 720

Asn Asn Leu Arg Ile Leu Asn Ile Ala Val Met Gln Ile Ser Gln Asp
                725                 730                 735

Asp Leu Asp Thr Leu Lys Gly Leu Gly Ser Leu Thr Ala Leu Ser Leu
            740                 745                 750

Leu Val Arg Thr Ala Pro Ala Gln Arg Ile Val Ala Ala Asn Glu Gly
        755                 760                 765

Phe Gly Ser Leu Lys Tyr Phe Met Phe Val Cys Thr Ala Pro Cys Met
    770                 775                 780

Thr Phe Val Glu Gly Ala Met Pro Ser Val Gln Arg Leu Asn Leu Arg
785                 790                 795                 800

Phe Asn Ala Asn Glu Phe Lys Gln Tyr Asp Ser Lys Glu Thr Gly Leu
                805                 810                 815

Glu His Leu Val Ala Leu Ala Glu Ile Ser Ala Arg Ile Gly Gly Thr
            820                 825                 830

Asp Asp Asp Glu Ser Asn Lys Thr Glu Val Glu Ser Ala Leu Arg Thr
        835                 840                 845

Ala Ile Arg Lys His Pro Thr Pro Ser Thr Leu Met Val Asp Ile Gln
    850                 855                 860

Trp Val Asp Trp Ile Phe Gly Ala Glu Gly Arg Asp Leu Asp Glu Asp
865                 870                 875                 880

Leu Ala Gln Gln Asp Asp His Gly Tyr Gly Phe Phe Ile Leu Phe Pro
                885                 890                 895

Gly Tyr Asn Leu Gln Gly Leu Leu Ser Phe Phe Leu Ser Leu Pro Trp
            900                 905                 910

Leu Leu Ser Leu Pro Ser Met His Leu Gln Pro Asp Leu Met Ile Val
        915                 920                 925

<210> SEQ ID NO 5
<211> LENGTH: 672
<212> TYPE: DNA
<213> ORGANISM: Magnaporthe grisea

<400> SEQUENCE: 5 atgcttttt attcattatt ttttttcac accgttgcga tttcggcctt caccaacatt      60 ggcaccttt cacacccagt ttacgattac aatccaattc caaaccatat ccacggagat    120 ttaaaaggc gggcttatat tgaacgctat tcccaatgtt cagattcgca ggcctccgaa    180
attcgtgccg cgctaaaaag ttgtgccgag ctcgcctcgt gggctatca cgccgttaaa    240 aatgacaatc ggttatttag attaatcttt aaaactgaca gcacagatat tcaaaactgg    300
gttcaaaaga attttaacga aatttacaag gaatgtaaca gggacgcgga cgaaatttct    360
ctaacctgcc acgataaaaa tgtttatacg tgcgtccgag aaggagttca taatttggcg    420
tatgcactta ttaacgaaaa agaaattgtt atatgccctc ctttcttcaa caaccccgta    480
aacagcaggg aaattactgc cggtaaccaa gatacagtta tattacatga atggtgcat    540 ataattttaa aagagtggaa agattatggt tacgaatggg atggattca caaattggat    600

-continued

```
agtacagaaa gtattaaaaa ccccgacagt tatgctattt ttgcacaatg tgcacgttat    660
aaatattgtt aa                                                        672
```

<210> SEQ ID NO 6
<211> LENGTH: 223
<212> TYPE: PRT
<213> ORGANISM: Magnaporthe grisea

<400> SEQUENCE: 6

```
Met Leu Phe Tyr Ser Leu Phe Phe His Thr Val Ala Ile Ser Ala
 1               5                  10                  15

Phe Thr Asn Ile Gly Thr Phe Ser His Pro Val Tyr Asp Tyr Asn Pro
             20                  25                  30

Ile Pro Asn His Ile His Gly Asp Leu Lys Arg Ala Tyr Ile Glu
         35                  40                  45

Arg Tyr Ser Gln Cys Ser Asp Ser Gln Ala Ser Glu Ile Arg Ala Ala
 50                  55                  60

Leu Lys Ser Cys Ala Glu Leu Ala Ser Trp Gly Tyr His Ala Val Lys
 65                  70                  75                  80

Asn Asp Asn Arg Leu Phe Arg Leu Ile Phe Lys Thr Asp Ser Thr Asp
             85                  90                  95

Ile Gln Asn Trp Val Gln Lys Asn Phe Asn Glu Ile Tyr Lys Glu Cys
            100                 105                 110

Asn Arg Asp Ala Asp Glu Ile Ser Leu Thr Cys His Asp Lys Asn Val
        115                 120                 125

Tyr Thr Cys Val Arg Glu Gly Val His Asn Leu Ala Tyr Ala Leu Ile
    130                 135                 140

Asn Glu Lys Glu Ile Val Ile Cys Pro Pro Phe Phe Asn Asn Pro Val
145                 150                 155                 160

Asn Ser Arg Glu Ile Thr Ala Gly Asn Gln Asp Thr Val Ile Leu His
                165                 170                 175

Glu Met Val His Ile Ile Leu Lys Glu Trp Lys Asp Tyr Gly Tyr Glu
            180                 185                 190

Trp Asp Gly Ile His Lys Leu Asp Ser Thr Glu Ser Ile Lys Asn Pro
        195                 200                 205

Asp Ser Tyr Ala Ile Phe Ala Gln Cys Ala Arg Tyr Lys Tyr Cys
    210                 215                 220
```

<210> SEQ ID NO 7
<211> LENGTH: 675
<212> TYPE: DNA
<213> ORGANISM: Magnaporthe grisea

<400> SEQUENCE: 7

```
atgctttttt attcatttat attttatttt cacaccgttg caatttcggc cttcaccaac     60
attggcacct ttcatacccc agtttacatt tacaatccaa ttccaaacca tatccacgga    120
gatttaaaaa ggcgggctta tattgaaccc tattcccaat gttcaaattc gcaggactcc    180
gaaattcgtg ccgcgctaaa aagttgtgcc gaactcgcct cgtgggccta tcacgccgtt    240
gaaaatgaca atcggttatt tgaattgatt tttaaaactg acagcacaaa tattaaaaac    300
tgggttcaaa ataattttaa cgaaattcac aaggaatgta acaggacgc ggacgaaatt     360 tctctatcct gccacgatac aagtgtttat acgtgcgtcc gagaaggagt tcatctttg     420 ggctatgcaa agatgtacga aaaacaagtt gttttatgcc ctcatttctt tgatcacccc    480
```

```
gtaaacagca gggaaatcac tgcccaaaac caagatacag ttatattgca tgaaatgctg    540
catataattc taaatgagtg ggaagattat ggttacgaat gggatgggat tcacaatttg    600
gatagtacaa caagtattaa aaaccccgac agctatgcta tttttgcaca atgtgcacgt    660
tataaatatt gttaa                                                     675
```

<210> SEQ ID NO 8
<211> LENGTH: 224
<212> TYPE: PRT
<213> ORGANISM: Magnaporthe grisea

<400> SEQUENCE: 8

```
Met Leu Phe Tyr Ser Phe Ile Phe Tyr Phe His Thr Val Ala Ile Ser
 1               5                  10                  15

Ala Phe Thr Asn Ile Gly Thr Phe Ser Tyr Pro Val Tyr Ile Tyr Asn
             20                  25                  30

Pro Ile Pro Asn His Ile His Gly Asp Leu Lys Arg Arg Ala Tyr Ile
         35                  40                  45

Glu Pro Tyr Ser Gln Cys Ser Asn Ser Gln Asp Ser Glu Ile Arg Ala
     50                  55                  60

Ala Leu Lys Ser Cys Ala Glu Leu Ala Ser Trp Ala Tyr His Ala Val
 65                  70                  75                  80

Glu Asn Asp Asn Arg Leu Phe Glu Leu Ile Phe Lys Thr Asp Ser Thr
                 85                  90                  95

Asn Ile Lys Asn Trp Val Gln Asn Asn Phe Asn Glu Ile His Lys Glu
            100                 105                 110

Cys Asn Arg Asp Ala Asp Glu Ile Ser Leu Ser Cys His Asp Thr Ser
        115                 120                 125

Val Tyr Thr Cys Val Arg Glu Gly Val His Leu Leu Gly Tyr Ala Lys
    130                 135                 140

Met Tyr Glu Lys Gln Val Val Leu Cys Pro His Phe Phe Asp His Pro
145                 150                 155                 160

Val Asn Ser Arg Glu Ile Thr Ala Gln Asn Gln Asp Thr Val Ile Leu
                165                 170                 175

His Glu Met Leu His Ile Ile Leu Asn Glu Trp Glu Asp Tyr Gly Tyr
            180                 185                 190

Glu Trp Asp Gly Ile His Asn Leu Asp Ser Thr Thr Ser Ile Lys Asn
        195                 200                 205

Pro Asp Ser Tyr Ala Ile Phe Ala Gln Cys Ala Arg Tyr Lys Tyr Cys
    210                 215                 220
```

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence:Synthetic
      oligonucleotide
<400> SEQUENCE: 9

```
tcagcgcct                                                              9
```

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide
<400> SEQUENCE: 10
ccaatcggac 10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 11
taatgggcgg 10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 12
gtcgctactg 10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 13
acagcgcctt 10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 14
aggcgtcttc 10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 15
tagccagacc 10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 16

```
tctatgcccc                                                          10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 17
atggcagatg                                                          10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 18
cgagtcaact                                                          10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 19
gtagaagcct                                                          10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 20
tcatgcggag                                                          10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 21
ccatttccgt                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 22
gggaggactt                                                          10
```

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 23
aaaggcagtg                                                                 10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 24
tgtgcaacgg                                                                 10

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 25
gtaaaacgac ggccagt                                                         17

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 26
ggaaacagct atgaccatg                                                       19

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 27
gtaatacgac tcactatagg gc                                                   22

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 28
atttaggtga cactatag                                                        18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 29
tttgtgatgg cttccatgtc                                          20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 30
gtcgactcta gaggatcc                                            18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 31
gtcgactcta gaggatcc                                            18

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 32
aggcgtcttc agttttgtaa ta                                       22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 33
aggcgtcttc cggaaagcag cg                                       22

<210> SEQ ID NO 34
<211> LENGTH: 586
<212> TYPE: DNA
<213> ORGANISM: Oryza sativa
<220> FEATURE:
<221> NAME/KEY: unsure
<222> LOCATION: (522)
<221> NAME/KEY: unsure
<222> LOCATION: (583)

<400> SEQUENCE: 34
aatgaggaag attattgtaa ataaggttga gtacttgcct catcccctgc aaagtaggat    60

-continued

```
ttttcttcaa attggaagta gtcaatgatt tttgtatgtg attccattgc tgcattccat      120
ctaacagctg gcttttaaaa tgtctggctg ttatagttat tgctagtggc aagccaccac      180 attttttttat catgtcatga gaaacttcag taagatgtcc aggaaattca tttccttggc     240
caacaactcc actgaaaaac aattgacttg agacatcatc acccagtgga tcaatcttaa      300
taatgtgctc tgagttatat ccacagcatg ccaaagctac aggttcaatt tctgttgtta      360
ttagtattct actgcaacta ttattatcag gcaaaccacg gctaacaata tcccacattg      420
atgaagccca taaatcttca attatgatga agtacctgca gaacatttag tacttcgtaa      480
acattaaact tctaatgtac gaaaaaataa atctatttaa anagctatac gtgggatagc      540
atgctgaatt taaaaagttg agtgccattt catttatcac ctntgc                     586
```

<210> SEQ ID NO 35
<211> LENGTH: 598
<212> TYPE: DNA
<213> ORGANISM: Oryza sativa

<400> SEQUENCE: 35

```
accttccagt gtctgcaagt gttgtagtcc ttggatcttc tctggaagtt taactgtgat      60
attacctgtt atcttcagat atctcagttg taacagttca gaaatgcttg tgaggtcata     120
gcttgttttc tcttgatcag cccaaaaaca aagaatcaga actcgaagaa gcctataatc     180
tgcaatggaa ggcatacact tgacttgtcc gaaaaatgcc atcgatcgaa cttgtgagag     240
tctcaaacct gctagtggtg ttgtatcatg tgcattgctg aagtgaagcg agagtcggcg     300
aaccttgtca gcatgtctta ctgtcgtctg agaatgatcc aatgtaatgc tgaaattctc     360
ctctattgac ttacacctga tgaaatttaa taccatgtgg tgcactacac atgacaatac     420
ctcatttttg cagttaacat ctactggttg gaccaggccc ctaccaacaa gttcatcaaa     480
tagttccctg caacttcttc catgacttta ttttctatgg aattgatgaa accttcagcc     540
atccattgcc tcaccaagtt ggccttccta attatggagt cctcttgtag atgccaag      598
```

<210> SEQ ID NO 36
<211> LENGTH: 605
<212> TYPE: DNA
<213> ORGANISM: Oryza sativa
<220> FEATURE:
<221> NAME/KEY: unsure
<222> LOCATION: (601)

<400> SEQUENCE: 36

```
ataataattg tttagattac cagtataatt catggctcga tcgaatcgta tctactaata     60
gaggacacta taaagtaatt ttaaaatatt attggcattg tcgagtaaat taaattcata    120
tgtatagtta ctaacttaat tactatatga aggataaaaa aggggaaatt tgagaaaata    180
gtttgtaaat tcatgaaaaa aatactagag atagatgtag acatgaatta cctttttatct   240 tgcaaatgcg tccggatagt ttcaaggagt cgatcaacct cccaaacatc cgaagactga    300
tgctgatgtt gtggccgcag ctgtgacagc atgtcggtga ggatcttcgt catgtcaggc    360
ttccggggcg tccgcacgaa agcccggcag tcgaacggcg catccaaccg ccggccatgc    420
agacgataga attctgtggc cagcgtcgtc ttgccaacac ctccggatcc aacaatggaa    480
gccaccttga gcttcggctc gccgtcggcc agccaccgga cgagcttttg catcgaaata    540
tccctaccaa cgagctggcc gtgcacagca gcgtcgtcca tcccgaacgt cagcgacaga    600 naccg                                                                 605
```

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 37
ccatcggtga ccatggg                                                    17

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 38
ccctctccgt tgttcccatg g                                               21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 39
gggttggaga atgcatgg                                                   18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 40
ccatgcattc tccaaccc                                                   18

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 41
catggatgga gacctctgc                                                  19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 42
tcctcagagg cgatctcc                                                   18

```
<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 43
gaacagggtg acctcgtcg                                                    19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 44
gtggcttcca ttgttggatc                                                   20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 45
cgaacggcgc atccaacc                                                     18

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 46
gtgtcctcta ttagtaaata c                                                 21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 47
gtatttacta atagaggaca c                                                 21

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 48
gggcctccct tgttcgg                                                      17
```

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 49
ccgaacaagg gaggccc                                                    17

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 50
cctacagatc tgtagccagc                                                 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 51
gctggctaca gatctgtagg                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 52
gctggctaca gatctgtagg                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 53
gctggctaca gatctgtagg                                                 20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 54
gtgattccat tgctgcattc c                                               21

<210> SEQ ID NO 55

<211> LENGTH: 21
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 55
catgtgtagt gcaccacatg g          21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 56
ctgtcgtctg agaatgatcc          20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 57
ccaaggacta caacacttgc          20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 58
gcatccccaa atggactgg          19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 59
ccagtccatt tggggatgc          19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 60
caagcatccg acgccgagc          19

<210> SEQ ID NO 61
<211> LENGTH: 23

```
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 61
ttgtatatca accataagag tgc                                               23

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 62
gttctttgat ccaagtgtta gg                                                22

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 63
cattaaagtc gacctcaaac aatcatcaag tcaggt                                 36

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 64
aatgcagaat tcacaacacc actagcaggt ttg                                    33

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 65
ccattaagct tggtttcaaa caatc                                             25

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 66
acaacaagcc ggcacgtgcc atggaacgct                                        30

<210> SEQ ID NO 67
<211> LENGTH: 24
<212> TYPE: DNA
```

<213> ORGANISM: Artificial Sequence
<220> FEATURE:
<223> OTHER INFORMATION: Description of Artificial Sequence:Synthetic
      oligonucleotide

<400> SEQUENCE: 67 tccttctttta ggtaccgctc tctc                                           24

<210> SEQ ID NO 68
<211> LENGTH: 5222
<212> TYPE: DNA
<213> ORGANISM: Oryza sativa

<400> SEQUENCE: 68
gaattctaag caaaactctc ctccaatgct cccttttcttt ttcaagttct cgttgggcaa      60
ctttatcaat tgtttgattc ttttgcatcc taagacgcaa ttcataccat gtggacatat     120
ttgtgacatg ctctctacta attcatgctc tttaagtcta ttagcaagat gattccagtc     180
attgacaccg tcatttgtta gctgacttct cacaagcccc tttctcaata atttgcaaca     240 aaacaaaat actttgtcaa gctctttgct gtaaacaagc cattccctgt cacacttctc      300
tccatttgag agaactttag tgtatgatga tgcaagaaac cttctagaca aattgtctct     360
gggaccatgc tcaatagaca aatctctttt agggcccttt tgcaataaaa tatcaatcat     420
tttaggatca agtccatccc aagttcttgg atcaaacata tcaggtcgaa agaaacatt      480 atcgtcggcg tcgtcagcaa tattttcctc attaccttca ctggcaagat cacggccttc     540
atcggcaaga tcatggccaa tgtctccatc aacatttttcc tctactgcgt catcactttc     600
ggcaatatta gcatcaacct ctgccatatc atcactaata tcgtcttcaa tattagcatt     660
tggagtttct ctcaaaaaaa atttatcaag agcacccttt tgagattgag ctactgcttc     720
tagtcttctt ctcttctggc gttttcagc gccagaatca tacttcctat ttctagagga     780
catgatcgct tcacttgatg aattgaggat tgaccgaccg aactgctata gtactgtatt     840
ctttctgttt aataaaaaac taaagtaact tcagtgattt taatcaaaca tgaactgatc     900
aattaaattt aatttaattt acattgtaca tttgtactca caaagtcaca atggagaaca     960
ggagaagccg agaaggtccg acggcagcgg cggcgtggcg tcggcggcgg cggtggcgcg   1020
gacggcagcg gcggcacggc gtcggccgga cggcagcggc gttcggctcg gctgcctgga   1080
ttggatggcg aggcgacgag acgacgaggc ggcgagagcg ctaggagcct agggctgcga   1140
gtcgtgcgat gcgaggacag aaaccgaagc gatgccgtcg tatactcgta tgctgctgcc   1200
ttctatcgat cgatcaaact cccgagtccc gagtccgagt cgcgtacgcg tgccggcgtg   1260
cggcgccgtg tgcgtccgca gttcgcaggc cgcacgctcg gctgggctgg ctctagtcct   1320
actgggcttc tcgcaggtgg gggcccctgg aaattggggg cccccctgcga tcgcccagct   1380 cgctctccgc gatcgacggg cctgggtagt tagcaccttg atcctggtta ccactacctc   1440
tcgagtagat ggcatctact cgagaggtag tggcagccaa gaattaacaa cataggccgg   1500
tgatgacgag ggagacagca ccatcggtga ccatgggaac aagggagagg gcattaatgg   1560
aagtgttgct aacccaaagc tactactatg aagataagta ctgtaggatt agtactctca   1620
actcagtggc atgcttttat ccaaaaggct acaatcaaga gttgcttcca gggcaaatgc   1680
ccttagttat gctttttttt tttaatcccc aatgggctct cctctgtaga attttcttcc   1740
aactttatcc tctttggagt ttggcctaac ctaacatcta attatatagt taccatcgta   1800
caacgttact ctcaagcgag aaccaagtcg tcatagttcc aaagtaggaa aagttattcc   1860

```
attaattagc tactcggtcc atgcaaagat cgtaagcata tttattttat catcgagacc    1920
aagaaaaaaa attaactcat tcgatttgta ctcccatgta acaaactttt tcatatgcat    1980
gcaaaagggt tggagaatgc atggcagctc aagtttcggt caacaattta atcatacacg    2040
gtaaaacgaa aagagactct cttcatttaa ggctcggatg catggagact atatgaataa    2100
gctcatctca tttggaaaaa aataatcaaa acaatgaaat atgcttaata catttggatt    2160
tggatggagt atctccctat gacgaaagag acgagggatt gcctacttct ttccacatca    2220
acctttgaag gctatggcag agctacattt gcagcgcagc ctctctgcat gatttcttac    2280
tagataggat taagtttcaa gagttaattt cttgtactct tgggcgatcc atgctgtcaa    2340
atcagcaact aacgaggcat aatctcgatc actagctctg atctgatctt cagctagcgc    2400
cggcgagctg cagaggtctc catccatggc gccggcggtc attgcatcgc agggtgtcat    2460
catgcggtcc ctgacgagca agctcgactc gctgctgctg cagccgccgg agccgccgcc    2520
gcctgcgcaa ccgtcgtcgc tgcggaaggg ggagaggaag aagatcctcc tcctcagagg    2580
cgatctccga cacctgctag atgactacta cctcctcgtg gagccgccgt cagacaccgc    2640
gccaccgcca gactcgacgg cggcgtgctg ggctaaggag gttcgcgagc tctcctacga    2700
cgtcgacgac ttcctcgacg agctaacgac ccagctcctc caccaccgcg gcggcggcga    2760
tggcagtagc actgctggtg ccaagaagat gatcagcagc atgatcgcgc ggcttcgagg    2820
ggagcttaac cggcggcggt ggatcgccga cgaggtcacc ctgttcaggg cccgcgtgaa    2880
ggaggccatt cgccgccacg agagctacca tcttggcagg cgcacctcga gctcgaggcc    2940
gagagaagaa gacgacgacg acgatcgcga ggactccgcc ggcaacgaac gccgccggtt    3000
tctgtcgctg acgttcggga tggacgacgc tgctgtgcac ggccagctcg ttggtaggga    3060
tatttcgatg caaaagctcg tccggtggct ggccgacggc gagccgaagc tcaaggtggc    3120
ttccattgtt ggatccggag gtgttggcaa gacgacgctg gccacagaat tctatcgtct    3180
gcatggccgg cggttggatg cgccgttcga ctgccgggct tcgtgcgga cgccccggaa    3240
gcctgacatg acgaagatcc tcaccgacat gctgtcacag ctgcggccac aacatcagca    3300
tcagtcttcg gatgtttggg aggttgatcg actccttgaa actatccgga cgcatttgca    3360
agataaaagg tacttcatca taattgaaga tttatgggct tcatcaatgt gggatattgt    3420
tagccgtggt ttgcctgata ataatagttg cagtagaata ctaataacaa cagaaattga    3480
acctgtagct ttggcatgct gtggatataa ctcagagcac attattaaga ttgatccact    3540
gggtgatgat gtctcaagtc aattgttttt cagtggagtt gttggccaag gaaatgaatt    3600
tcctggacat cttactgaag tttctcatga catgataaaa aaatgtggtg gcttgccact    3660
agcaataact ataacagcca gacattttaa aagccagctg ttagatggaa tgcagcaatg    3720
gaatcacata caaaaatcat tgactacttc caatttgaag aaaaatccta ctttgcaggg    3780
gatgaggcaa gtactcaacc ttatttacaa taatcttcct cattgtttga agcatgtct    3840
gttataccct agcatctaca aagaggacta cataattagg aaggccaact tggtgaggca    3900
atggatggct gaaggtttca tcaattccat agaaaataaa gtcatggaag aagttgcagg    3960
gaactatttt gatgaacttg ttggtagggg cctggtccaa ccagtagatg ttaactgcaa    4020
aaatgaggta ttgtcatgtg tagtgcacca catggtatta aatttcatca ggtgtaagtc    4080
aatagaggag aatttcagca ttacattgga tcattctcag acgacagtaa gacatgctga    4140
caaggttcgc cgactctcgc ttcacttcag caatgcacat gatacaacac cactagcagg    4200
tttgagactc tcacaagttc gatcgatggc attttttcgga caagtcaagt gtatgccttc    4260
```

```
cattgcagat tataggcttt ttcgagttct gattctttgt ttttgggctg atcaagagaa    4320
aacaagctat gacctcacaa gcatttttga actgttacaa ctgagatatc tgaagataac    4380
aggtaatatc acagttaaac ttccagagaa gatccaagga ctacaacact tgcagacact    4440
ggaagcagat gcaagagcaa ctgctgtcct attggatatt gttcatacac agtgtttgtt    4500
gcaccttcgt cttgtactac ttgatctgct ccctcactgt cacaggtaca tcttcaccag    4560
catccccaaa tggactggaa agctcaacaa tctccgcatt ttaaacattg cagtcatgca    4620
aatttcccag gatgaccttg acactctcaa aggactggga tctctcactg ctctttcgct    4680
gcttgttcga acagcgcctg cgcaaagaat cgtcgctgcg aatgaggggt tcgggtctct    4740
caagtacttc atgtttgtct gtacagcacc atgcatgact tttgtggaag gagcaatgcc    4800
gagtgtgcaa aggttaaatc taaggttcaa tgccaacgag ttcaagcagt atgactctaa    4860
ggagacaggg ttgaacact tggtcgccct tgcagagatc tctgcaagaa ttgggggcac    4920
tgatgatgat gaatcaaaca aaactgaagt ggagtctgcc ttgaggactg caattcgcaa    4980
gcatccgacg ccgagcactc ttatggttga tatacaatgg gtggattgga tctttggtgc    5040
tgaagggaga gacttggatg aagatttggc acaacaagat gatcacgggt atggattttt    5100
cattctattc ccaggttaca acttacaagg attattgagc ttctttcttt ctctgccgtg    5160
gcttctatct ttacctgcta tgcatcttca acctgacttg atgattgttt gaaccaagc    5220 tt                                                                   5222

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 69
cacgtggaat tccccgggg                                                 19

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 70 gtaccccgg ggaattccac gtg                                             23

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 71
cccggggaat tcctgcagaa ggtgcaagga ttgctggagc g                        41

<210> SEQ ID NO 72
<211> LENGTH: 52
<212> TYPE: DNA
<213> ORGANISM: Artificial Sequence
```

-continued

```
<220> FEATURE:
<223> OTHER INFORMATION: Description of Artificial Sequence:Synthetic
      oligonucleotide

<400> SEQUENCE: 72
tttaaaggta ccccatggca cgtgccggct tgttgtggtc ttttgggttc ac              52

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 73
gccggcacgt gccatgattg aacgctattc ccaatg                               36

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 74
gccgggatcc ccctctattg ttagattgac                                      30
```